US008741905B2

(12) United States Patent
Wagner et al.

(10) Patent No.: US 8,741,905 B2
(45) Date of Patent: Jun. 3, 2014

(54) COMPOUNDS AND METHODS FOR TREATING AUTOIMMUNE DISEASES

(71) Applicants: The Broad Institute, Inc., Cambridge, MA (US); President and Fellows of Harvard College, Cambridge, MA (US)

(72) Inventors: Bridget Wagner, Medford, MA (US); Jeremy Duvall, Wakefield, MA (US); Danny Hung-Chieh Chou, Cambridge, MA (US)

(73) Assignees: The Broad Institute, Inc., Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/887,466

(22) Filed: May 6, 2013

(65) Prior Publication Data

US 2013/0317043 A1 Nov. 28, 2013

Related U.S. Application Data

(63) Continuation of application No. PCT/US2011/059405, filed on Nov. 4, 2011.

(60) Provisional application No. 61/410,558, filed on Nov. 5, 2010.

(51) Int. Cl.

| | |
|---|---|
| ***A61K 31/395*** | (2006.01) |
| ***A61K 31/404*** | (2006.01) |
| ***A61K 45/06*** | (2006.01) |

(52) U.S. Cl.

USPC ...... 514/255.03; 514/183; 514/414; 514/452; 435/374

(58) Field of Classification Search

USPC .............. 514/255.03, 183, 414, 452; 435/374

See application file for complete search history.

(56) References Cited

U.S. PATENT DOCUMENTS

| | | | | |
|---|---|---|---|---|
| 2013/0053380 | A1* | 2/2013 | Kinzel et al. | 514/233.8 |
| 2013/0261101 | A1* | 10/2013 | Combs et al. | 514/210.18 |
| 2013/0317043 | A1* | 11/2013 | Wagner et al. | 514/255.03 |

* cited by examiner

*Primary Examiner* — Raymond Henley, III

(74) *Attorney, Agent, or Firm* — Elmore Patent Law Group, P.C.; Roy P. Issac; Carolyn S. Elmore, Esq.

(57) ABSTRACT

The invention relates to a compound of Formula I:

Formula I

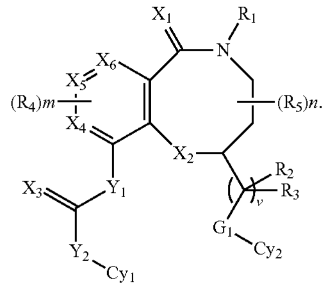

34 Claims, 18 Drawing Sheets

| Symbol | *p*-value | Description |
| --- | --- | --- |
| Mcm6 | $2.3 * 10^{-26}$ | DNA replication licensing factor MCM6 |
| Blvrb | $7.2 * 10^{-23}$ | biliverdin reductase B |
| Usp9x | $2.1 * 10^{-9}$ | ubiquitin specific peptidase 9, X-linked isoform |
| Ap3b2 | $1.0 * 10^{-6}$ | adaptor-related protein complex 3, beta 2 |
| Cand1 | $7.5 * 10^{-6}$ | cullin-associated and neddylation-dissociated 1 |
| N/A | $3.3 * 10^{-5}$ | similar to Gapdh |
| N/A | $7.0 * 10^{-5}$ | similar to TBC1 domain family member 15 |
| Gapdh | $7.8 * 10^{-5}$ | glyceraldehyde-3-phosphate dehydrogenase |
| Ahcy | $8.7 * 10^{-5}$ | adenosylhomocysteinase |
| Kpna4 | $1.6 * 10^{-4}$ | importin 4 |
| N/A | $4.2 * 10^{-4}$ | similar to CG5937-PA |
| Lrpprc | $1.0 * 10^{-3}$ | leucine-rich PPR motif-containing protein |
| Ipo9 | $5.1 * 10^{-3}$ | importin 9 |
| Retsat | $5.4 * 10^{-3}$ | all-trans-retinol 13,14-reductase |
| Xpo1 | $1.1 * 10^{-2}$ | exportin 1 |
| Timm44 | $2.7 * 10^{-2}$ | translocase of inner mitochondrial membrane 44 |
| Cand2 | $5.1 * 10^{-2}$ | cullin-associated and neddylation-dissociated 2 |

FIG. 12

COMPOUNDS AND METHODS FOR TREATING AUTOIMMUNE DISEASES

RELATED APPLICATIONS

This application is a continuation of International Application No. PCT/US2011/059405, which designated the United States and was filed on Nov. 4, 2011, published in English, which claims the benefit of U.S. Provisional Application No. 61/410,558, filed on Nov. 5, 2010. The entire teachings of the above applications are incorporated herein by reference.

GOVERNMENT SUPPORT

The invention was supported, in whole or in part, by a grant DP2-DK083048 from NIH-NIDDK. The Government has certain rights in the invention.

FIELD OF THE INVENTION

This invention relates to the treatment autoimmune diseases including type-1 diabetes, lupus and rheumatoid arthritis.

BACKGROUND OF THE INVENTION

Type-1 diabetes is caused by the autoimmune destruction of insulin producing β-cells in the pancreas. β-cell apoptosis involves a set of signaling cascades initiated by interleukin-1β (IL-1β), interferon-γ (IFN-γ), and tumor necrosis factor-α (TNF-α). (Chou et al., ACS Chem. Biol. 2010 Aug. 20; 5(8): 729-34). IL-1 β and TNF-α induce NFκB expression, and downstream activation of gene expression is thought to occur through nitric oxide (NO) signaling, which both increases endoplasmic reticulum stress-response pathways and decreases β cell-specific functions. NO is a highly reactive molecule that inhibits the electron-transport chain, leading to decreases in glucose oxidation rates, ATP generation, and insulin production; cellular nitrite is more stable and serves as a surrogate marker for NO. NFκB activation and IFN-α-induced STAT-1 signaling work together to effect β-cell apoptosis, mainly involving the intrinsic apoptotic pathway in both rodents and humans. The downstream effector of this cascade, caspase-3, results in apoptosis and the loss of the ability to secrete insulin in response to glucose stimulation. Cnop et al., Diabetes 54, (Suppl 2), S97-107, 2005; Formoni et al., Diabetologia 51, 298-308, 2008; Soldevila et al., J. Autoimmun. 4, 291-306, 1991; Darville et al., Diabetologia 41, 1101-1108, 1998. Kharroubi et al., Endocrinology 145, 5087-5096, 2004; Mandrup-Poulsen et al., Diabetologia 39, 1005-1029, 1996.

For decades, the standard of care for this disease has been insulin therapy via intramuscular injection. Current approaches to develop new treatments have prioritized islet transplantation) and directed stem-cell differentiation, while many technological advances have focused on glucose detection and insulin delivery. Recent development of techniques to treat diabetic mice with partially differentiated stem cells indicates that procedures resulting in an increase in beta-cell mass can ameliorate type-1 diabetes. While cell-based treatments show promise, a chemical intervention capable of restoring glycemic control in type-1 diabetes would have enormous impact clinically, by enabling an in vivo pancreatic effect while avoiding the need for immunosuppression.

SUMMARY OF THE INVENTION

The invention relates to compounds of Formula I or a prodrug or metabolite thereof:

Formula I

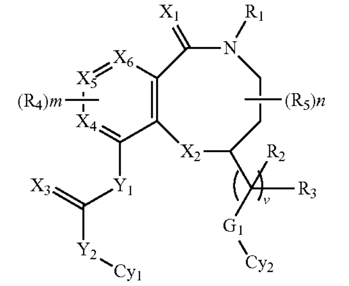

wherein,

Each $X_1$ and $X_3$ is independently —O— or —S—;

Each $X_4$, $X_5$ and $X_6$ is independently —CH or —N—;

Each $X_2$, $Y_1$ and $Y_2$ is independently —$NR_{10}$, —S— or —O—;

$Cy_1$ is an optionally substituted aryl group;

$Cy_2$ is an optionally substituted cycloalkyl, optionally substituted cycloalkenyl, optionally substituted heterocyclyl or optionally substituted aryl containing one, two or three rings;

$R_1$, is hydrogen, halogen, aliphatic, substituted aliphatic, aryl or substituted aryl;

Each $R_2$, $R_3$, $R_4$ and $R_5$ is independently selected from absent, hydrogen, halogen, —$OR_{10}$, —$SR_{10}$, —$NR_{10}R_{11}$, —C(O)$R_{10}$, —C(O)$OR_{10}$, —C(O)$NR_{10}R_{11}$, —N($R_{10}$)C(O)$R_{11}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, optionally substituted aliphatic, optionally substituted aryl or optionally substituted heterocyclyl;

$G_1$ is —N($R_{10}$)C(O)—, —N($R_{10}$)C(S)—, —N($R_{10}$)S(O)$_2$—, —N($R_{10}$)S(O)$_2$—[C($R_{10}$)($R_{11}$)]$_W$—, —N($R_{10}$)C(O)—[C($R_{10}$)($R_{11}$)]$_W$—, —N($R_{10}$)C(S)—[C($R_{10}$)($R_{11}$)]$_W$—, —N($R_{10}$)C(O)N($R_{11}$)—, —N($R_{10}$)C(S)N($R_{11}$)—, —C(O)O— or —C(O)O—[C($R_{10}$)($R_{11}$)]$_W$—;

Each n and m is independently selected from 0, 1, 2 or 3;

Each v and w is independently selected from 0, 1, 2, 3, 4, 5 or 6;

Each $R_{10}$, $R_{11}$, $R_{12}$, $R_{13}$ and $R_{14}$ is independently absent, hydrogen, halogen, —OH, —SH, —$NH_2$, —$CF_3$, —CN, —$NO_2$, —$N_3$, —C(O)OH, —C(O)$NH_2$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two of $R_{10}$, $R_{11}$, $R_{12}$, $R_{13}$ and $R_{14}$ together with the atoms to which they are attached and any intervening atoms may form an additional optionally substituted, 3, 4, 5, 6 or 7 membered ring.

The invention further relates to the treatment of autoimmune diseases by the administration of a compound of Formula I. Compounds of Formula I can be useful for the treatment of autoimmune diseases including multiple sclerosis, Crohn's disease, lupus erythematosus, rheumatoid arthritis, osteoarthritis, psoriasis, ulcerative colitis, type-1 diabetes, pancreatitis, asthma, idiopathic thrombocytopenia purpura, uveitis, Guillain-Barre syndrome or myasthenia gravis.

BRIEF DESCRIPTION OF THE DRAWINGS

FIG. 12: Candidate proteins identified by SILAC and mass spectrometry analysis.

DETAILED DESCRIPTION OF THE INVENTION

Formula I

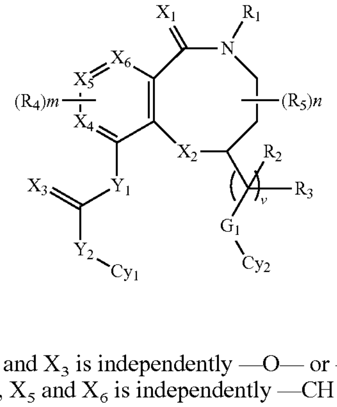

Figure 1:
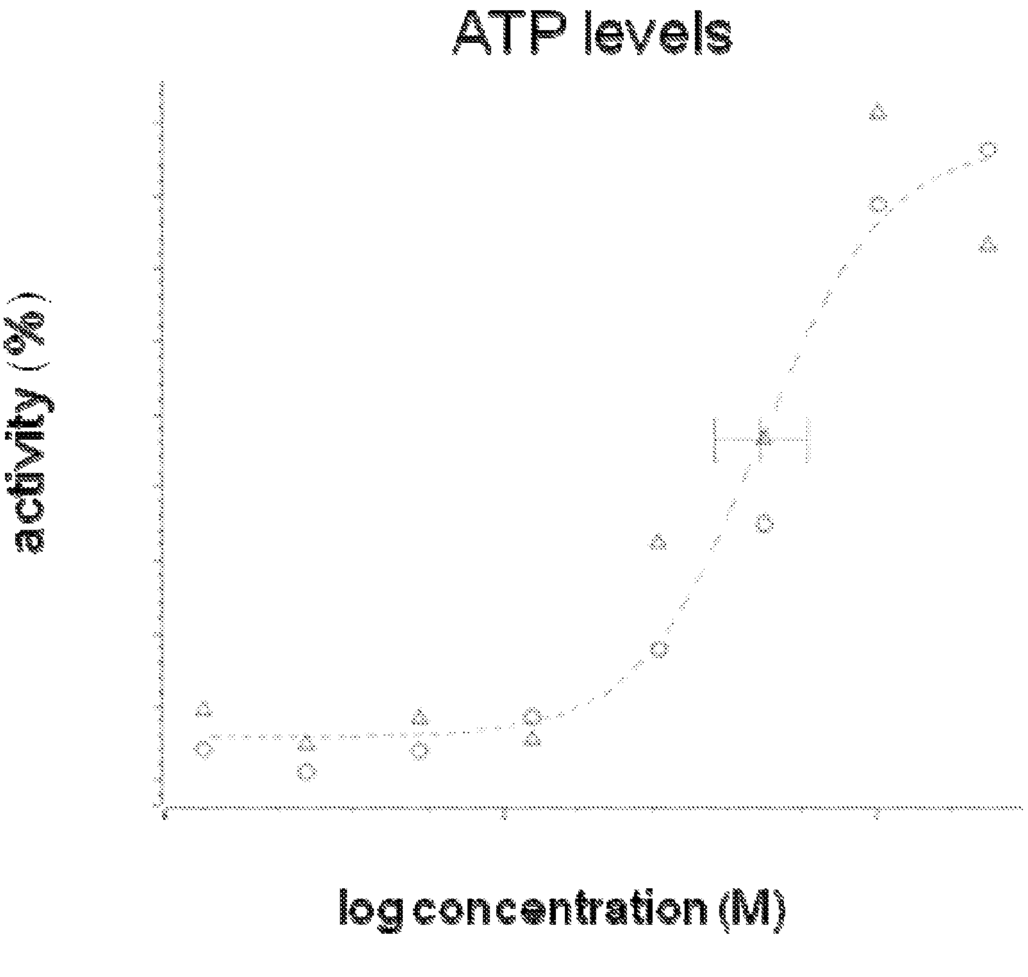
FIG. 1: Cellular ATP Levels after incubation with Compound-1A.
Figure 2:
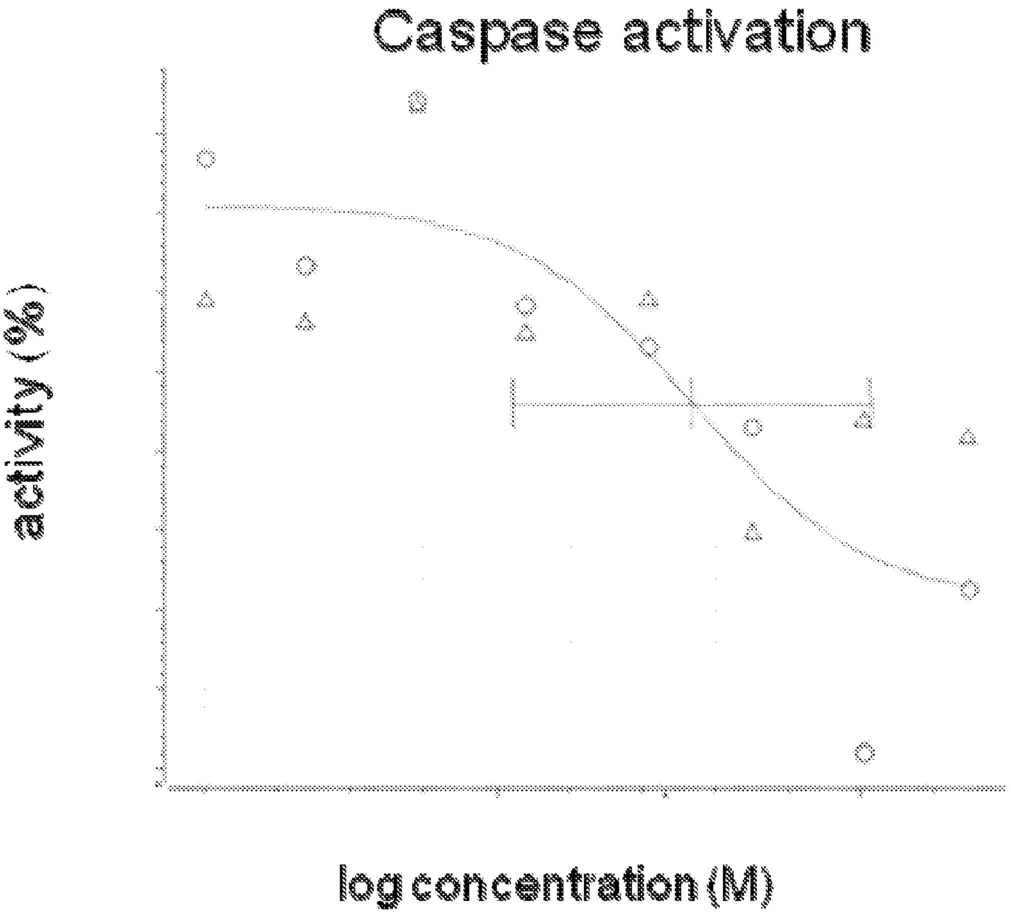
FIG. 2: Caspase activation after incubation with Compound-1A.
Figure 3:
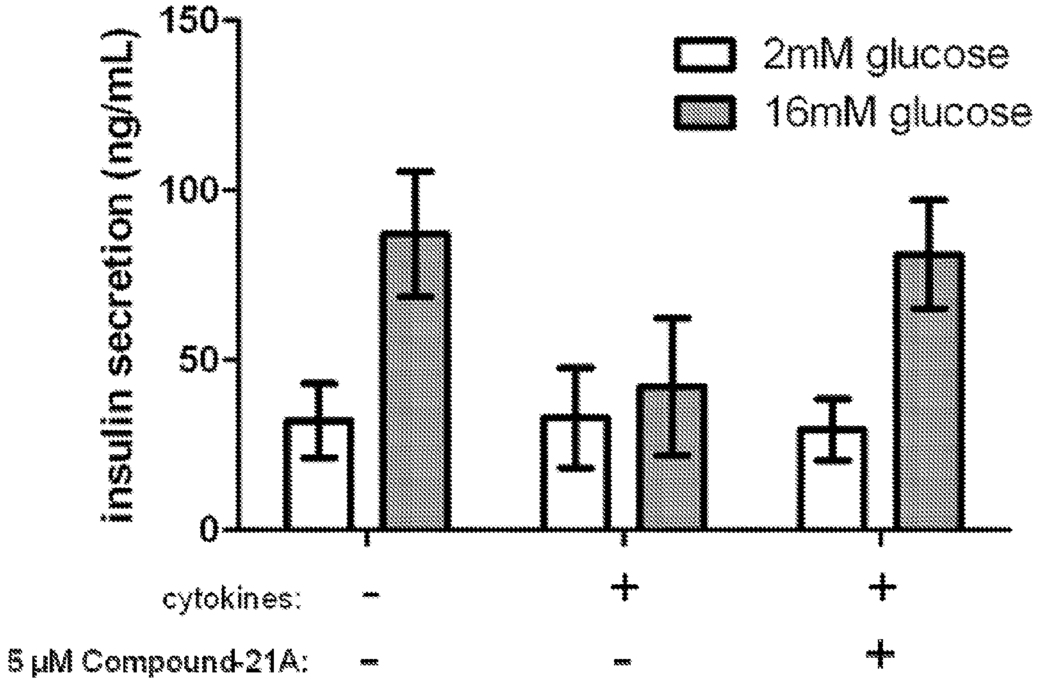
FIG. 3: Glucose-stimulated insulin secretion with Compound-21A.

wherein,

Each $X_1$ and $X_3$ is independently —O— or —S—;

Each $X_4$, $X_5$ and $X_6$ is independently —CH or —N—;

Each $X_2$, $Y_1$ and $Y_2$ is independently —$NR_{10}$, —S— or —O—;

$Cy_1$ is an optionally substituted aryl group;

$Cy_2$ is an optionally substituted cycloalkyl, optionally substituted cycloalkenyl, optionally substituted heterocyclyl or optionally substituted aryl containing one, two or three rings;

$R_1$ is hydrogen, halogen, aliphatic, substituted aliphatic, aryl or substituted aryl;

Each $R_2$, $R_3$, $R_4$ and $R_5$ is independently selected from absent, hydrogen, halogen, —$OR_{10}$, —$SR_{10}$, —$NR_{10}R_{11}$, —C(O)$R_{10}$, —C(O)$OR_{10}$, —C(O)$NR_{10}R_{11}$, —N($R_{10}$)C(O)$R_{11}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, optionally substituted aliphatic, optionally substituted aryl or optionally substituted heterocyclyl;

$G_1$ is —N($R_{10}$)C(O)—, —N($R_{10}$)C(S)—, —N($R_{10}$)S(O)$_2$—, —N($R_{10}$)S(O)$_2$—[C($R_{10}$)($R_{11}$)]$_w$—, —N($R_{10}$)C(O)—[C($R_{10}$)($R_{11}$)]$_w$—, —N($R_{10}$)C(S)—[C($R_{10}$)($R_{11}$)]$_w$—, —N($R_{10}$)C(O)N($R_{11}$)—, —N($R_{10}$)C(S)N($R_{11}$)—, —C(O)O— or —C(O)O—[C($R_{10}$)($R_{11}$)]$_w$—; Each n and m is independently selected from 0, 1, 2 or 3;

Each v and w is independently selected from 0, 1, 2, 3, 4, 5 or 6;

Each $R_{10}$, $R_{11}$, $R_{12}$, $R_{13}$ and $R_{14}$ is independently absent, hydrogen, halogen, —OH, —SH, —$NH_2$, —$CF_3$, —CN, —$NO_2$, —$N_3$, —C(O)OH, —C(O)$NH_2$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two of $R_{10}$, $R_{11}$, $R_{12}$, $R_{13}$ and $R_{14}$ together with the atoms to which they are attached and any intervening atoms may form an additional optionally substituted, 3, 4, 5, 6 or 7 membered ring.

In a preferred embodiment $Cy_1$ is selected from:

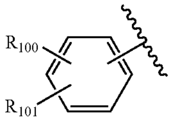
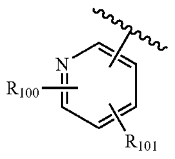
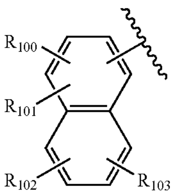

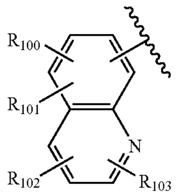
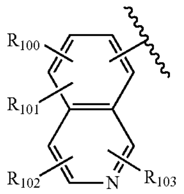
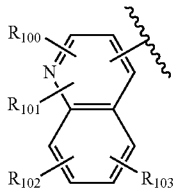

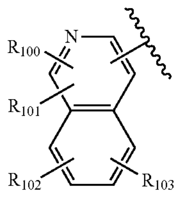
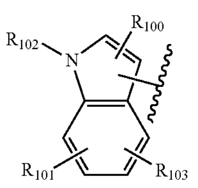

-continued

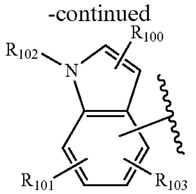

wherein each $R_{100}$, $R_{101}$, $R_{102}$ and $R_{103}$ is independently absent, hydrogen, halogen, —$OR_{10}$, —$SR_{10}$, —$NR_{10}R_{11}$, —$C(O)R_{10}$, —$C(O)OR_{10}$, —$C(O)NR_{10}R_{11}$, —$N(R_{10})C(O)R_{11}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl.

In a preferred embodiment $Cy_2$ is selected from;

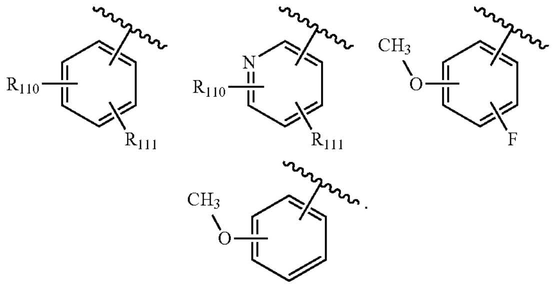

In a preferred embodiment $X_1$ is —O—.

In a preferred embodiment $X_2$ is —O—.

In a preferred embodiment $X_3$ is —O—.

In a preferred embodiment $X_4$ is —CH.

In a preferred embodiment $X_5$ is —CH.

In a preferred embodiment $X_6$ is —CH.

In a preferred embodiment n is 1, and $R_5$ is —$CH_3$.

In a preferred embodiment m is 0.

In a preferred embodiment $Y_1$ is —NH.

In a preferred embodiment $Y_2$ is —NH.

In a preferred embodiment $R_1$ is hydroxyl substituted alkyl.

In a preferred embodiment $R_2$ and $R_3$ are hydrogen and v is 1.

In a preferred embodiment $Cy_1$ is naphthyl or substituted naphthyl.

In a preferred embodiment $Cy_2$ is an optionally substituted phenyl.

In a preferred embodiment $G_1$ is —$N(H)S(O)_2$—.

In a preferred embodiment, the invention relates to a compound of Formula II:

Formula II

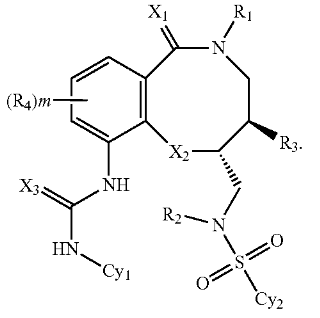

In a preferred embodiment a compound of Formula I is selected from Table A:

TABLE A

| No. | Compound |
|---|---|
| 1 | 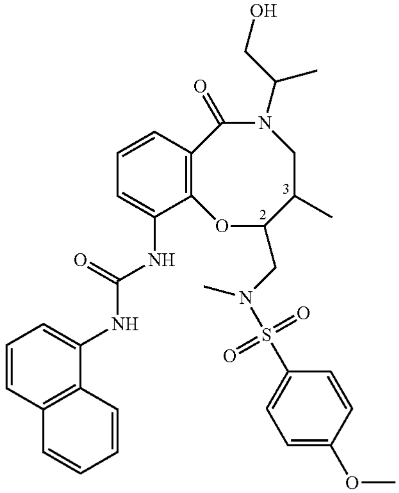 [SMILES: COc1ccc(S(=O)(=O)N(C)CC2Oc3c(NC(=O)Nc4cccc5ccccc45)cccc3C(=O)N(C(C)CO)CC2C)cc1] |
| 2 | 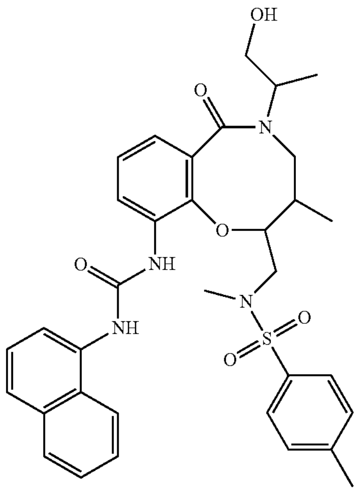 [SMILES: Cc1ccc(S(=O)(=O)N(C)CC2Oc3c(NC(=O)Nc4cccc5ccccc45)cccc3C(=O)N(C(C)CO)CC2C)cc1] |
| 3 | 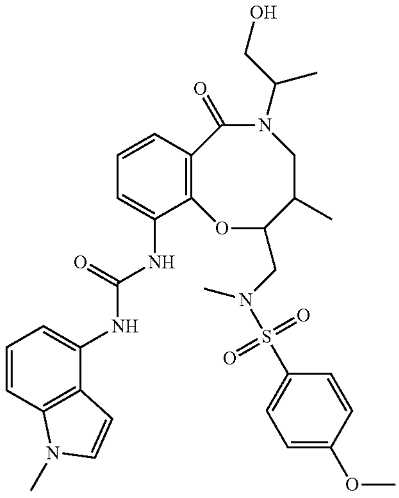 [SMILES: COc1ccc(S(=O)(=O)N(C)CC2Oc3c(NC(=O)Nc4cccc5c4ccn5C)cccc3C(=O)N(C(C)CO)CC2C)cc1] |

TABLE A-continued
| No. | Compound |
| --- | --- |
| 4 | 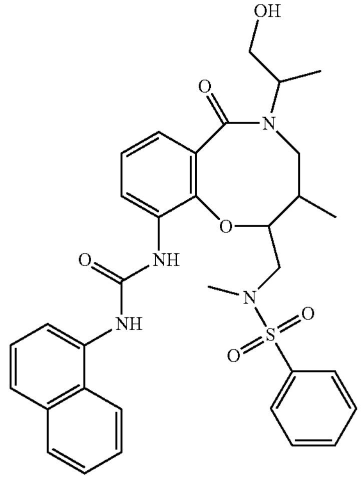 [SMILES: CC1CN(C(C)CO)C(=O)c2cccc(NC(=O)Nc3cccc4ccccc34)c2OC1CN(C)S(=O)(=O)c1ccccc1] |
| 5 | 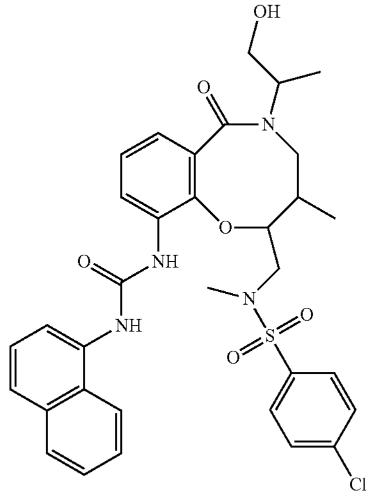 [SMILES: CC1CN(C(C)CO)C(=O)c2cccc(NC(=O)Nc3cccc4ccccc34)c2OC1CN(C)S(=O)(=O)c1ccc(Cl)cc1] |
| 6 | 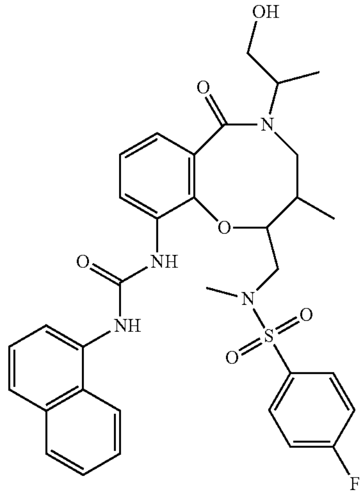 [SMILES: CC1CN(C(C)CO)C(=O)c2cccc(NC(=O)Nc3cccc4ccccc34)c2OC1CN(C)S(=O)(=O)c1ccc(F)cc1] |
TABLE A-continued
| No. | Compound |
| --- | --- |
| 7 | 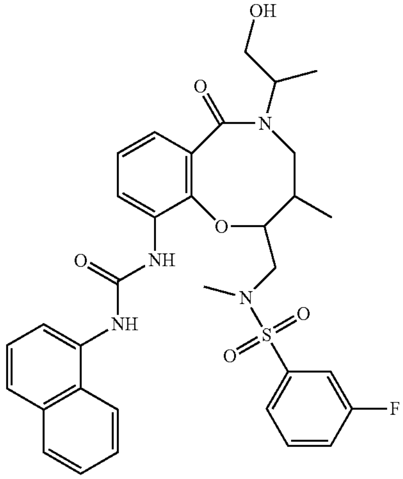 [SMILES: CC1CN(C(C)CO)C(=O)c2cccc(NC(=O)Nc3cccc4ccccc34)c2OC1CN(C)S(=O)(=O)c1cccc(F)c1] |
| 8 | 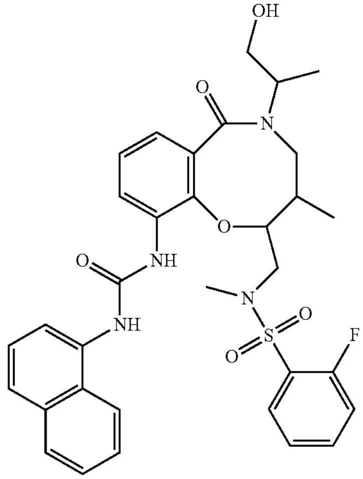 [SMILES: CC1CN(C(C)CO)C(=O)c2cccc(NC(=O)Nc3cccc4ccccc34)c2OC1CN(C)S(=O)(=O)c1ccccc1F] |
| 9 | 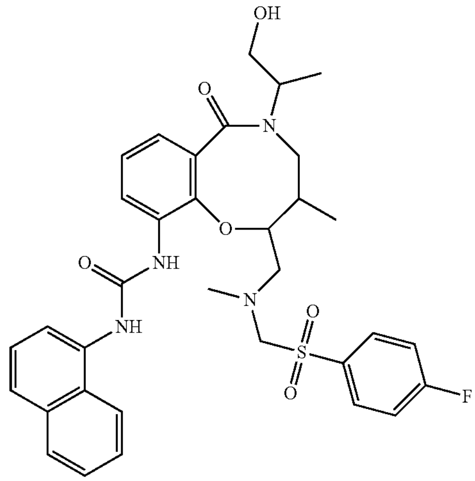 [SMILES: CC1CN(C(C)CO)C(=O)c2cccc(NC(=O)Nc3cccc4ccccc34)c2OC1CN(C)CS(=O)(=O)c1ccc(F)cc1] |

TABLE A-continued
| No. | Compound |
|---|---|
| 10 | 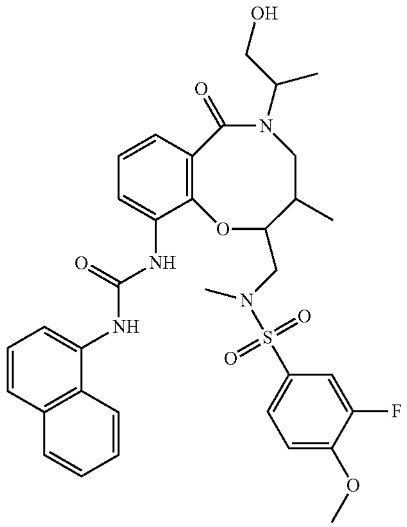 [SMILES: COc1ccc(S(=O)(=O)N(C)CC2Oc3c(NC(=O)Nc4cccc5ccccc45)cccc3C(=O)N(C(C)CO)CC2C)cc1F] |
| 11 | 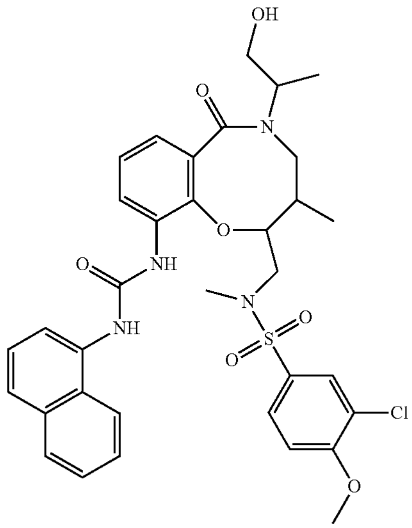 [SMILES: COc1ccc(S(=O)(=O)N(C)CC2Oc3c(NC(=O)Nc4cccc5ccccc45)cccc3C(=O)N(C(C)CO)CC2C)cc1Cl] |
TABLE A-continued
| No. | Compound |
|---|---|
| 12 | 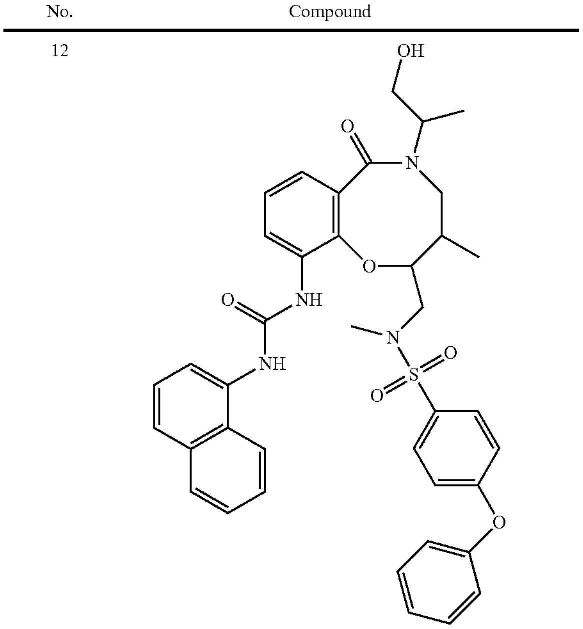 |
| 13 | 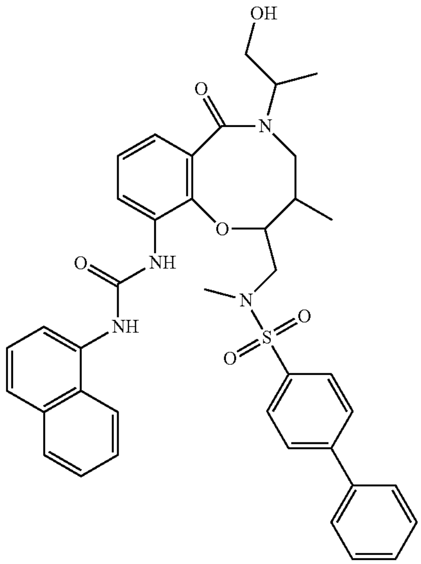 [SMILES: CC1CN(C(C)CO)C(=O)c2cccc(NC(=O)Nc3cccc4ccccc34)c2OC1CN(C)S(=O)(=O)c1ccc(-c2ccccc2)cc1] |

TABLE A-continued
| No. | Compound |
| --- | --- |
| 14 | 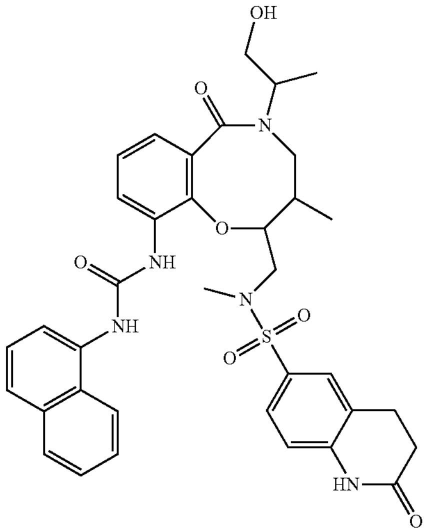 [SMILES: CC1CN(C(C)CO)C(=O)c2cccc(NC(=O)Nc3cccc4ccccc34)c2OC1CN(C)S(=O)(=O)c1ccc2c(c1)CCC(=O)N2] |
| 15 | 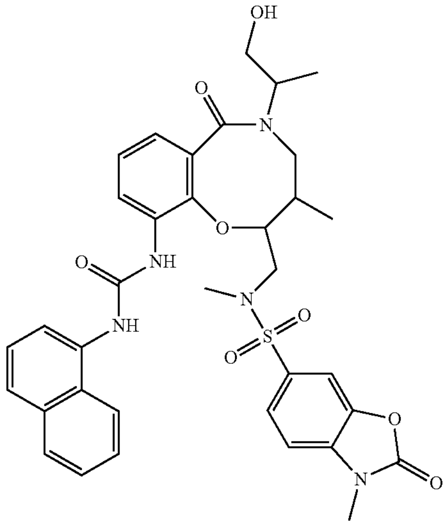 [SMILES: CC1CN(C(C)CO)C(=O)c2cccc(NC(=O)Nc3cccc4ccccc34)c2OC1CN(C)S(=O)(=O)c1ccc2c(c1)oc(=O)n2C] |
| 16 | 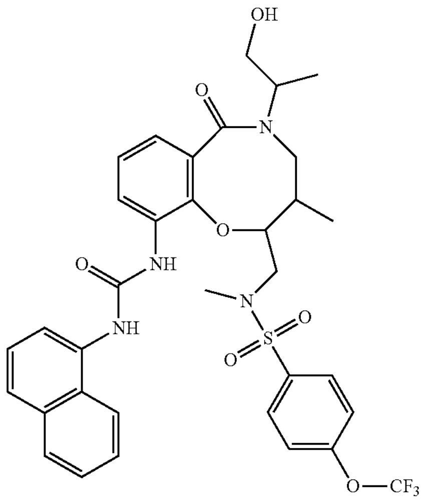 [SMILES: CC1CN(C(C)CO)C(=O)c2cccc(NC(=O)Nc3cccc4ccccc34)c2OC1CN(C)S(=O)(=O)c1ccc(OC(F)(F)F)cc1] |
| 17 | 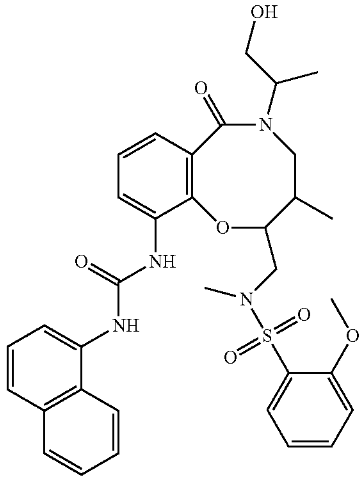 [SMILES: COc1ccccc1S(=O)(=O)N(C)CC1Oc2c(NC(=O)Nc3cccc4ccccc34)cccc2C(=O)N(C(C)CO)CC1C] |
| 18 | 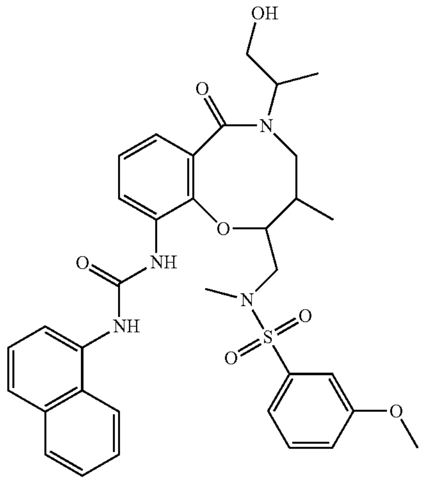 [SMILES: COc1cccc(S(=O)(=O)N(C)CC2Oc3c(NC(=O)Nc4cccc5ccccc45)cccc3C(=O)N(C(C)CO)CC2C)c1] |
| 19 | 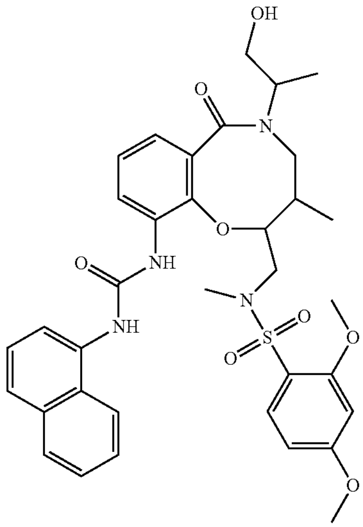 [SMILES: COc1ccc(S(=O)(=O)N(C)CC2Oc3c(NC(=O)Nc4cccc5ccccc45)cccc3C(=O)N(C(C)CO)CC2C)c(OC)c1] |

TABLE A-continued
| No. | Compound |
|---|---|
| 20 | 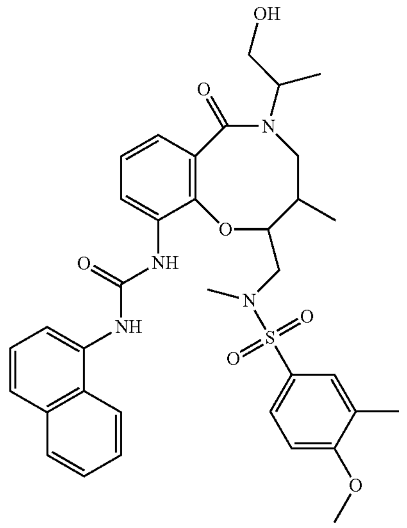 [SMILES: COc1ccc(S(=O)(=O)N(C)CC2Oc3c(NC(=O)Nc4cccc5ccccc45)cccc3C(=O)N(C(C)CO)CC2C)cc1C] |
| 21 | 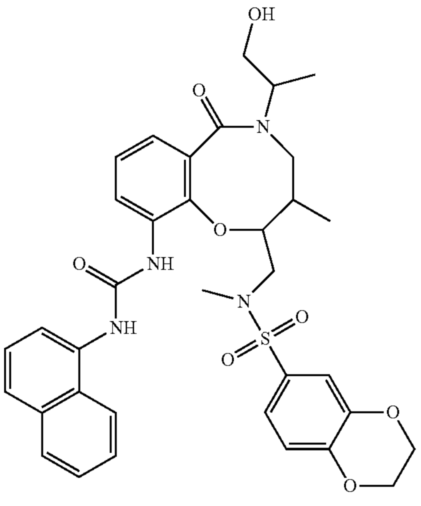 [SMILES: CC1CN(C(C)CO)C(=O)c2cccc(NC(=O)Nc3cccc4ccccc34)c2OC1CN(C)S(=O)(=O)c1ccc2c(c1)OCCO2] |
| 22 | 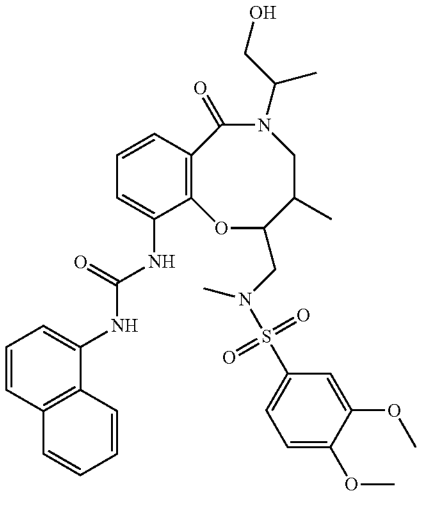 [SMILES: COc1ccc(S(=O)(=O)N(C)CC2Oc3c(NC(=O)Nc4cccc5ccccc45)cccc3C(=O)N(C(C)CO)CC2C)cc1OC] |
TABLE A-continued
| No. | Compound |
|---|---|
| 23 | 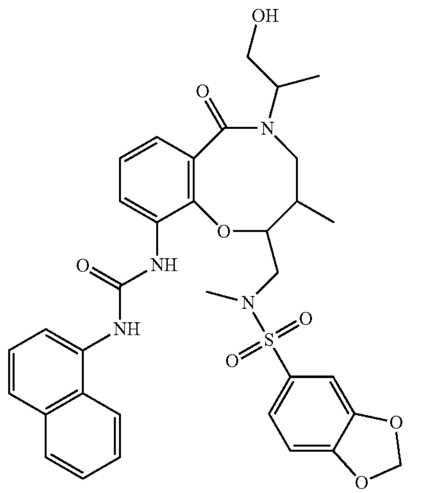 [SMILES: CC1CN(C(C)CO)C(=O)c2cccc(NC(=O)Nc3cccc4ccccc34)c2OC1CN(C)S(=O)(=O)c1ccc2c(c1)OCO2] |
| 24 | 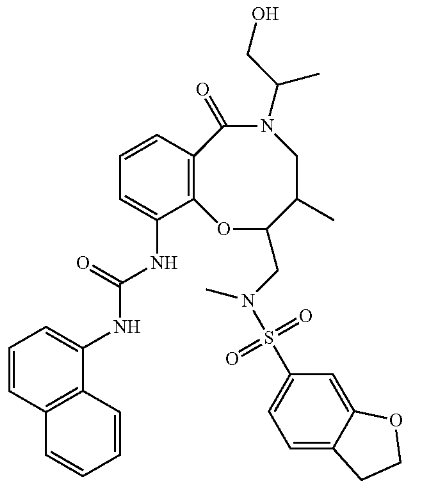 [SMILES: CC1CN(C(C)CO)C(=O)c2cccc(NC(=O)Nc3cccc4ccccc34)c2OC1CN(C)S(=O)(=O)c1ccc2c(c1)OCC2] |
| 25 | 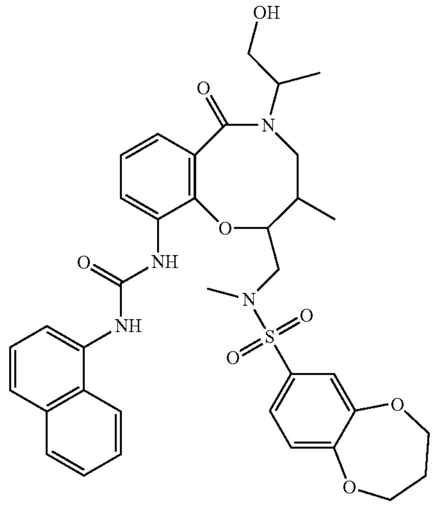 [SMILES: CC1CN(C(C)CO)C(=O)c2cccc(NC(=O)Nc3cccc4ccccc34)c2OC1CN(C)S(=O)(=O)c1ccc2c(c1)OCCCO2] |

TABLE A-continued
| No. | Compound |
| --- | --- |
| 26 | 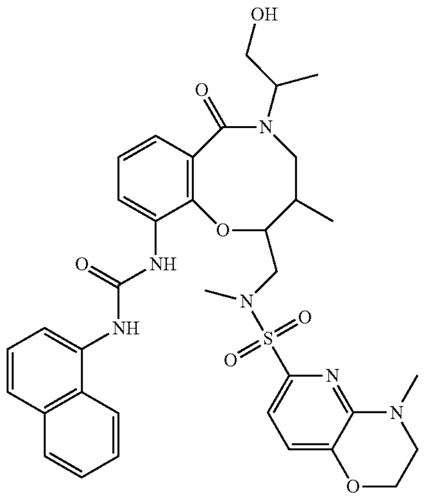 [SMILES: CC1CN(C(C)CO)C(=O)c2cccc(NC(=O)Nc3cccc4ccccc34)c2OC1CN(C)S(=O)(=O)c1ccc2c(n1)N(C)CCO2] |
| 27 | 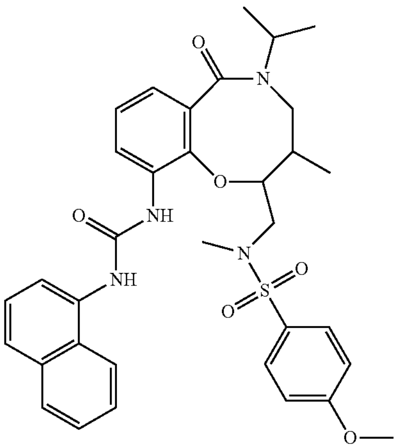 [SMILES: COc1ccc(S(=O)(=O)N(C)CC2Oc3c(NC(=O)Nc4cccc5ccccc45)cccc3C(=O)N(C(C)C)CC2C)cc1] |
| 28 | 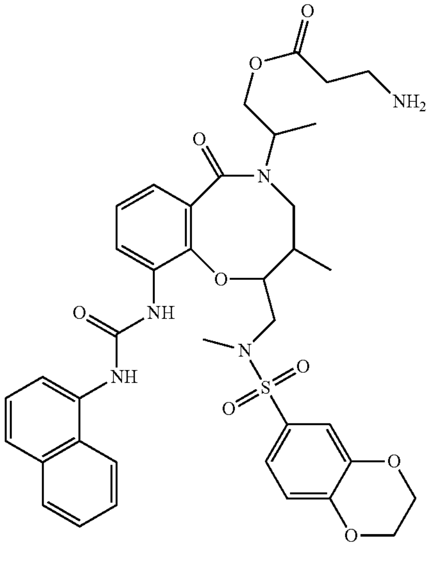 [SMILES: CC1CN(C(C)COC(=O)CCN)C(=O)c2cccc(NC(=O)Nc3cccc4ccccc34)c2OC1CN(C)S(=O)(=O)c1ccc2c(c1)OCCO2] |
TABLE A-continued
| No. | Compound |
| --- | --- |
| 29 | 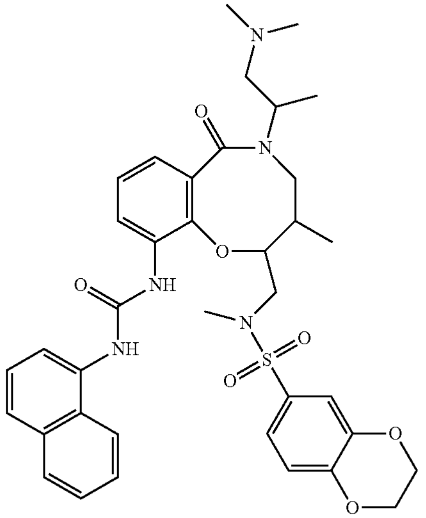 [SMILES: CC1CN(C(C)CN(C)C)C(=O)c2cccc(NC(=O)Nc3cccc4ccccc34)c2OC1CN(C)S(=O)(=O)c1ccc2c(c1)OCCO2] |
| 30 | 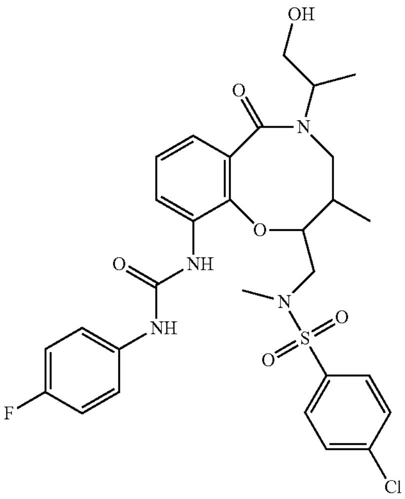 [SMILES: CC1CN(C(C)CO)C(=O)c2cccc(NC(=O)Nc3ccc(F)cc3)c2OC1CN(C)S(=O)(=O)c1ccc(Cl)cc1] |
| 31 | 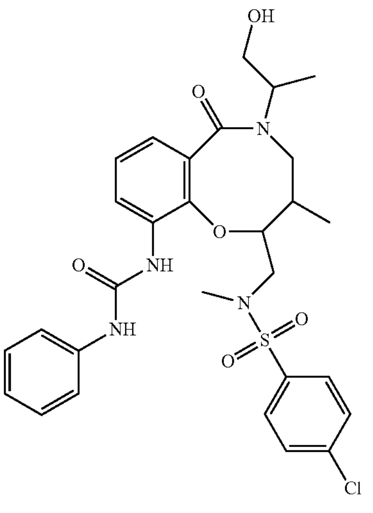 [SMILES: CC1CN(C(C)CO)C(=O)c2cccc(NC(=O)Nc3ccccc3)c2OC1CN(C)S(=O)(=O)c1ccc(Cl)cc1] |

TABLE A-continued
| No. | Compound |
|---|---|
| 32 | 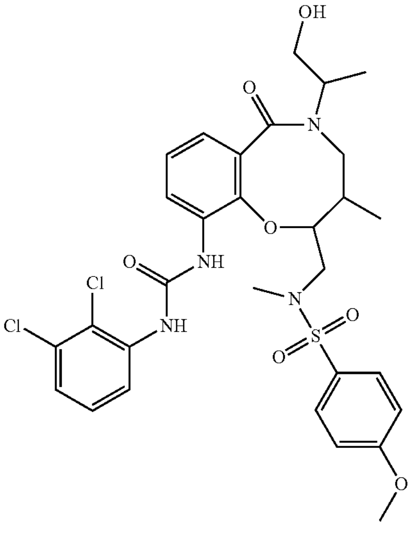 [SMILES: COc1ccc(S(=O)(=O)N(C)CC2Oc3c(NC(=O)Nc4cccc(Cl)c4Cl)cccc3C(=O)N(C(C)CO)CC2C)cc1] |
| 33 | 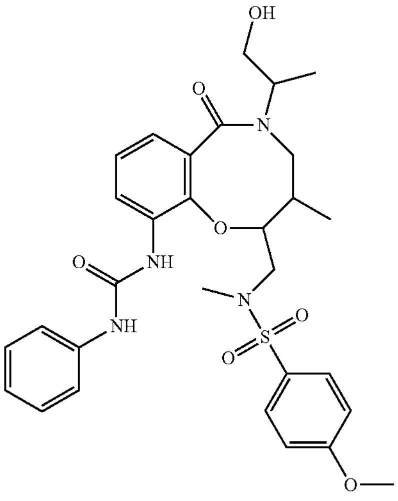 [SMILES: COc1ccc(S(=O)(=O)N(C)CC2Oc3c(NC(=O)Nc4ccccc4)cccc3C(=O)N(C(C)CO)CC2C)cc1] |
| 34 | 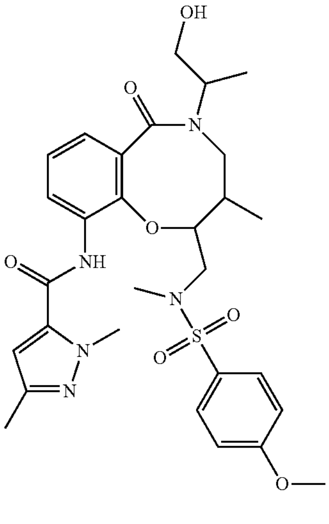 |
| 35 | 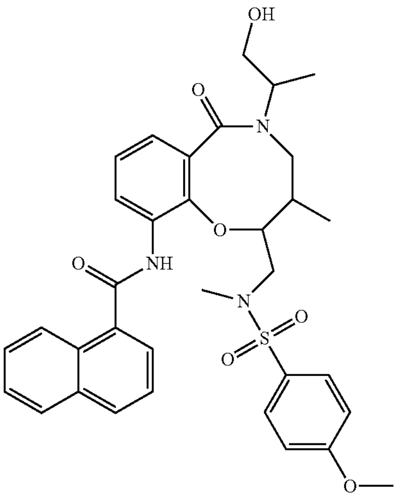 [SMILES: COc1ccc(S(=O)(=O)N(C)CC2Oc3c(NC(=O)c4cccc5ccccc45)cccc3C(=O)N(C(C)CO)CC2C)cc1] |
| 36 | 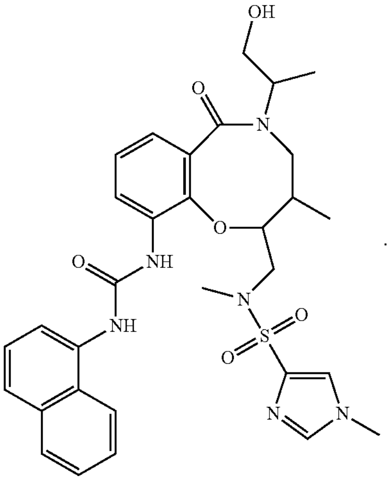 [SMILES: CC1CN(C(C)CO)C(=O)c2cccc(NC(=O)Nc3cccc4ccccc34)c2OC1CN(C)S(=O)(=O)c1cn(C)cn1] |
In a preferred embodiment a compound of Formula I is selected from Table B:

TABLE B
| No. | Compound |
| --- | --- |
| 1A | 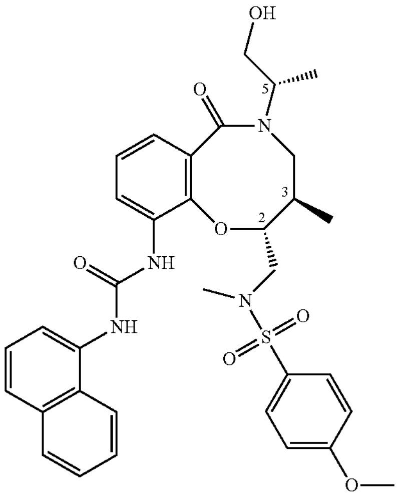 [SMILES: COc1ccc(S(=O)(=O)N(C)C[C@@H]2Oc3c(NC(=O)Nc4cccc5ccccc45)cccc3C(=O)N([C@@H](C)CO)C[C@H]2C)cc1] |
| 2A | 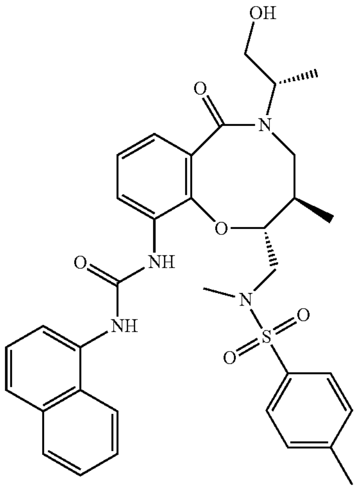 [SMILES: Cc1ccc(S(=O)(=O)N(C)C[C@@H]2Oc3c(NC(=O)Nc4cccc5ccccc45)cccc3C(=O)N([C@@H](C)CO)C[C@H]2C)cc1] |
| 3A | 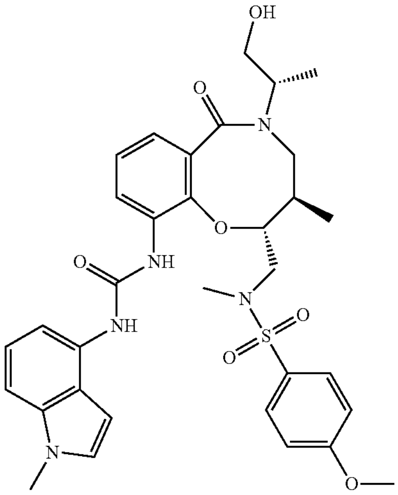 [SMILES: COc1ccc(S(=O)(=O)N(C)C[C@@H]2Oc3c(NC(=O)Nc4cccc5c4ccn5C)cccc3C(=O)N([C@@H](C)CO)C[C@H]2C)cc1] |
TABLE B-continued
| No. | Compound |
| --- | --- |
| 4A | 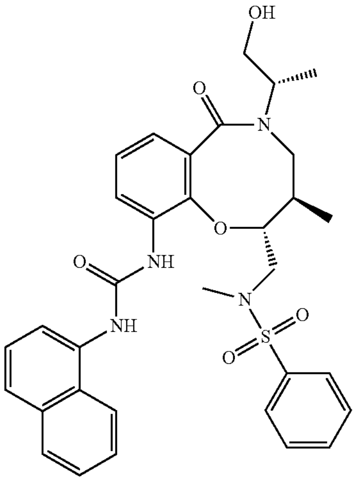 [SMILES: C[C@@H]1CN([C@@H](C)CO)C(=O)c2cccc(NC(=O)Nc3cccc4ccccc34)c2O[C@H]1CN(C)S(=O)(=O)c1ccccc1] |
| 5A | 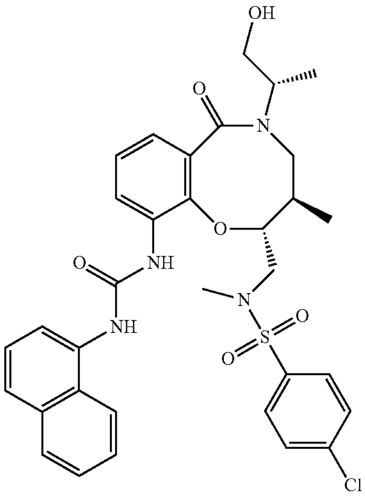 [SMILES: C[C@@H]1CN([C@@H](C)CO)C(=O)c2cccc(NC(=O)Nc3cccc4ccccc34)c2O[C@H]1CN(C)S(=O)(=O)c1ccc(Cl)cc1] |
| 6A | 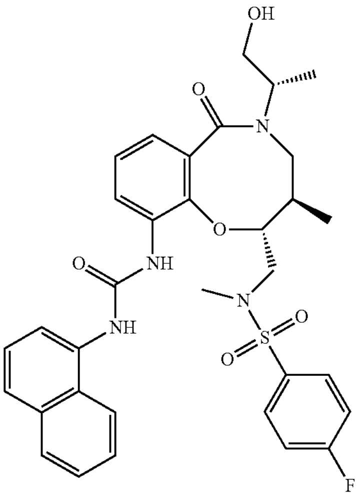 [SMILES: C[C@@H]1CN([C@@H](C)CO)C(=O)c2cccc(NC(=O)Nc3cccc4ccccc34)c2O[C@H]1CN(C)S(=O)(=O)c1ccc(F)cc1] |

TABLE B-continued
| No. | Compound |
| --- | --- |
| 7A | 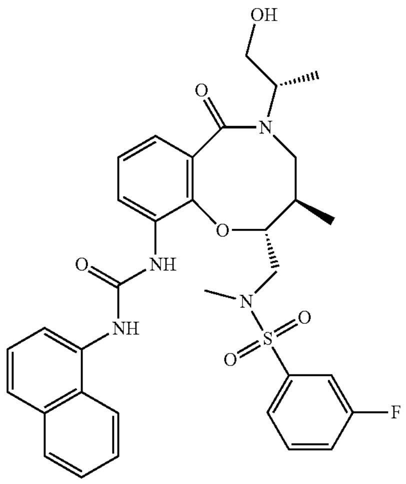 [SMILES: C[C@@H]1CN([C@@H](C)CO)C(=O)c2cccc(NC(=O)Nc3cccc4ccccc34)c2O[C@H]1CN(C)S(=O)(=O)c1cccc(F)c1] |
| 8A | 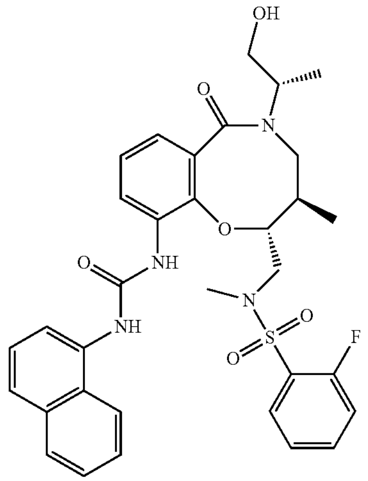 [SMILES: C[C@@H]1CN([C@@H](C)CO)C(=O)c2cccc(NC(=O)Nc3cccc4ccccc34)c2O[C@H]1CN(C)S(=O)(=O)c1ccccc1F] |
| 9A | 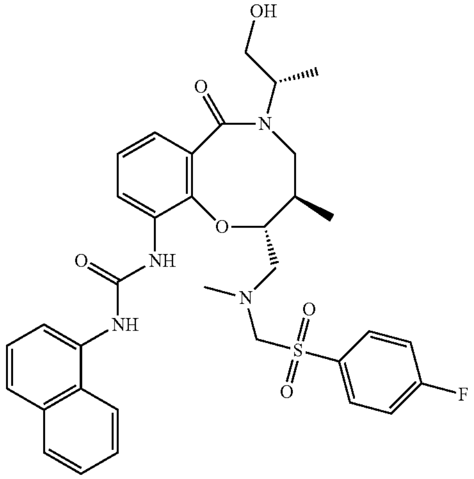 [SMILES: C[C@@H]1CN([C@@H](C)CO)C(=O)c2cccc(NC(=O)Nc3cccc4ccccc34)c2O[C@H]1CN(C)CS(=O)(=O)c1ccc(F)cc1] |
TABLE B-continued
| No. | Compound |
| --- | --- |
| 10A | 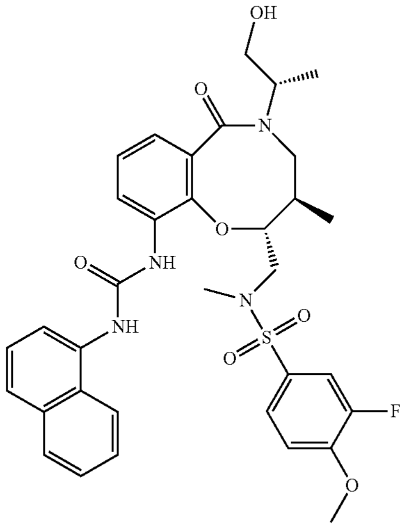 [SMILES: COc1ccc(S(=O)(=O)N(C)C[C@@H]2Oc3c(NC(=O)Nc4cccc5ccccc45)cccc3C(=O)N([C@@H](C)CO)C[C@H]2C)cc1F] |
| 11A | 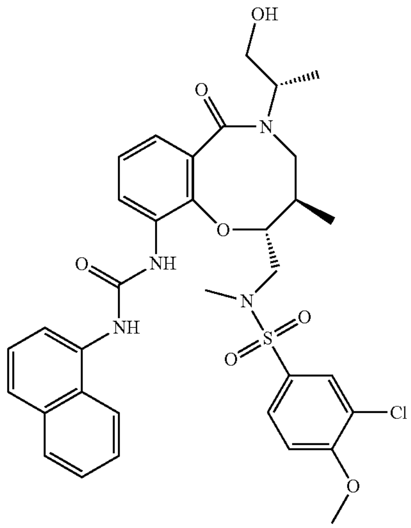 [SMILES: COc1ccc(S(=O)(=O)N(C)C[C@@H]2Oc3c(NC(=O)Nc4cccc5ccccc45)cccc3C(=O)N([C@@H](C)CO)C[C@H]2C)cc1Cl] |

TABLE B-continued
| No. | Compound |
| --- | --- |
| 12A | 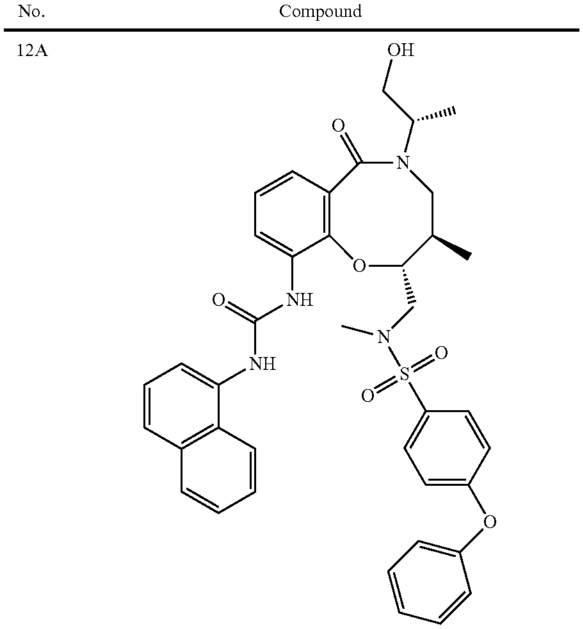 |
| 13A | 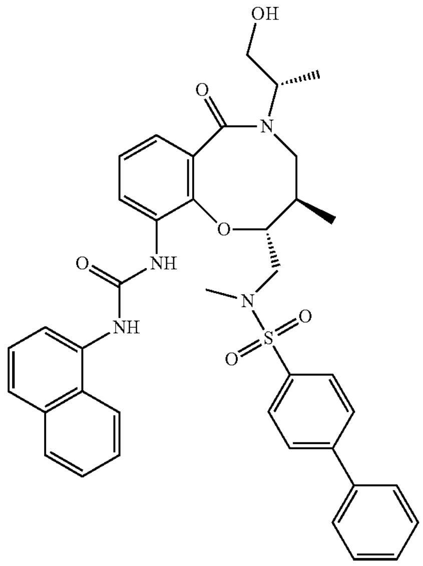 [SMILES: C[C@@H]1CN([C@@H](C)CO)C(=O)c2cccc(NC(=O)Nc3cccc4ccccc34)c2O[C@H]1CN(C)S(=O)(=O)c1ccc(-c2ccccc2)cc1] |
TABLE B-continued
| No. | Compound |
| --- | --- |
| 14A | 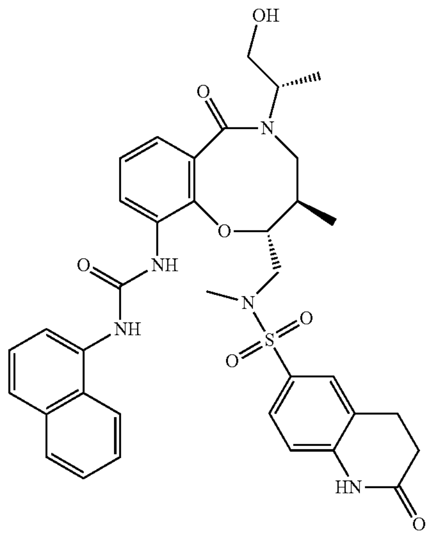 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)CCC(=O)N2] |
| 15A | 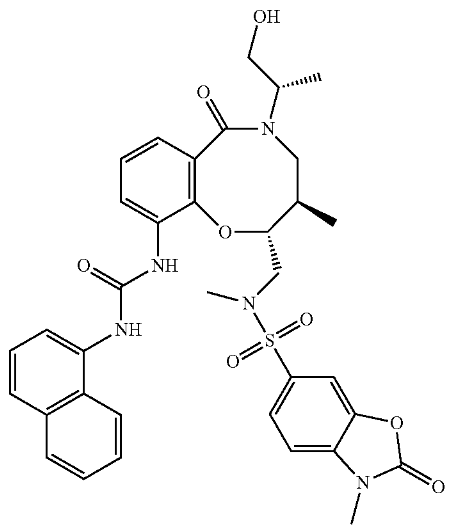 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)oc(=O)n2C] |
| 16A | 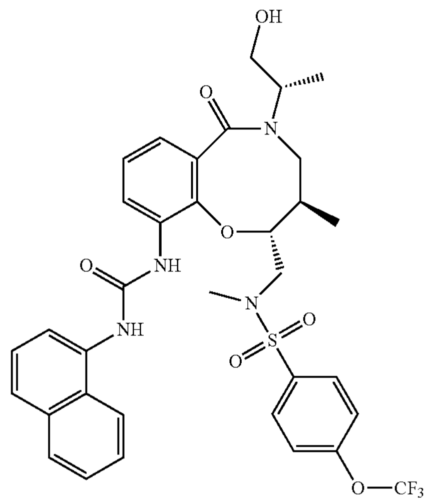 [SMILES: C[C@@H]1CN([C@@H](C)CO)C(=O)c2cccc(NC(=O)Nc3cccc4ccccc34)c2O[C@H]1CN(C)S(=O)(=O)c1ccc(OC(F)(F)F)cc1] |

TABLE B-continued
| No. | Compound |
| --- | --- |
| 17A | 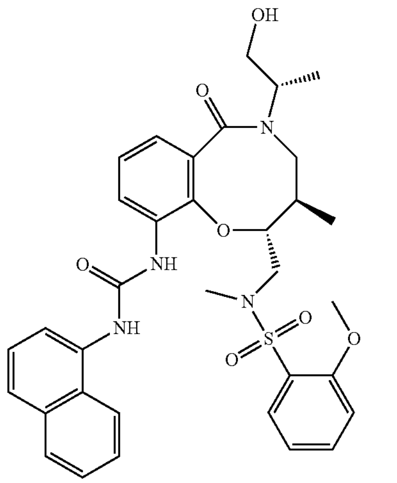 [SMILES: COc1ccccc1S(=O)(=O)N(C)C[C@@H]1Oc2c(NC(=O)Nc3cccc4ccccc34)cccc2C(=O)N([C@@H](C)CO)C[C@H]1C] |
| 18A | 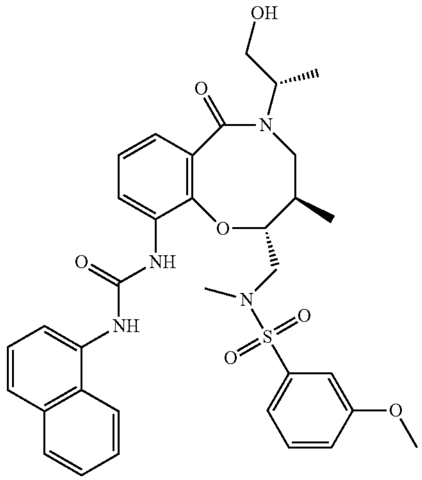 [SMILES: COc1cccc(S(=O)(=O)N(C)C[C@@H]2Oc3c(NC(=O)Nc4cccc5ccccc45)cccc3C(=O)N([C@@H](C)CO)C[C@H]2C)c1] |
| 19A | 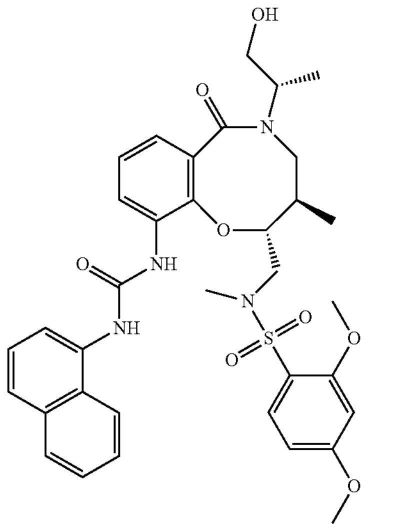 [SMILES: COc1ccc(S(=O)(=O)N(C)C[C@@H]2Oc3c(NC(=O)Nc4cccc5ccccc45)cccc3C(=O)N([C@@H](C)CO)C[C@H]2C)c(OC)c1] |
TABLE B-continued
| No. | Compound |
| --- | --- |
| 20A | 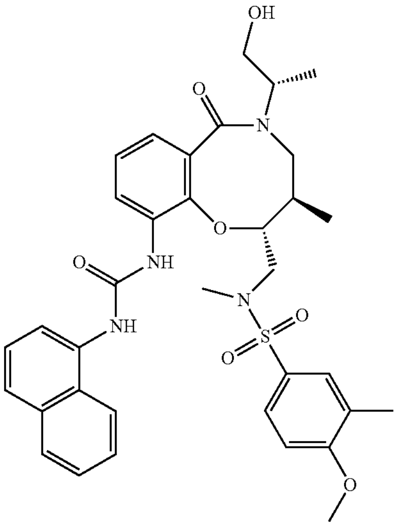 [SMILES: COc1ccc(S(=O)(=O)N(C)C[C@@H]2Oc3c(NC(=O)Nc4cccc5ccccc45)cccc3C(=O)N([C@@H](C)CO)C[C@H]2C)cc1C] |
| 21A | 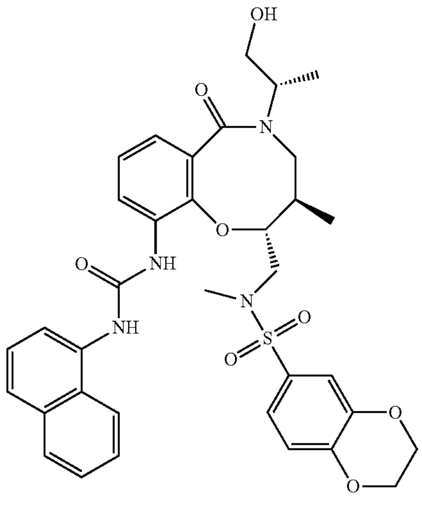 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)OCCO2] |
| 22A | 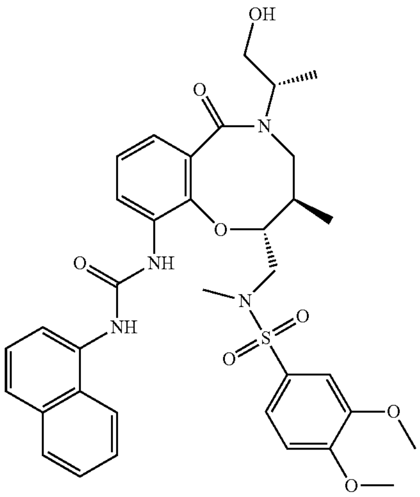 [SMILES: COc1ccc(S(=O)(=O)N(C)C[C@@H]2Oc3c(NC(=O)Nc4cccc5ccccc45)cccc3C(=O)N([C@@H](C)CO)C[C@H]2C)cc1OC] |

TABLE B-continued
| No. | Compound |
|---|---|
| 23A | 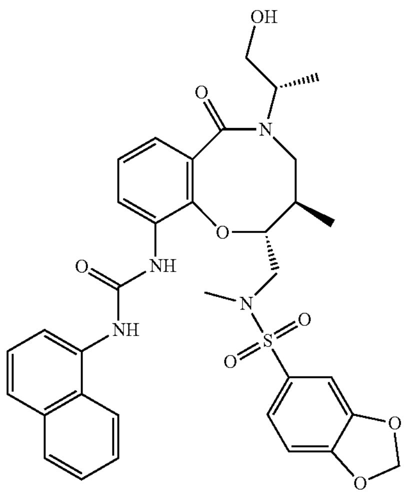 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)OCO2] |
| 24A | 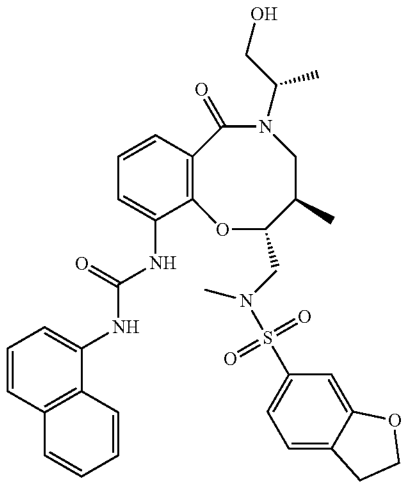 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)OCC2] |
| 25A | 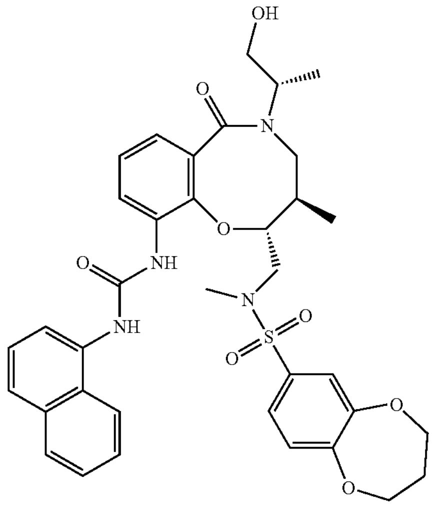 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)OCCCO2] |
TABLE B-continued
| No. | Compound |
|---|---|
| 26A | 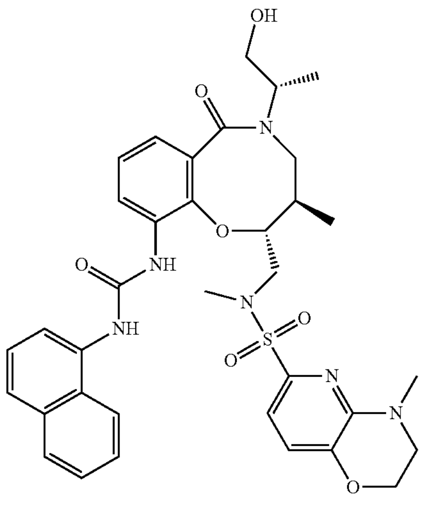 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(n1)N(C)CCO2] |
| 27A | 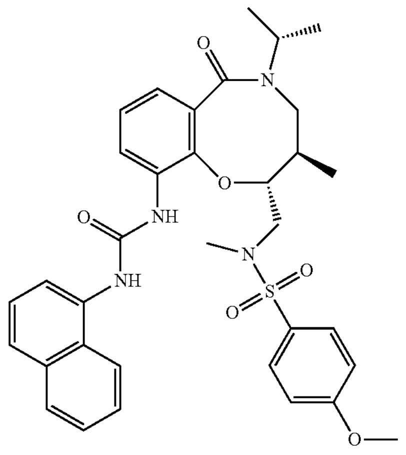 |
| 28A | 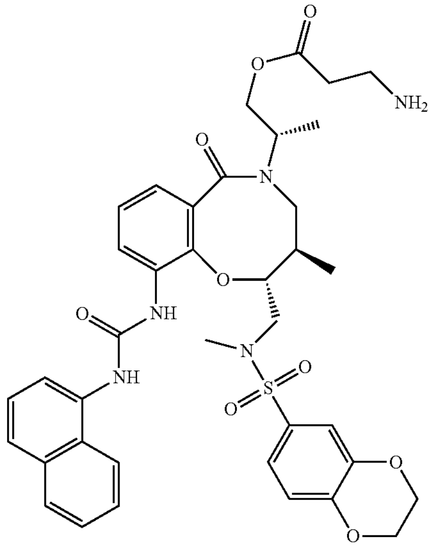 [SMILES: C[C@@H]1CN([C@@H](C)COC(=O)CCN)C(=O)c2cccc(NC(=O)Nc3cccc4ccccc34)c2O[C@H]1CN(C)S(=O)(=O)c1ccc2c(c1)OCCO2] |

TABLE B-continued
| No. | Compound |
|---|---|
| 29A | 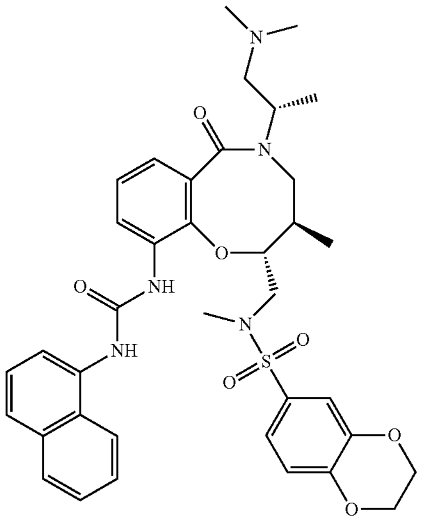 [SMILES: C[C@@H]1CN([C@@H](C)CN(C)C)C(=O)c2cccc(NC(=O)Nc3cccc4ccccc34)c2O[C@H]1CN(C)S(=O)(=O)c1ccc2c(c1)OCCO2] |
| 30A | 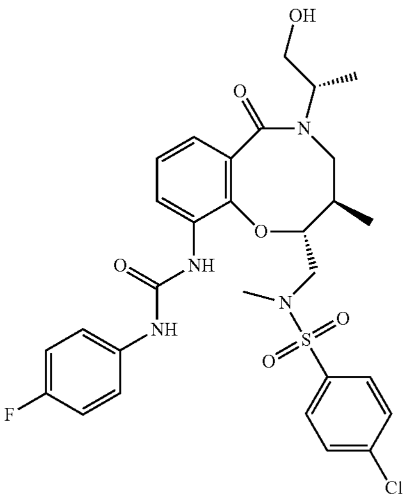 [SMILES: C[C@@H]1CN([C@@H](C)CO)C(=O)c2cccc(NC(=O)Nc3ccc(F)cc3)c2O[C@H]1CN(C)S(=O)(=O)c1ccc(Cl)cc1] |
| 31A | 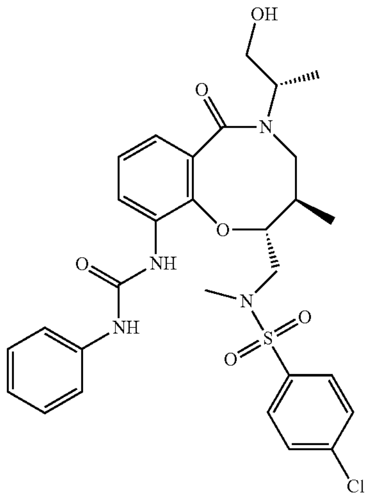 [SMILES: C[C@@H]1CN([C@@H](C)CO)C(=O)c2cccc(NC(=O)Nc3ccccc3)c2O[C@H]1CN(C)S(=O)(=O)c1ccc(Cl)cc1] |
TABLE B-continued
| No. | Compound |
|---|---|
| 31B | 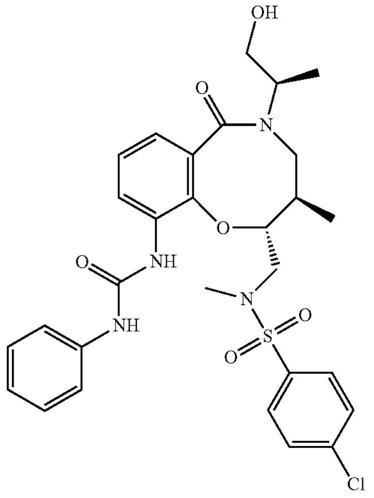 [SMILES: C[C@@H]1CN([C@H](C)CO)C(=O)c2cccc(NC(=O)Nc3ccccc3)c2O[C@H]1CN(C)S(=O)(=O)c1ccc(Cl)cc1] |
| 32A | 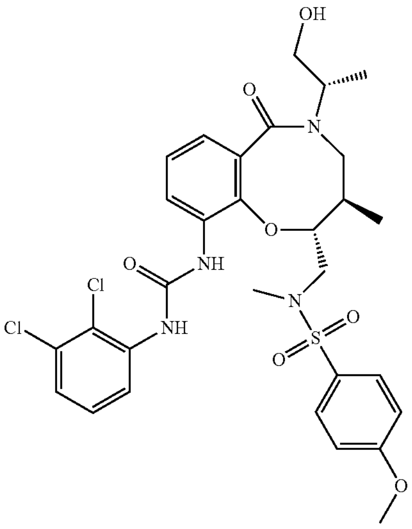 [SMILES: COc1ccc(S(=O)(=O)N(C)C[C@@H]2Oc3c(NC(=O)Nc4cccc(Cl)c4Cl)cccc3C(=O)N([C@@H](C)CO)C[C@H]2C)cc1] |
| 33A | 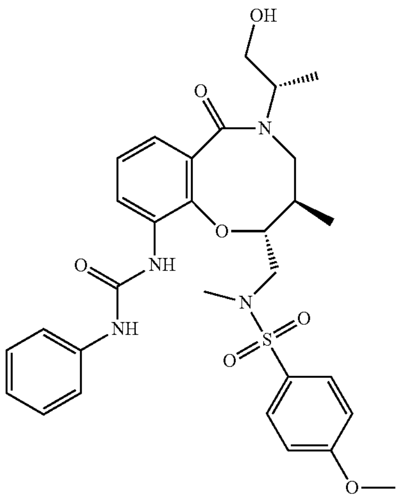 [SMILES: COc1ccc(S(=O)(=O)N(C)C[C@@H]2Oc3c(NC(=O)Nc4ccccc4)cccc3C(=O)N([C@@H](C)CO)C[C@H]2C)cc1] |

TABLE B-continued
| No. | Compound |
|---|---|
| 34A | 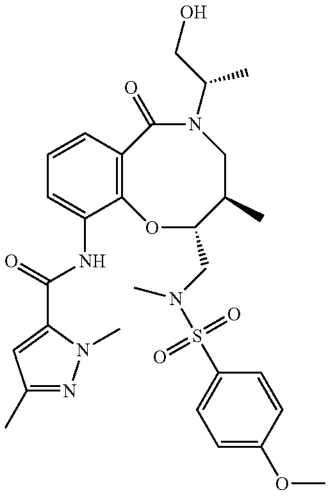 |
| 35A | 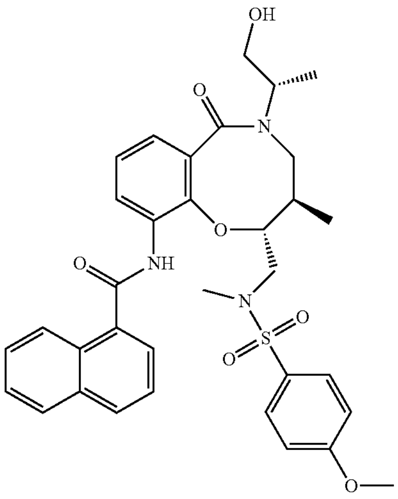 [SMILES: COc1ccc(S(=O)(=O)N(C)C[C@@H]2Oc3c(NC(=O)c4cccc5ccccc45)cccc3C(=O)N([C@@H](C)CO)C[C@H]2C)cc1] |
| 36A | 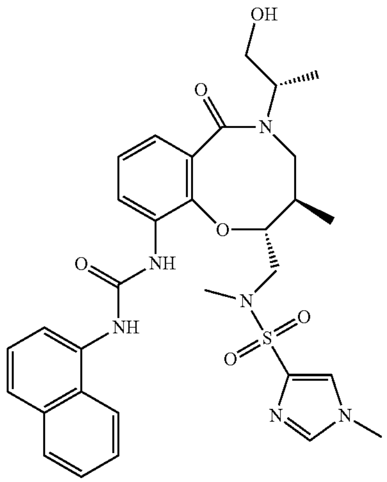 [SMILES: C[C@@H]1CN([C@@H](C)CO)C(=O)c2cccc(NC(=O)Nc3cccc4ccccc34)c2O[C@H]1CN(C)S(=O)(=O)c1cn(C)cn1] |
TABLE B-continued
| No. | Compound |
|---|---|
| 37A | 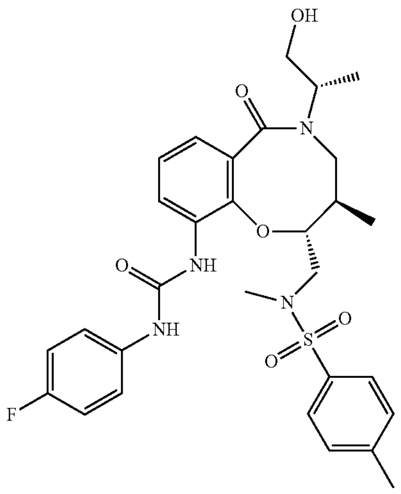 [SMILES: Cc1ccc(S(=O)(=O)N(C)C[C@@H]2Oc3c(NC(=O)Nc4ccc(F)cc4)cccc3C(=O)N([C@@H](C)CO)C[C@H]2C)cc1] |
| 37B | 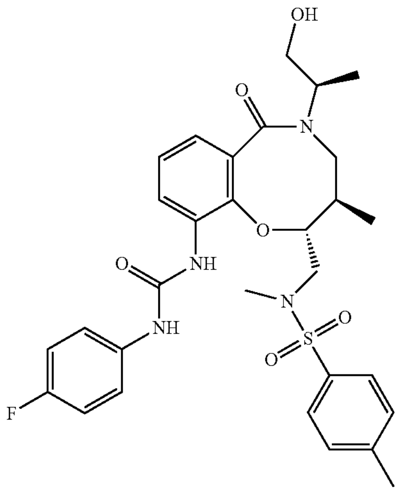 [SMILES: Cc1ccc(S(=O)(=O)N(C)C[C@@H]2Oc3c(NC(=O)Nc4ccc(F)cc4)cccc3C(=O)N([C@H](C)CO)C[C@H]2C)cc1] |
| 38A | 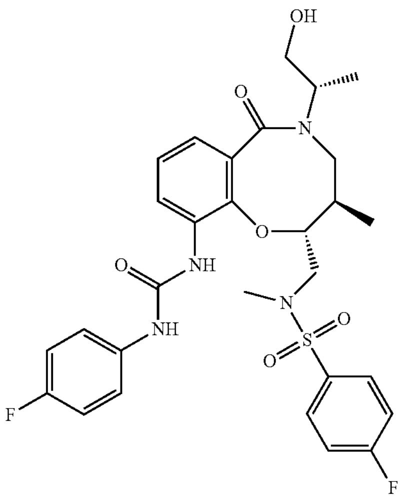 [SMILES: C[C@@H]1CN([C@@H](C)CO)C(=O)c2cccc(NC(=O)Nc3ccc(F)cc3)c2O[C@H]1CN(C)S(=O)(=O)c1ccc(F)cc1] |

TABLE B-continued
| No. | Compound |
|---|---|
| 39A | 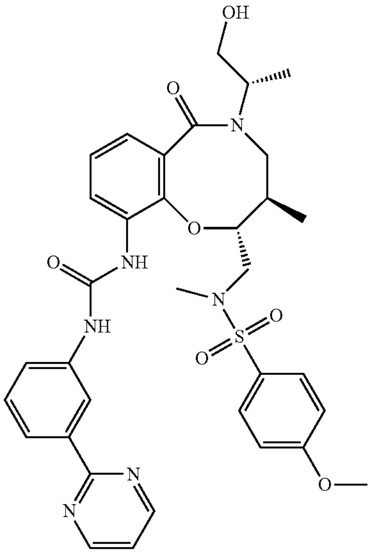 [SMILES: COc1ccc(S(=O)(=O)N(C)C[C@@H]2Oc3c(NC(=O)Nc4cccc(-c5ncccn5)c4)cccc3C(=O)N([C@@H](C)CO)C[C@H]2C)cc1] |
| 40A | 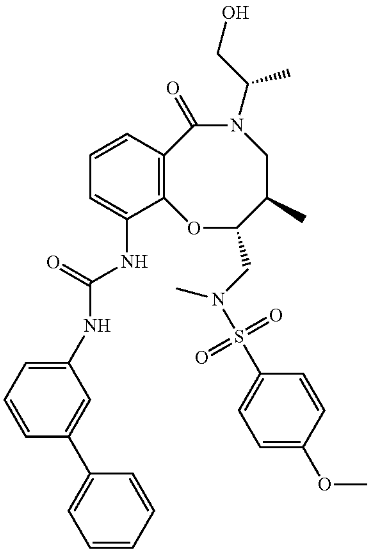 [SMILES: COc1ccc(S(=O)(=O)N(C)C[C@@H]2Oc3c(NC(=O)Nc4cccc(-c5ccccc5)c4)cccc3C(=O)N([C@@H](C)CO)C[C@H]2C)cc1] |
| 41A | 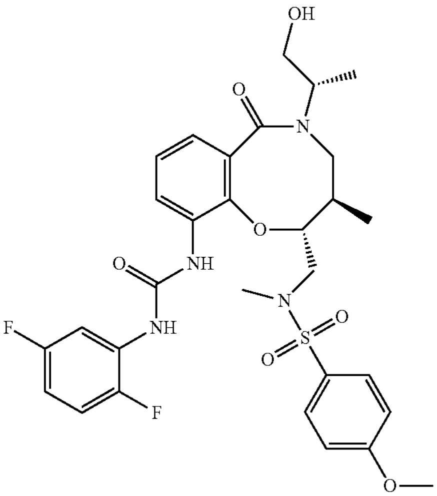 [SMILES: COc1ccc(S(=O)(=O)N(C)C[C@@H]2Oc3c(NC(=O)Nc4cc(F)ccc4F)cccc3C(=O)N([C@@H](C)CO)C[C@H]2C)cc1] |
| 42A | 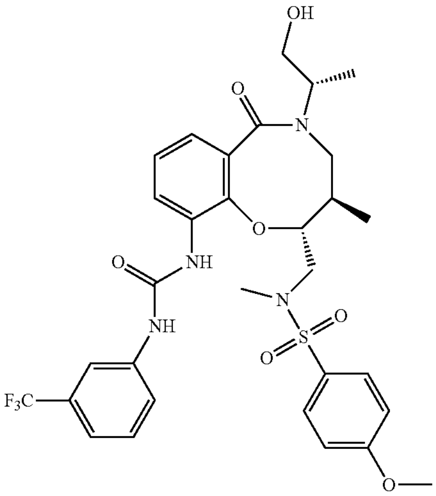 [SMILES: COc1ccc(S(=O)(=O)N(C)C[C@@H]2Oc3c(NC(=O)Nc4cccc(C(F)(F)F)c4)cccc3C(=O)N([C@@H](C)CO)C[C@H]2C)cc1] |
| 43A | 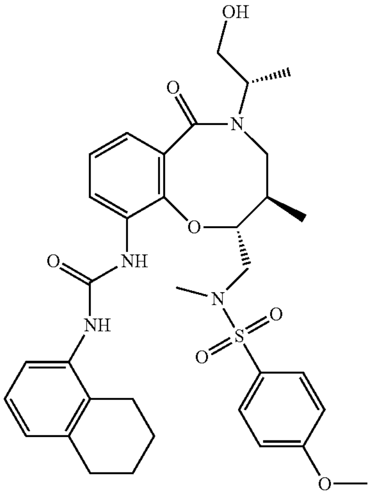 [SMILES: COc1ccc(S(=O)(=O)N(C)C[C@@H]2Oc3c(NC(=O)Nc4cccc5c4CCCC5)cccc3C(=O)N([C@@H](C)CO)C[C@H]2C)cc1] |
| 44A | 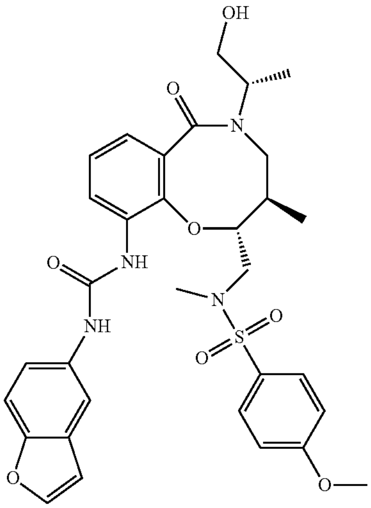 [SMILES: COc1ccc(S(=O)(=O)N(C)C[C@@H]2Oc3c(NC(=O)Nc4ccc5occc5c4)cccc3C(=O)N([C@@H](C)CO)C[C@H]2C)cc1] |

TABLE B-continued

| No. | Compound |
|---|---|
| 45A | 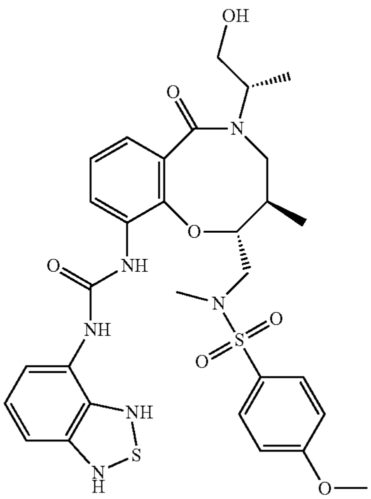 [SMILES: COc1ccc(S(=O)(=O)N(C)C[C@@H]2Oc3c(NC(=O)Nc4cccc5c4NSN5)cccc3C(=O)N([C@@H](C)CO)C[C@H]2C)cc1] |
| 46A | 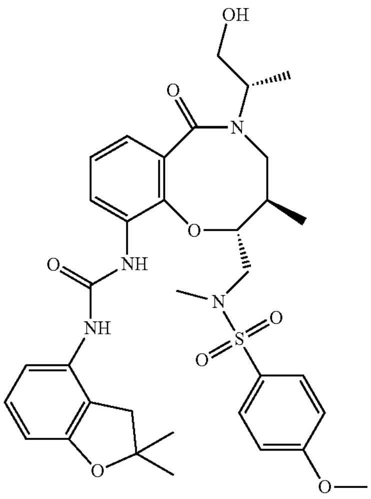 [SMILES: COc1ccc(S(=O)(=O)N(C)C[C@@H]2Oc3c(NC(=O)Nc4cccc5c4CC(C)(C)O5)cccc3C(=O)N([C@@H](C)CO)C[C@H]2C)cc1] |
| 47A | 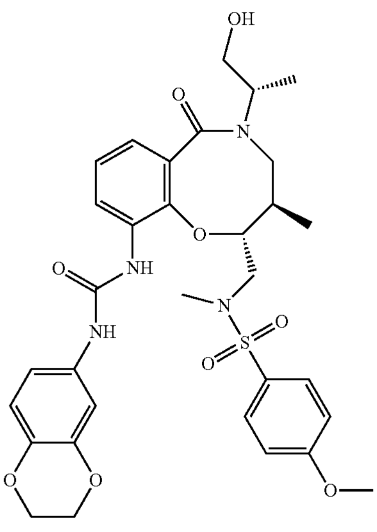 [SMILES: COc1ccc(S(=O)(=O)N(C)C[C@@H]2Oc3c(NC(=O)Nc4ccc5c(c4)OCCO5)cccc3C(=O)N([C@@H](C)CO)C[C@H]2C)cc1] |
| 48A | 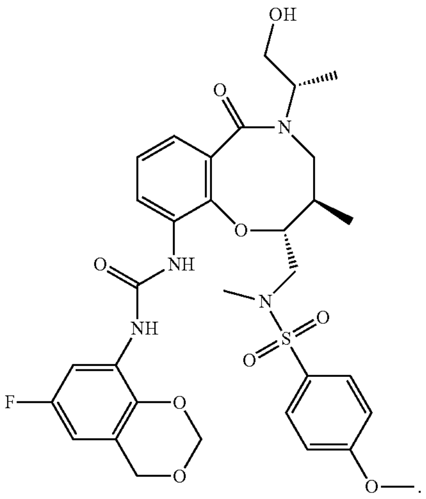 [SMILES: COc1ccc(S(=O)(=O)N(C)C[C@@H]2Oc3c(NC(=O)Nc4cc(F)cc5c4OCOC5)cccc3C(=O)N([C@@H](C)CO)C[C@H]2C)cc1] |

The invention further relates to the treatment of autoimmune diseases by the administration of a compound of Formula I. Compounds of Formula I can be useful for the treatment of autoimmune diseases including multiple sclerosis, Crohn's disease, lupus erythematosus, rheumatoid arthritis, osteoarthritis, psoriasis, ulcerative colitis, type-1 diabetes, pancreatitis, asthma, idiopathic thrombocytopenia purpura, uveitis, Guillain-Barre syndrome or myasthenia gravis. In a preferred embodiment a patient suffering from type-1 diabetes is treated with a compound of Formula I.

Without being bound by any theory the following postulated to relate the activity of the compounds of Formula I in autoimmune diseases. Human beta-cell apoptosis involves a complex set of signaling cascades initiated by IL-1β, IFN-γ, and TNF-α. IL-1β and TNF-α induce NF-κB expression, while downstream activation of gene expression is thought to occur through nitric oxide (NO) signaling, which both increases the endoplasmic reticulum stress-response pathway and decreases beta-cell function; this pathway works together with IFN-γ-induced STAT-1 signaling to effect beta-cell death. These effects of cytokines are beta cell-specific, and small-molecule suppressors should have little to no effect on other cell types in the pancreas. Small molecules that increase beta-cell survival in the presence of cytokines could be of potential clinical benefit to early-stage type 1 diabetic patients. A number of studies have described small molecules with protective effects in the presence of cytokines; most of these were discovered because of their nonspecific antioxidant or anti-inflammatory effects. Further, small-molecule inhibition of histone deacetylases (HDAC) with suberoylanilide hydroxamic acid (SAHA) or trichostatin A (TSA) can prevent cytokine-induced beta-cell death, presumably by decreasing NF-κB transactivation. Therefore, multiple mechanisms may serve to protect beta cells from cytokine-induced apoptosis. However, these compounds appeared to be somewhat toxic to these cells, as evidenced by a decrease in ATP even without cytokine treatment. Compound-1A inhibited cytokine-induced beta cell apoptosis with an $IC_{50}$ of 4.9 μM. Compound-21A exhibited an $IC_{50}$ of 770 nM. In addition to acting as a potent suppressor of cytokine-induced beta-cell apoptosis, Compound-21A decreased caspase-3/7 activity in INS-1E cells and restored glucose-stimulated insulin secretion (GSIS), showing improved beta-cell function, to nearly normal levels. It is postulated that this result is not merely due to an increase in cell viability for two reasons. First, the levels of insulin secreted in the presence of low-glucose (2 mM) conditions are nearly the same in all treatments. Second, we have observed other compounds that are capable of increasing ATP levels, but do not restore GSIS in this assay. Thus, Compound-21A is likely suppressing beta-cell apoptosis and restoring important physiological beta-cell function. An important compound for this process will be active in human cells. To that end, we treated dissociated human islets with the same combination of cytokines. Independently, we had developed a dissociated human islet cell-culture system to study beta-cell proliferation. In this system, intact human islets are gently dissociated, and seeded onto 96- or 384-well plates coated with extracellular matrix derived from the HTB-9 human bladder carcinoma cell line. We observed induction of apoptosis after a six-day treatment; these results are consistent with previous reports in human dissociated islets. Six-day treatment induced caspase-3/7 activity by approximately 60%; this effect was abolished by co-incubation with Compound-21A. Because of the use of dissociated islets and a whole-well readout of caspase activity, it cannot be certain that only beta cells are undergoing apoptosis; however, based on previous results in the literature, beta cells may constitute the majority of the apoptotic effect.

The invention further relates to a method of treating a BCL-2 related disease or disorder by administering a compound of Formula I to a subject in need thereof. In one embodiment, the BCL-2 mediated disease or disorder is a cell proliferative disorder. In a preferred embodiment, the cell proliferative disorder is selected from breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In a preferred embodiment, the cell proliferative disorder is selected from the group consisting of papilloma, blastoglioma, Kaposi's sarcoma, melanoma, lung cancer, ovarian cancer, prostate cancer, squamous cell carcinoma, astrocytoma, head cancer, neck cancer, bladder cancer, breast cancer, lung cancer, colorectal cancer, thyroid cancer, pancreatic cancer, gastric cancer, hepatocellular carcinoma, leukemia, lymphoma, Hodgkin's disease and Burkitt's disease.

In one embodiment, the invention relates to a composition comprising a compound of Formula I and another BCL-2 inhibitor. In a preferred embodiment, the composition comprises a compound of Formula I and a second compound selected from ABT-263, ABT-737, gossypol, chelerythrine chloride, apogossypolone, antimycin A, TW-37, HA14-1, obatoclax (GX15-070), ApoG2, NMB and TM12-06. In a more preferred embodiment, the second compound is ABT-737.

In one embodiment, the invention relates to a method of treating a deubiquitinase related disease or disorder comprising administering a compound of Formula I to a subject in need thereof. In one embodiment, the deubiquitinase related disease or disorder is selected from inflammation, cell proliferative disorder, macular degeneration and diabetic retinopathy, Alzheimer's, atherosclerosis, psoriasis, rheumatoid arthritis and endometriosis. In one embodiment the disease or disorder is a cell proliferative disorder, preferably cancer.

In one embodiment, the invention relates to the treatment of a disease or disorder mediated by the abnormal or aberrant expression of one or more gene or gene product selected from Table 1.

TABLE 1

| Accession No. | Description |
|---|---|
| 1370202_at | HRAS like suppressor 3, Hrasls3 |
| 1369268_at | activating transcription factor 3, Atf3 |
| 1372013_at | interferon induced transmembrane protein 1 (predicted), Ifitm1_predicted |
| 1377156_at | similar to Transcription factor 7-like 2 (HMG box transcription factor 4) (T-cell-specific transcription factor 4) (TCF-4) (hTCF-4), LOC683733 |
| 1384391_at | retinol dehydrogenase 10 (all-trans), Rdh10 |
| 1373923_at | Retinol dehydrogenase 10 (all-trans), Rdh10 |
| 1368868_at | A kinase (PRKA) anchor protein (gravin) 12, Akap12 |
| 1393351_at | Retinol dehydrogenase 10 (all-trans), Rdh10 |
| 1367918_at | fasciculation and elongation protein zeta 1 (zygin I), Fez1 |
| 1368869_at | A kinase (PRKA) anchor protein (gravin) 12, Akap12 |
| 1388102_at | leukotriene B4 12-hydroxydehydrogenase, Ltb4dh |
| 1392547_at | hypothetical LOC302884, MGC105649 |
| 1396327_at | cytochrome P450, family 2, subfamily j, polypeptide 10 (predicted), Cyp2j10_predicted |
| 1368751_at | potassium voltage-gated channel, delayed-rectifier, subfamily S, member 3, Kcns3 |
| 1373309_at | transmembrane protein 86A (predicted), Tmem86a_predicted |
| 1368375_a_at | interleukin 15, Il15 |
| 1370427_at | platelet derived growth factor, alpha, Pdgfa |
| 1388502_at | inositol polyphosphate-5-phosphatase B, Inpp5b |
| 1372111_at | met proto-oncogene /// caveolin, caveolae protein 1 /// wingless-related MMTV integration site 2 /// ankyrin repeat, SAM and basic leucine zipper domain containing 1 /// cortactin binding protein 2 /// suppression of tumorigenicity 7 /// caveolin 2, Asz1 /// Cav1 /// Cav2 /// Cttnbp2 /// Met /// ST7 /// Wnt2 |
| 1374469_at | Transcribed locus, strongly similar to XP_578186.2 PREDICTED: similar to oxidation resistance 1 [*Rattus norvegicus*], --- |
| 1378679_at | ubiquitin specific peptidase 25, Usp25 |
| 1379375_at | Platelet derived growth factor, alpha, Pdgfa |
| 1372302_at | family with sequence similarity 82, member C, Fam82c |
| 1372182_at | phosphofructokinase, platelet, Pfkp |
| 1386979_at | developmentally regulated protein TPO1, Tpo1 |
| 1390847_at | transmembrane protein 86A (predicted), Tmem86a_predicted |
| 1390226_at | similar to hypothetical protein LOC340061 (predicted), RGD1562552_predicted |
| 1374519_at | dedicator of cytokinesis 7, Dock7 |
| 1371033_at | transporter 1, ATP-binding cassette, sub-family B (MDR/TAP) /// transporter 2, ATP-binding cassette, sub-family B (MDR/TAP) /// proteosome (prosome, macropain) subunit, beta type 9 /// similar to butyrophilin-like 8 (predicted) /// RT1 class II, locus Da /// RT1 class II, locus Db1 /// major histocompatibility complex, class II, DM beta /// major histocompatibility complex, class II, DM alpha /// RT1 class II, locus Ba /// RT1 class II, locus Bb /// RT1 class II, locus DOb /// butyrophilin-like 4 /// butyrophilin-like 5 /// butyrophilin-like 3 /// Tesb pseudo-gene, Btnl3 /// Btnl4 /// Btnl5 /// Hla-dma /// Hla-dmb /// |

TABLE 1-continued

| Accession No. | Description |
|---|---|
| | Psmb9 /// RGD1562488_predicted /// RT1-Ba /// RT1-Bb /// RT1-Da /// RT1-Db1 /// RT1-DOb /// Tap1 /// Tap2 /// Tesb |
| 1385502_at | Tripartite motif protein 21 (predicted), Trim21_predicted |
| 1371491_at | Notch gene homolog 1 (*Drosophila*), Notch1 |
| 1373911_at | periostin, osteoblast specific factor (predicted), Postn_predicted |
| 1393806_at | MANSC domain containing 1, Mansc1 |
| 1373912_at | Ectonucleotide pyrophosphatase/phosphodiesterase 4 (predicted), Enpp4_predicted |
| 1388936_at | cadherin 11, Cdh11 |
| 1374404_at | Jun oncogene, Jun |
| 1382074_at | ring finger protein 19B, Rnf19b |
| 1370974_at | vacuolar protein sorting 54 (yeast), Vps54 |
| 1368144_at | regulator of G-protein signaling 2, Rgs2 |
| 1369788_s_at | Jun oncogene, Jun |
| 1389528_s_at | Jun oncogene, Jun |
| 1369519_at | endothelin 1, Edn1 |
| 1395124_at | tryptophanyl-tRNA synthetase, Wars |
| 1376977_at | Prostaglandin E receptor 3 (subtype EP3), Ptger3 |
| 1373961_at | similar to 4930453N24Rik protein, MGC95208 |
| 1387398_at | protein kinase inhibitor, alpha, Pkia |
| 1389365_at | similar to CG3740-PA, LOC690000 |
| 1368856_at | Janus kinase 2, Jak2 |
| 1374499_at | CDNA clone MGC: 187619 IMAGE: 8367117, --- |
| 1377893_at | similar to CG3740-PA, LOC690000 |
| 1387074_at | regulator of G-protein signaling 2, Rgs2 |
| 1372602_at | starch binding domain 1, Stbd1 |
| 1395135_at | Williams Beuren syndrome chromosome region 27, Wbscr27 |
| 1398840_at | vesicle-associated membrane protein 5, Vamp5 |
| 1387800_at | Fas death domain-associated protein, Daxx |
| 1373761_at | similar to Protein FAM60A (Tera protein), LOC686611 |
| 1386998_at | aldolase C, Aldoc |
| 1384457_at | similar to Fbxw17 protein (predicted), RGD1566133_predicted |
| 1371071_at | guanine nucleotide binding protein, beta 4, Gnb4 |
| 1369319_at | ADP-ribosylation factor-like 6 interacting protein 5, Arl6ip5 |
| 1385210_at | dedicator of cytokinesis 5 (predicted), Dock5_predicted |
| 1388469_at | Insulin-like growth factor I mRNA, 3' end of mRNA, --- |
| 1385961_at | Kruppel-like factor 5, Klf5 |
| 1394077_at | Rho family GTPase 3, Rnd3 |
| 1376026_at | downstream neighbor of SON, Donson |
| 1368111_at | ankyrin repeat and BTB (POZ) domain containing 2, Abtb2 |
| 1375870_a_at | RNA binding motif, single stranded interacting protein 1, Rbms1 |
| 1375739_at | EH-domain containing 4, Ehd4 |
| 1383915_at | hypothetical protein LOC686120, LOC686120 |
| 1390507_at | interferon stimulated exonuclease 20, Isg20 |
| 1373143_at | similar to hypothetical protein FLJ10652, RGD1309621 |
| 1379558_at | Similar to zinc finger protein 748 isoform 2, LOC680222 |
| 1380110_at | Janus kinase 2, Jak2 |
| 1389263_at | retinoic acid induced 14, Rai14 |
| 1373412_at | 5'-nucleotidase, cytosolic III (predicted), Nt5c3_predicted |
| 1387851_at | phosphotriesterase related, Pter |
| 1387035_a_at | Rho GTPase activating protein 17, Arhgap17 |
| 1377663_at | Rho family GTPase 3, Rnd3 |
| 1368321_at | early growth response 1, Egr1 |
| 1380513_at | RNA polymerase II associated protein 2, Rpap2 |
| 1390237_at | translocase of inner mitochondrial membrane 8 homolog a1 (yeast), Timm8a1 |
| 1368571_at | CAP-GLY domain containing linker protein 2, Clip2 |
| 1372056_at | CKLF-like MARVEL transmembrane domain containing 6, Cmtm6 |
| 1368982_at | protein kinase inhibitor, alpha, Pkia |
| 1388574_at | tryptophanyl-tRNA synthetase, Wars |
| 1373775_at | NEDD8 ultimate buster-1, Nub1 |
| 1383013_at | Kruppel-like factor 13, Klf13 |
| 1389732_at | Similar to CG4025-PA, LOC679937 |
| 1387294_at | SH3-domain binding protein 5 (BTK-associated), Sh3bp5 |
| 1385294_at | ets variant gene 6 (TEL oncogene), Etv6 |
| 1388027_a_at | reticulon 4, Rtn4 |
| 1370428_x_at | RT1 class Ib, locus Aw2 /// RT1 class Ia, locus A1 /// RT1 class Ia, locus A2 /// RT1 class Ib, locus C1 /// RT1 class II, locus DOa /// RT1 class II, locus Ha /// TAP binding protein /// discoidin domain receptor family, member 1 /// leucocyte specific transcript 1 /// Fas death domain-associated protein /// UDP-Gal:betaGlcNAc beta 1,3-galactosyltransferase, polypeptide 4 /// synaptic Ras GTPase activating protein 1 homolog (rat) /// general transcription factor II H, polypeptide 4 /// procollagen, type XI, alpha 2 /// RT1 class I, locus Ke4 /// RAB2, member RAS oncogene family-like /// PHD finger protein 1 /// zinc finger and BTB domain containing 9 /// POU domain, class 5, transcription factor 1 /// valyl-tRNA synthetase 2-like /// RT1 class I, CE12 /// RT1 class I, CE1 /// RT1 class I, CE5 /// RT1 class I, A3 /// WD repeat domain 46 /// MHC class II region expressed gene KE2 /// zinc finger protein 297 /// lymphotoxin B /// ATPase, H+ transporting, V1 subunit G isoform 2 /// RT1 class I, CE7 /// transcription factor 19 /// HCR (a-helix coiled-coil rod homolog) /// psoriasis susceptibility 1 candidate 2 (human) /// corneodesmosin /// RT1 class I, CE14 /// RT1 class I, CE2 /// RT1 class I, CE4 /// RT1 class I, CE15 /// RT1 class I, CE13 /// RT1 class I, CE11 /// RT1 class I, CE10 /// RT1 class I, CE3 /// RT1 class I, CE16 /// similar to corneodesmosin, Atp6v1g2 /// B3galt4 /// Cdsn /// Col11a2 /// Daxx /// Ddr1 /// Gtf2h4 /// Hcr /// Ke2 /// LOC682408 /// Lst1 /// Ltb /// Phf1 /// Pou5f1 /// Psors1c2 /// Rab2l /// RT1-A1 /// RT1-A2 /// RT1-A3 /// RT1-Aw2 /// RT1-CE1 /// RT1-CE10 /// RT1-CE11 /// RT1-CE12 ///RT1-CE13 /// RT1-CE14 /// RT1-CE15 /// RT1-CE16 /// RT1-CE2 /// RT1-CE3 /// RT1-CE4 /// RT1-CE5 /// RT1-CE7 /// RT1-Cl /// RT1-DOa /// RT1-Ha /// RT1-Ke4 /// Syngap1 /// Tapbp /// Tcf19 /// Vars2l /// Wdr46 /// Zbtb9 /// Zfp297 |
| 1393217_at | ATP-binding cassette, sub-family G (WHITE), member 3-like 1, Abcg3l1 |
| 1371049_at | dihydropyrimidinase-like 4, Dpysl4 |
| 1377387_a_at | Transcribed locus, strongly similar to NP_079738.2 endothelin converting enzyme 2 isoform c [*Mus musculus*], --- |
| 1385658_at | zinc finger protein 313, Zfp313 |
| 1395297_at | similar to hypothetical protein FLJ10652, RGD1309621 |
| 1374387_at | ADP-ribosylation factor-like 6 interacting protein 5, Arl6ip5 |
| 1369633_at | chemokine (C—X—C motif) ligand 12, Cxcl12 |
| 1389014_at | pre-B-cell colony enhancing factor 1, Pbef1 |
| 1387257_at | secretin, Sct |
| 1387646_a_at | Max protein, Max |
| 1370463_x_at | RT1 class I, CE16, RT1-CE16 |
| 1381567_at | zinc finger with UFM1-specific peptidase domain, Zufsp |
| 1368181_at | methylenetetrahydrofolate dehydrogenase (NADP+ dependent), methenyltetrahydrofolate cyclohydrolase, formyltetrahydrofolate synthase, Mthfd1 |
| 1374678_at | sema domain, immunoglobulin domain (Ig), transmembrane domain (TM) and short cytoplasmic domain, (semaphorin) 4B, Sema4b |
| 1382158_at | zinc finger protein 202, Zfp202 |
| 1379450_at | CTTNBP2 N-terminal like (predicted), Cttnbp2nl_predicted |
| 1373831_at | hypothetical protein LOC619574, LOC619574 |
| 1377439_at | similar to hypothetical protein FLJ13231 (predicted) /// hypothetical protein LOC679830, LOC679830 /// RGD1310081_predicted |
| 1388583_at | chemokine (C—X—C motif) ligand 12, Cxcl12 |
| 1372473_at | tight junction protein 1 (predicted), Tjp1_predicted |
| 1376440_at | ring finger protein 139 (predicted), Rnf139_predicted |
| 1382873_at | CTTNBP2 N-terminal like (predicted), Cttnbp2nl_predicted |
| 1373830_at | hypothetical protein LOC619574, LOC619574 |
| 1396262_at | pre-B-cell colony enhancing factor 1, Pbef1 |
| 1372106_at | EH-domain containing 4, Ehd4 |
| 1376082_at | ecotropic viral integration site 1 (predicted), Evi1_predicted |
| 1390036_at | solute carrier family 16 (monocarboxylic acid transporters), member 6, Slc16a6 |
| 1372270_at | dolichyl-phosphate (UDP-N-acetylglucosamine) N-acetylglucosaminephosphotransferase 1 (GlcNAc-1-P transferase), Dpagt1 |
| 1393234_at | Transcribed locus, strongly similar to NP_001106215.1 Rho guanine nucleotide exchange factor (GEF) 16 [*Mus musculus*], --- |
| 1379287_at | cylindromatosis (turban tumor syndrome), Cyld |
| 1372695_at | Transcribed locus, strongly similar to NP_081678.1 fibronectin type III domain containing 5 [*Mus musculus*], --- |

TABLE 1-continued

| Accession No. | Description |
|---|---|
| 1382277_at | lymphocyte antigen 96, Ly96 |
| 1387265_at | diacylglycerol kinase, gamma, Dgkg |
| 1373669_at | glucosamine-6-phosphate deaminase 2 (predicted), Gnpda2_predicted |
| 1375216_at | poliovirus receptor-related 2, Pvrl2 |
| 1372846_at | cytochrome b, ascorbate dependent 3, Cybasc3 |
| 1379561_at | ATPase family, AAA domain containing 1, Atad1 |
| 1375177_at | Kruppel-like factor 13, Klf13 |
| 1395248_at | ER degradation enhancer, mannosidase alpha-like 1, Edem1 |
| 1383829_at | bobby sox homolog (*Drosophila*) (predicted), Bbx_predicted |
| 1372895_at | similar to RIKEN cDNA 5730469M10, RGD1309676 |
| 1380650_at | TRIO and F-actin binding protein, Triobp |
| 1393641_at | B-cell linker, Blnk |
| 1367758_at | alpha-fetoprotein, Afp |
| 1399167_a_at | growth factor receptor bound protein 2-associated protein 1 (predicted), Gab1_predicted |
| 1368274_at | drebrin-like, Dbnl |
| 1389059_at | Transcribed locus, weakly similar to XP_001250613.1 PREDICTED: hypothetical protein [*Bos taurus*], --- |
| 1385411_at | ubiquitin specific protease 43, rCG_32844 |
| 1384186_at | ER degradation enhancer, mannosidase alpha-like 1, Edem1 |
| 1371624_at | zinc finger CCCH-type containing 7B (predicted), Zc3h7b_predicted |
| 1375934_at | ring finger protein 128 /// hypothetical protein LOC680663, LOC680663 /// Rnf128 |
| 1389681_at | Transcribed locus, moderately similar to NP_002847.1 poliovirus receptor related 2 isoform alpha precursor [*Homo sapiens*], --- |
| 1389164_at | hect domain and RLD 3 (predicted), Herc3_predicted |
| 1375582_at | zinc finger homeodomain 4 (predicted), Zfhx4_predicted |
| 1376766_at | formin-like 1 (predicted), Fmnl1_predicted |
| 1386346_at | transmembrane protein 19, Tmem19 |
| 1388195_at | CUG triplet repeat, RNA binding protein 2, Cugbp2 |
| 1383554_at | ring finger protein 128 /// hypothetical protein LOC680663, LOC680663 /// Rnf128 |
| 1391211_at | Atpase, class VI, type 11C (predicted), Atp11c_predicted |
| 1388071_x_at | RT1 class Ib, locus Aw2, RT1-Aw2 |
| 1383662_at | hypothetical protein LOC500956, LOC500956 |
| 1388791_at | similar to 2810022L02Rik protein, RGD1309930 |
| 1387180_at | interleukin 1 receptor, type II, Il1r2 |
| 1373136_at | zinc finger with UFM1-specific peptidase domain, Zufsp |
| 1373913_at | polyribonucleotide nucleotidyltransferase 1, Pnpt1 |
| 1369562_at | hippocalcin-like 1, Hpcal1 |
| 1371662_at | lysyl-tRNA synthetase, Kars |
| 1392658_at | Similar to transcription elongation factor A 1 isoform 2, LOC498453 |
| 1370972_x_at | RT1 class I, CE5, RT1-CE5 |
| 1388409_at | zinc finger CCCH-type containing 7B (predicted), Zc3h7b_predicted |
| 1372090_at | Max protein, Max |
| 1392958_at | cylindromatosis (turban tumor syndrome), Cyld |
| 1369557_at | caspase 7, Casp7 |
| 1376117_at | solute carrier family 44, member 4, Slc44a4 |
| 1372533_at | ER degradation enhancer, mannosidase alpha-like 1, Edem1 |
| 1394842_at | transmembrane protein 19, Tmem19 |
| 1399153_at | RAB5B, member RAS oncogene family (predicted), Rab5b_predicted |
| 1369197_at | apoptotic peptidase activating factor 1, Apaf1 |
| 1391679_at | hypothetical protein LOC691083, LOC691083 |
| 1375955_at | zinc finger protein 313, Zfp313 |
| 1383551_at | 2,3-bisphosphoglycerate mutase, Bpgm |
| 1373501_at | NIMA (never in mitosis gene a)-related expressed kinase 7, Nek7 |
| 1398983_at | mitochondrial ribosomal protein L30 (predicted), Mrpl30_predicted |
| 1389387_at | similar to Proteasome inhibitor PI31 subunit, LOC682071 /// LOC689852 |
| 1373065_at | protein tyrosine phosphatase, non-receptor type 18, Ptpn18 |
| 1377000_at | WAS protein homology region 2 domain containing 1, Whdc1 |
| 1379256_at | similar to RIKEN cDNA 1810030O07 (predicted), RGD1565685_predicted |
| 1374400_at | EFR3 homolog A (*S. cerevisiae*), Efr3a |

TABLE 1-continued

| Accession No. | Description |
|---|---|
| 1373520_at | CDNA clone IMAGE: 7367270, --- |
| 1372865_at | zinc finger protein 364 (predicted), Zfp364_predicted |
| 1392978_at | solute carrier family 25, member 28, Slc25a28 |
| 1372211_at | v-maf musculoaponeurotic fibrosarcoma oncogene family, protein K (avian), Mafk |
| 1379957_at | schlafen 8, Slfn8 |
| 1371774_at | spermidine/spermine N1-acetyl transferase 1, Sat1 |
| 1369067_at | nuclear receptor subfamily 4, group A, member 3, Nr4a3 |
| 1387131_at | serine (or cysteine) peptidase inhibitor, clade I, member 1, Serpini1 |
| 1375853_at | Similar to CG13957-PA (predicted), RGD1309995_predicted |
| 1377970_at | poly (ADP-ribose) polymerase family, member 8, Parp8 |
| 1388823_at | RAB5B, member RAS oncogene family (predicted), Rab5b_predicted |
| 1389053_at | Similar to hypothetical protein FLJ20627 (predicted), RGD1309546_predicted |
| 1371525_at | solute carrier family 12, member 7, Slc12a7 |
| 1367710_at | proteasome (prosome, macropain) 28 subunit, beta, Psme2 |
| 1391442_at | EH-domain containing 3, Ehd3 |
| 1392838_at | similar to CG13957-PA (predicted), RGD1309995_predicted |
| 1387897_at | 2',3'-cyclic nucleotide 3' phosphodiesterase, Cnp |
| 1376835_at | Solute carrier family 35, member B2, Slc35b2 |
| 1380121_at | NIMA (never in mitosis gene a)-related expressed kinase 7, Nek7 |
| 1388768_at | small G protein signaling modulator 2, Sgsm2 |
| 1368476_at | nuclear receptor subfamily 3, group C, member 2, Nr3c2 |
| 1367746_a_at | flotillin 2, Flot2 |
| 1370946_at | nuclear factor I/X, Nfix |
| 1393389_at | nuclear receptor subfamily 4, group A, member 3, Nr4a3 |
| 1368273_at | mitogen-activated protein kinase 6, Mapk6 |
| 1388544_at | 2,3-bisphosphoglycerate mutase, Bpgm |
| 1375447_at | GTP binding protein 1 (predicted), Gtpbp1_predicted |
| 1399063_at | ZUBR1, Rbaf600 |
| 1388233_at | cytokine inducible SH2-containing protein, Cish |
| 1367663_at | proteasome (prosome, macropain) 28 subunit, alpha, Psme1 |
| 1380001_at | pinin, Pnn |
| 1390859_at | Nedd4 binding protein 1, N4bp1 |
| 1374939_at | cytoplasmic FMR1 interacting protein 2 (predicted), Cyfip2_predicted |
| 1395336_at | Similar to 2810022L02Rik protein, RGD1309930 |
| 1383768_at | ELAV (embryonic lethal, abnormal vision, *Drosophila*)-like 2 (Hu antigen B), Elavl2 |
| 1368813_at | CCAAT/enhancer binding protein (C/EBP), delta, Cebpd |
| 1376810_at | M-phase phosphoprotein 8 /// poly (ADP-ribose) polymerase family, member 4, Mphosph8 /// Parp4 |
| 1369559_a_at | CD47 antigen (Rh-related antigen, integrin-associated signal transducer), Cd47 |
| 1386922_at | carbonic anhydrase 2, Ca2 |
| 1383616_at | interleukin 10 receptor, beta, Il10rb |
| 1368248_at | CDP-diacylglycerol synthase 1, Cds1 |
| 1368158_at | sec1 family domain containing 1, Scfd1 |
| 1369654_at | protein kinase, AMP-activated, alpha 2 catalytic subunit, Prkaa2 |
| 1392077_at | putative C11orf8 homolog (human), C11orf8h |
| 1376692_at | homeodomain interacting protein kinase 2 (predicted), Hipk2_predicted |
| 1372179_at | hippocalcin-like 1, Hpcal1 |
| 1369590_a_at | DNA-damage inducible transcript 3, Ddit3 |
| 1372101_at | phosphatidic acid phosphatase type 2B, Ppap2b |
| 1380867_a_at | pleckstrin homology domain containing, family M (with RUN domain) member 1, Plekhm1 |
| 1371509_at | transforming growth factor beta regulated gene 1, Tbrg1 |
| 1375677_at | transducer of ERBB2, 2, Tob2 |
| 1391222_at | Nedd4 binding protein 1, N4bp1 |
| 1383369_at | tripartite motif-containing 26, Trim26 |
| 1367986_at | prostaglandin F2 receptor negative regulator, Ptgfrn |
| 1393359_at | adaptor-related protein complex 3, beta 2 subunit (predicted), Ap3b2_predicted |
| 1371925_at | ATPase type 13A1 (predicted), Atp13a1_predicted |
| 1373091_at | pleiomorphic adenoma gene-like 2 (predicted), Plagl2_predicted |
| 1368503_at | GTP cyclohydrolase 1, Gch1 |
| 1367733_at | carbonic anhydrase 2, Ca2 |
| 1384244_at | hydroxysteroid dehydrogenase like 2, Hsdl2 |
| 1389282_at | Integrin alpha 3 (predicted), Itga3_predicted |
| 1380964_at | dystrobrevin alpha (predicted), Dtna_predicted |

TABLE 1-continued

| Accession No. | Description |
|---|---|
| 1393253_at | zinc finger protein 365, Zfp365 |
| 1388798_at | ubiquitin-conjugating enzyme E2E 2 (UBC4/5 homolog, yeast), Ube2e2 |
| 1392107_at | strawberry notch homolog 2 (*Drosophila*), Sbno2 |
| 1386976_at | CD82 antigen, Cd82 |
| 1376737_at | hypothetical protein LOC690243, LOC690243 |
| 1372009_at | tyrosyl-tRNA synthetase, Yars |
| 1399161_a_at | type 1 tumor necrosis factor receptor shedding aminopeptidase regulator, Arts1 |
| 1380582_at | colony stimulating factor 1 (macrophage), Csf1 |
| 1378293_at | tripartite motif-containing 26, Trim26 |
| 1395426_at | ubiquitin-conjugating enzyme E2 variant 1 (predicted), Ube2v1_predicted |
| 1377759_at | BH3 interacting domain death agonist, Bid |
| 1383679_at | ring finger protein 31 (predicted), Rnf31_predicted |
| 1368716_at | protein phosphatase 1, regulatory (inhibitor) subunit 14c, Ppp1r14c |
| 1392518_at | Similar to Protein C22orf5, RGD1306591 |
| 1386926_at | acyl-CoA synthetase long-chain family member 5, Acsl5 |
| 1375006_at | CDNA clone IMAGE: 7318427, --- |
| 1389913_at | leucine rich repeat (in FLII) interacting protein 1, Lrrfip1 |
| 1373588_at | FERM domain containing 8, Frmd8 |
| 1382710_at | Ectodermal-neural cortex 1, Enc1 |
| 1371550_at | TSC22 domain family, member 4, Tsc22d4 |
| 1368679_a_at | Yamaguchi sarcoma viral (v-yes-1) oncogene homolog, Lyn |
| 1389331_at | CDNA clone IMAGE: 7313169, --- |
| 1381570_at | T-cell activation NFKB-like protein, Ta-nfkbh |
| 1367696_at | interferon induced transmembrane protein 2, Ifitm2 |
| 1396278_at | sorting nexin 11, Snx11 |
| 1393703_at | human immunodeficiency virus type I enhancer binding protein 3 (predicted), Hivep3_predicted |
| 1379460_at | SH3-domain GRB2-like (endophilin) interacting protein 1, Sgip1 |
| 1371005_at | ATP-binding cassette, sub-family C (CFTR/MRP), member 1, Abcc1 |
| 1368928_at | tripartite motif-containing 3, Trim3 |
| 1371531_at | similar to mammalian retrotransposon derived 8b, LOC678880 |
| 1368674_at | liver glycogen phosphorylase, Pygl |
| 1368896_at | MAD homolog 7 (*Drosophila*), Smad7 |
| 1387221_at | GTP cyclohydrolase 1, Gch1 |
| 1385361_at | ATPase, class V, type 10A, Atp10a |
| 1376174_at | serine (or cysteine) peptidase inhibitor, clade A (alpha-1 antiproteinase, antitrypsin), member 11, Serpina11 |
| 1390423_at | MYC binding protein 2, Mycbp2 |
| 1372869_at | similar to isopentenyl diphosphate delta-isomerase type 2 (predicted) /// similar to Nucleolar GTP-binding protein 1 (Chronic renal failure gene protein) (GTP-binding protein NGB), LOC689842 /// RGD1560805_predicted |
| 1391897_at | RAB GTPase activating protein 1-like, Rabgap1l |
| 1371825_at | small nuclear RNA activating complex, polypeptide 2, Snapc2 |
| 1382775_at | ryanodine receptor 2, cardiac, Ryr2 |
| 1385758_at | SAPS domain family, member 1 (predicted), Saps1_predicted |
| 1382029_at | similar to CDNA sequence BC017647 (predicted), RGD1566149_predicted |
| 1371528_at | FK506 binding protein 8, Fkbp8 |
| 1367938_at | UDP-glucose dehydrogenase, Ugdh |
| 1371659_at | ras homolog gene family, member C (predicted), Rhoc_predicted |
| 1371731_at | Similar to Coatomer gamma-2 subunit (Gamma-2 coat protein) (Gamma-2 COP) (predicted), RGD1566215_predicted |
| 1373748_at | PDZ domain containing RING finger 3 (predicted), Pdzrn3_predicted |
| 1374035_at | rad and gem related GTP binding protein 2, Rem2 |
| 1368983_at | heparin-binding EGF-like growth factor, Hbegf |
| 1375861_at | nucleosome assembly protein 1-like 5, Nap1l5 |
| 1394022_at | inhibitor of DNA binding 4, Id4 |
| 1370606_at | purinergic receptor P2Y, G-protein coupled 1, P2ry1 |
| 1368641_at | wingless-related MMTV integration site 4, Wnt4 |
| 1382351_at | GTP binding protein (gene overexpressed in skeletal muscle) (predicted), Gem_predicted |
| 1368998_at | NK6 transcription factor related, locus 1 (*Drosophila*), Nkx6-1 |
| 1375120_at | inhibitor of DNA binding 4, Id4 |

TABLE 1-continued

| Accession No. | Description |
|---|---|
| 1384262_at | protein phosphatase 1, regulatory (inhibitor) subunit 3B, Ppp1r3b |
| 1384448_at | similar to RIKEN cDNA 1700045119 (predicted), RGD1565844_predicted |
| 1371091_at | insulin receptor substrate 2, Irs2 |
| 1378899_at | solute carrier family 35, member D3 (predicted), Slc35d3_predicted |
| 1392590_at | Rho GTPase activating protein 24, Arhgap24 |
| 1376901_a_at | Similar to Hypothetical protein 6330514E13 (predicted), RGD1559693_predicted |
| 1367948_a_at | kinase insert domain protein receptor, Kdr |
| 1378925_at | cAMP responsive element modulator, Crem |
| 1379419_at | transmembrane protein 34, Tmem34 |
| 1372308_at | CDNA clone IMAGE: 7366335, --- |
| 1379724_at | pleckstrin homology-like domain, family B, member 2, Phldb2 |
| 1390403_at | family with sequence similarity 43, member A, Fam43a |
| 1393550_at | cAMP responsive element modulator, Crem |
| 1382312_at | AT rich interactive domain 5B (Mrf1 like) (predicted), Arid5b_predicted |
| 1367977_at | synuclein, alpha, Snca |
| 1388108_at | ELOVL family member 6, elongation of long chain fatty acids (yeast), Elovl6 |
| 1390148_a_at | zinc finger protein 395 (predicted), Zfp395_predicted |
| 1369737_at | cAMP responsive element modulator, Crem |
| 1370478_at | myosin XVI, Myo16 |
| 1390127_at | DIX domain containing 1, Dixdc1 |
| 1392183_at | homeobox C9, Hoxc9 |
| 1373786_at | zinc finger protein 703, Zfp703 |
| 1369770_at | somatostatin receptor 1, Sstr1 |
| 1370942_at | RAS p21 protein activator 3, Rasa3 |
| 1397587_at | Histone deacetylase 5, Hdac5 |
| 1387455_a_at | very low density lipoprotein receptor, Vldlr |
| 1376265_at | six transmembrane epithelial antigen of the prostate 2, Steap2 |
| 1387947_at | v-maf musculoaponeurotic fibrosarcoma oncogene family, protein B (avian), Mafb |
| 1385374_at | Transcribed locus, strongly similar to NP_062067.2 thyrotroph embryonic factor [*Rattus norvegicus*], --- |
| 1397729_x_at | similar to RIKEN cDNA 1600029D21, LOC363060 |
| 1381605_at | ubiquitin specific protease 13 (isopeptidase T-3) (predicted), Usp13_predicted |
| 1369564_at | rad and gem related GTP binding protein 2, Rem2 |
| 1387477_at | potassium channel, subfamily K, member 12, Kcnk12 |
| 1395223_at | kelch domain containing 8B, Klhdc8b |
| 1372548_at | Transcribed locus, strongly similar to NP_066940.1 cryptochrome 2 (photolyase-like) [*Homo sapiens*], --- |
| 1385387_at | NK2 transcription factor related, locus 2 (*Drosophila*) (predicted), Nkx2-2_predicted |
| 1385491_at | PNMA-like 2, Pnmal2 |
| 1367805_at | glutaminase, Gls |
| 1374594_at | similar to RIKEN cDNA 1600029D21, LOC363060 |
| 1373179_at | similar to H43E16.1, LOC689994 |
| 1370474_at | thyroid hormone receptor beta, Thrb |
| 1367627_at | glycine amidinotransferase (L-arginine:glycine amidinotransferase), Gatm |
| 1383721_at | frizzled homolog 8 (*Drosophila*), Fzd8 |
| 1375043_at | FBJ osteosarcoma oncogene, Fos |
| 1389611_at | very low density lipoprotein receptor, Vldlr |
| 1393691_at | hypothetical protein LOC688273, LOC688273 |
| 1377404_at | stanniocalcin 1, Stc1 |
| 1379863_at | potassium voltage gated channel, Shal-related family, member 2, Kcnd2 |
| 1368782_at | somatostatin receptor 2, Sstr2 |
| 1391117_at | PNMA-like 2, Pnmal2 |
| 1387968_at | solute carrier family 6 (neurotransmitter transporter), member 15, Slc6a15 |
| 1392663_at | similar to hypothetical protein FLJ13188 (predicted), RGD1305500_predicted |
| 1370058_at | neurofilament, light polypeptide, Nefl |
| 1388395_at | G0/G1 switch gene 2, G0s2 |
| 1377940_at | family with sequence similarity 101, member B, Fam101b |
| 1369098_at | very low density lipoprotein receptor, Vldlr |
| 1387370_at | tropomodulin 1, Tmod1 |
| 1385663_at | ubiquitin specific protease 13 (isopeptidase T-3) (predicted), Usp13_predicted |
| 1370111_at | potassium intermediate/small conductance calcium-activated channel, subfamily N, member 2, Kcnn2 |

TABLE 1-continued

| Accession No. | Description |
|---|---|
| 1382924_at | pantothenate kinase 1 (predicted), Pank1_predicted |
| 1367857_at | fatty acid desaturase 1, Fads1 |
| 1381190_at | LIM domain only protein 7, LMO7 |
| 1373336_at | G protein-coupled receptor, family C, group 5, member B (predicted), Gprc5b_predicted |
| 1369752_a_at | calcium/calmodulin-dependent protein kinase IV, Camk4 |
| 1390339_at | Ubiquitin specific protease 13 (isopeptidase T-3) (predicted), Usp13_predicted |
| 1383390_at | family with sequence similarity 123A, Fam123a |
| 1383826_at | Rab40b, member RAS oncogene family (predicted), Rab40b_predicted |
| 1379374_at | plasticity related gene 1, Lppr4 |
| 1385555_at | family with sequence similarity 101, member A, Fam101a |
| 1398431_at | carbonic anhydrase 8, Car8 |
| 1387212_at | basic helix-loop-helix domain containing, class B, 8, Bhlhb8 |
| 1389911_at | meteorin, glial cell differentiation regulator-like, Metrnl |
| 1393615_at | similar to DEP domain containing 6 (predicted), RGD1561030_predicted |
| 1398732_at | hypothetical protein LOC688273, LOC688273 |
| 1387599_a_at | NAD(P)H dehydrogenase, quinone 1, Nqo1 |
| 1374906_at | ring finger protein 113A1, Rnf113a1 |
| 1374354_at | PHD finger protein 19 (predicted), Phf19_predicted |
| 1372754_at | adaptor protein, phosphotyrosine interaction, PH domain and leucine zipper containing 2, Appl2 |
| 1384415_at | SRY-box containing gene 7 (predicted), Sox7_predicted |
| 1379626_at | Special AT-rich sequence binding protein 1, Satb1 |
| 1373985_at | Similar to KIAA1183 protein (predicted), RGD1560435_predicted |
| 1373108_at | protein phosphatase 1, regulatory (inhibitor) subunit 3C, Ppp1r3c |
| 1375726_at | LIM domain only 7, Lmo7 |
| 1384869_at | abhydrolase domain containing 7 (predicted), Abhd7_predicted |
| 1390097_at | TSPY-like 4, Tspyl4 |
| 1369792_at | G protein-coupled receptor 6, Gpr6 |
| 1369753_at | calcium/calmodulin-dependent protein kinase IV, Camk4 |
| 1390443_at | similar to DNA segment, Chr 16, ERATO Doi 472, expressed (predicted), RGD1563888_predicted |
| 1369095_at | protein phosphatase 1, regulatory (inhibitor) subunit 9A, Ppp1r9a |
| 1376649_at | SNF1-like kinase 2 (predicted), Snf1lk2_predicted |
| 1376687_at | ubiquitin specific peptdiase 1, Usp1 |
| 1369738_s_at | cAMP responsive element modulator, Crem |
| 1389514_at | leucine rich repeat and Ig domain containing 1, Lingo1 |
| 1380305_at | NOD3-like protein, nod3l |
| 1387349_at | short stature homeobox 2, Shox2 |
| 1370317_at | asparagine-linked glycosylation 10 homolog B (yeast, alpha-1,2-glucosyltransferase), Alg10b |
| 1388078_a_at | amiloride-sensitive cation channel 2, neuronal, Accn2 |
| 1393952_at | coiled-coil domain containing 68, Ccdc68 |
| 1391601_at | leucine rich repeat protein 2, neuronal (predicted), Lrrn2_predicted |
| 1385036_at | synuclein, alpha interacting protein (synphilin) (predicted), Sncaip_predicted |
| 1383573_at | teashirt zinc finger family member 1, Tshz1 |
| 1376958_at | Similar to serine (or cysteine) proteinase inhibitor, clade B, member 9 (predicted), RGD1562844_predicted |
| 1372447_at | Fibroblast growth factor receptor 1, Fgfr1 |
| 1385636_at | frizzled homolog 3 (*Drosophila*), Fzd3 |
| 1370122_at | RAB27B, member RAS oncogene family, Rab27b |
| 1371045_at | amiloride-sensitive cation channel 2, neuronal, Accn2 |
| 1377506_at | LAG1 homolog, ceramide synthase 1 /// growth differentiation factor 1 (predicted), Gdf1_predicted /// Lass1 |
| 1379292_at | Similar to 5730420B22Rik protein (predicted), RGD1306755_predicted |
| 1372457_at | mitochondrial tumor suppressor 1, Mtus1 |
| 1374706_at | Growth differentiation factor 11, Gdf11 |
| 1379703_at | DENN/MADD domain containing 3, Dennd3 |
| 1383483_at | RAB9B, member RAS oncogene family (predicted), Rab9b_predicted |
| 1382868_at | sema domain, transmembrane domain (TM), and cytoplasmic domain, (semaphorin) 6A (predicted), Sema6a_predicted |
| 1368825_at | short stature homeobox 2, Shox2 |
| 1369954_at | isocitrate dehydrogenase 1 (NADP+), soluble, Idh1 |
| 1388718_at | tropomodulin 1, Tmod1 |

TABLE 1-continued

Figure 4A:
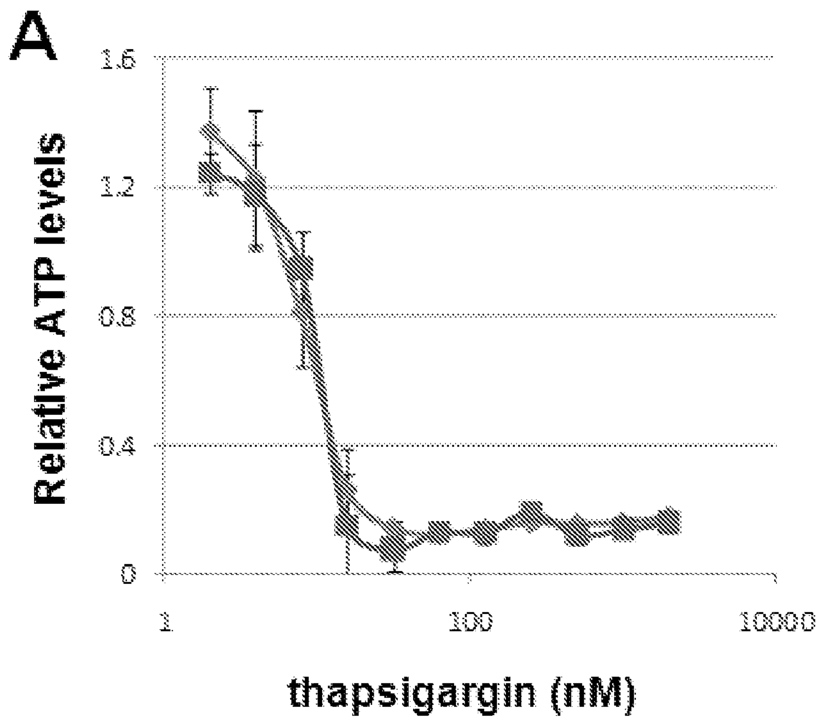
FIG. 4: The effect of Compound-21A (10 μM) on beta cell apoptosis indicated by relative levels of ATP in the presence of common modes of beta-cell apoptosis: (A) ER stress induced by thapsigargin, (B) ER stress induced by tunicamycin, and (C) glucose toxicity. All three graphs show a DMSO control (♦) and Compound-21A (■).
Figure 4B:
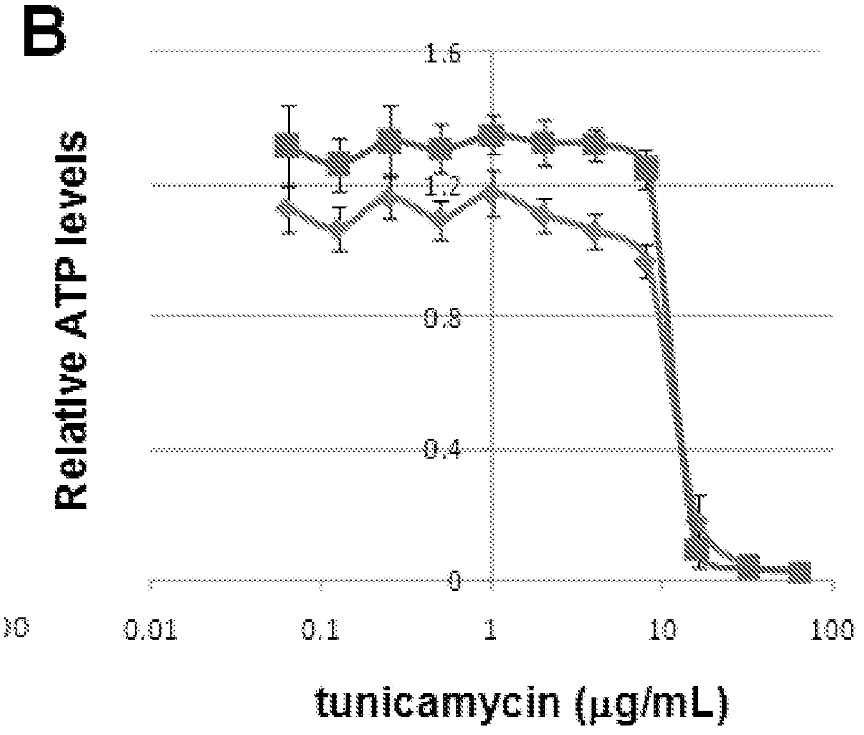
Figure 4C:
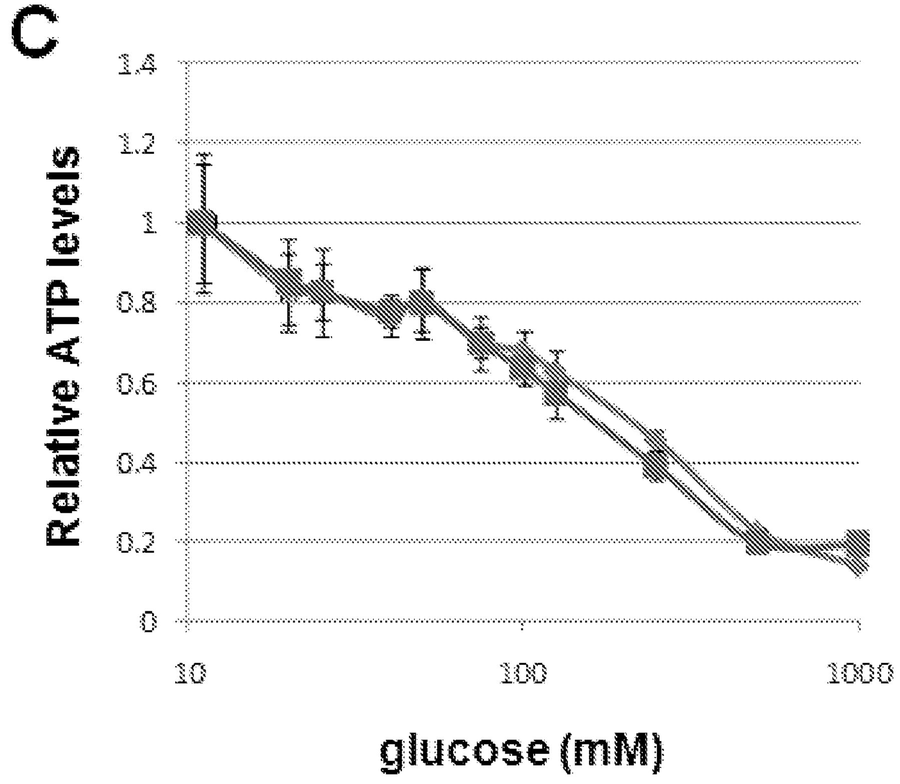
Figure 5A:
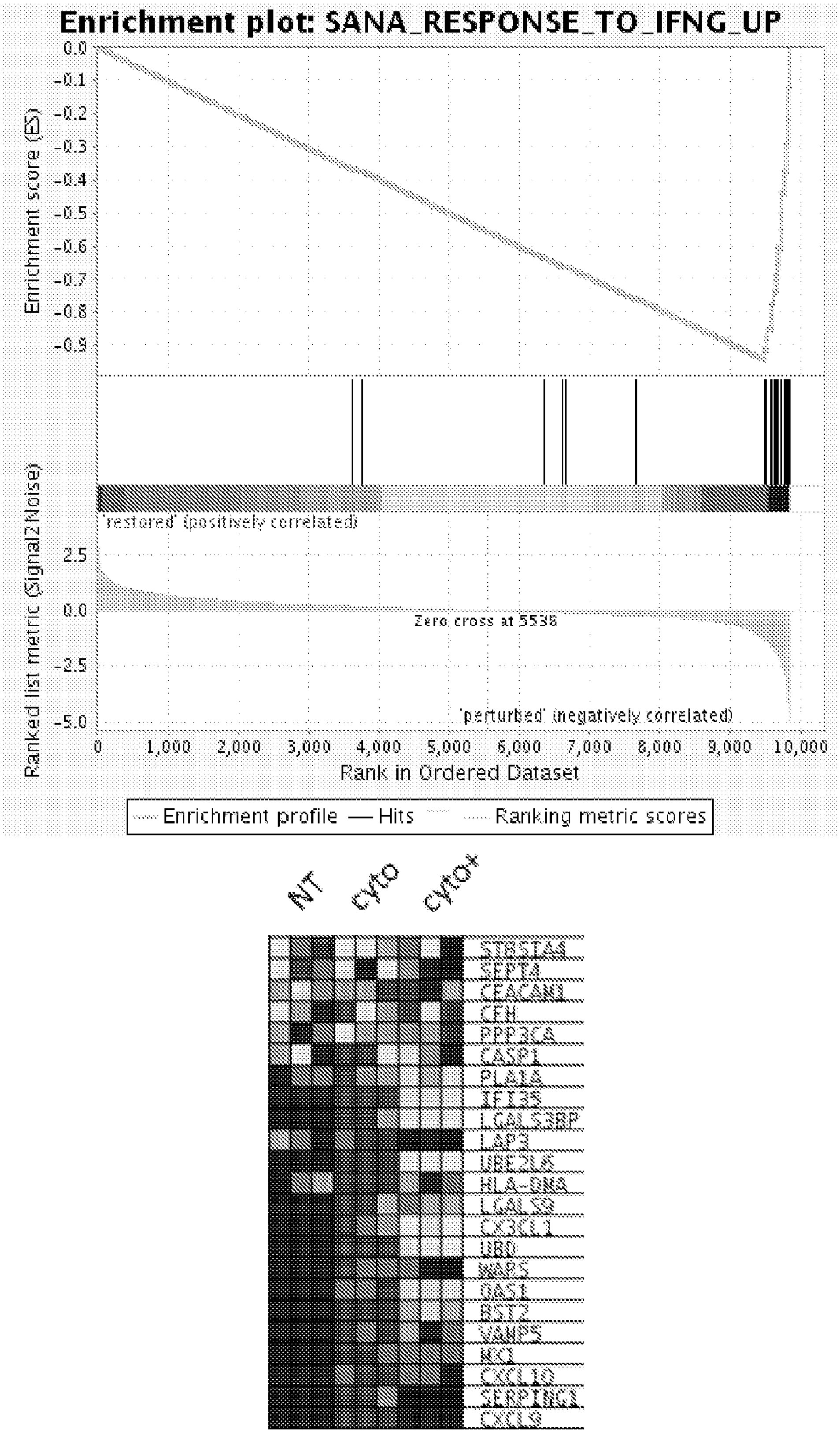
FIG. 5: Gene-set enrichment analysis after 6-hr treatment with Compound-21A: (A) Enrichment plot showing SANA response to interferon-γ, (B) Enrichment plot showing Browne response to interferon-γ.
Figure 5B:
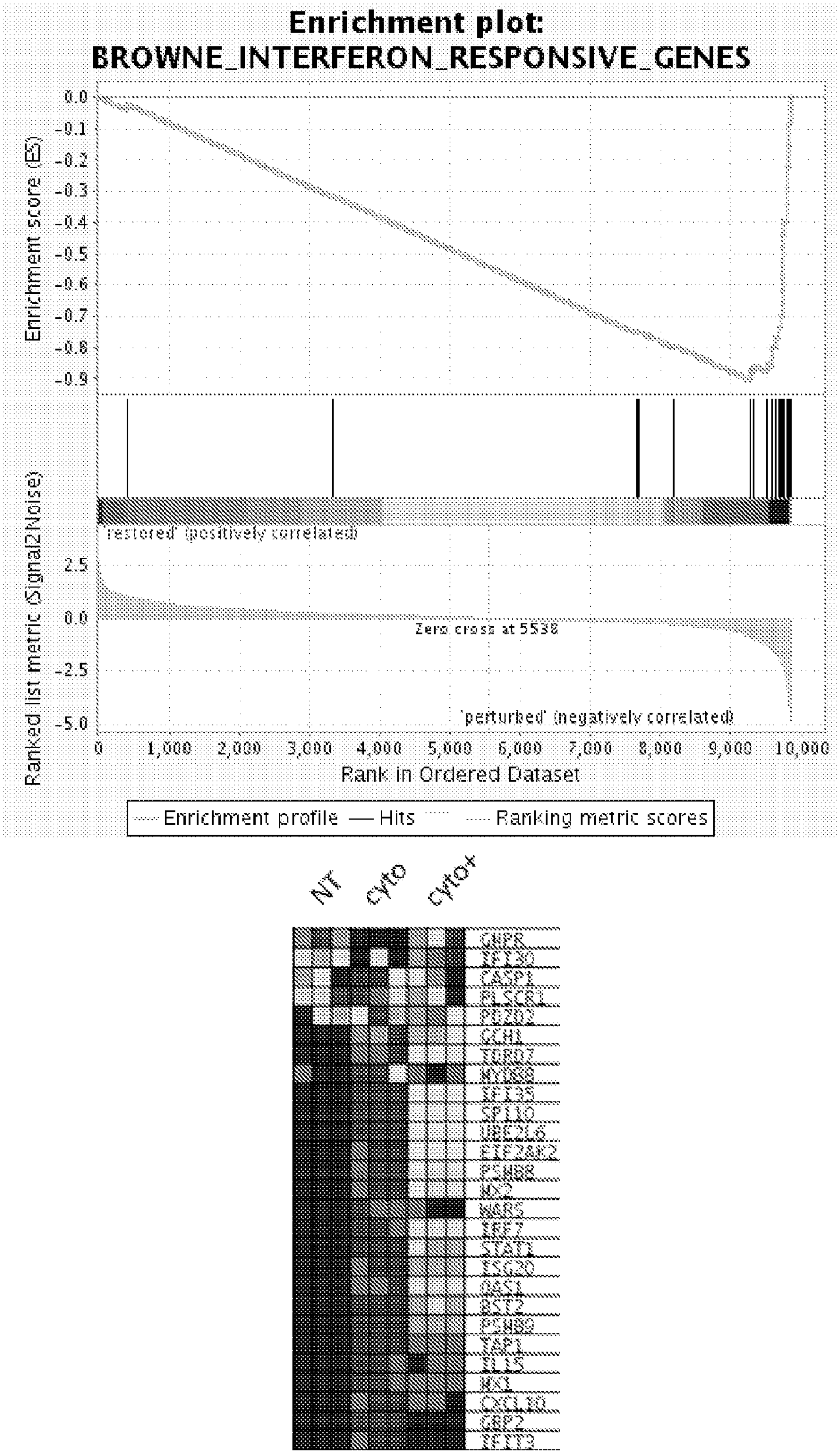
Figure 6:
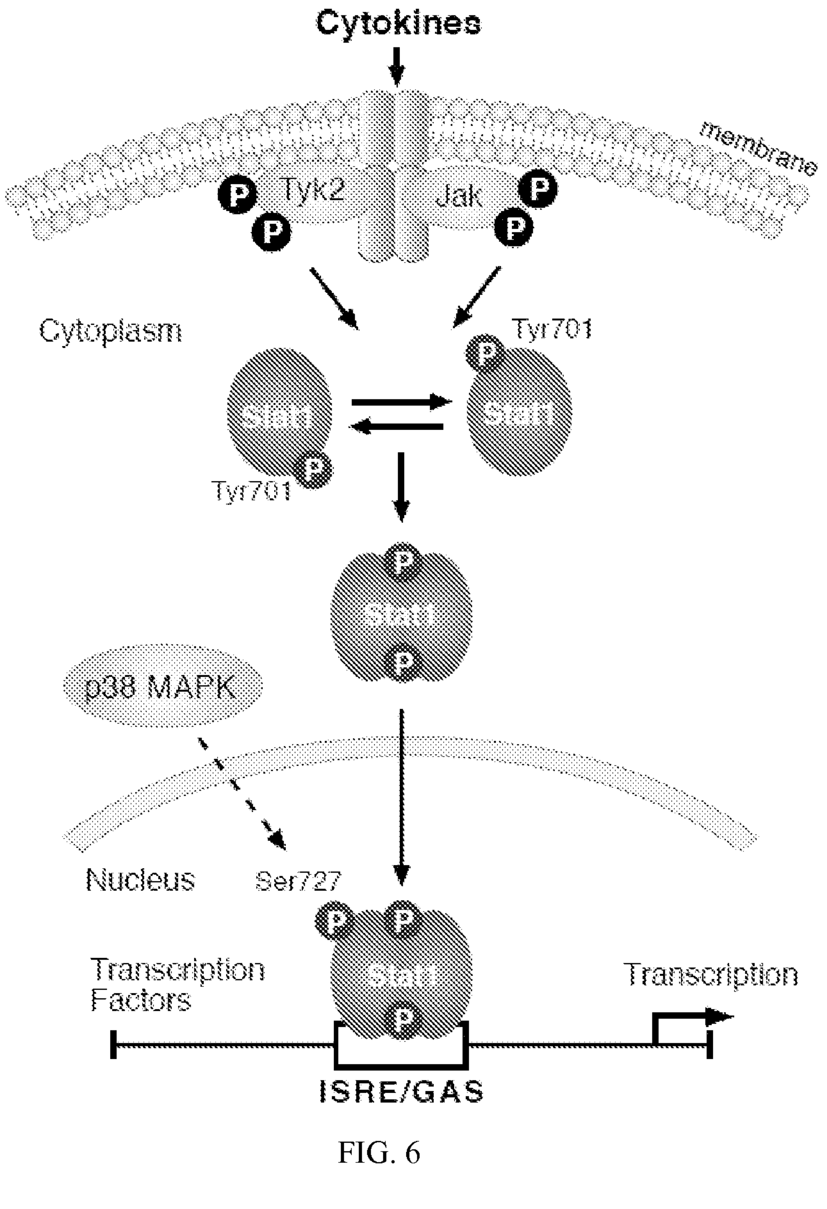
FIG. 6: Schematic showing role of interferon-γ in STAT1-dependent signaling pathway.
Figure 7:
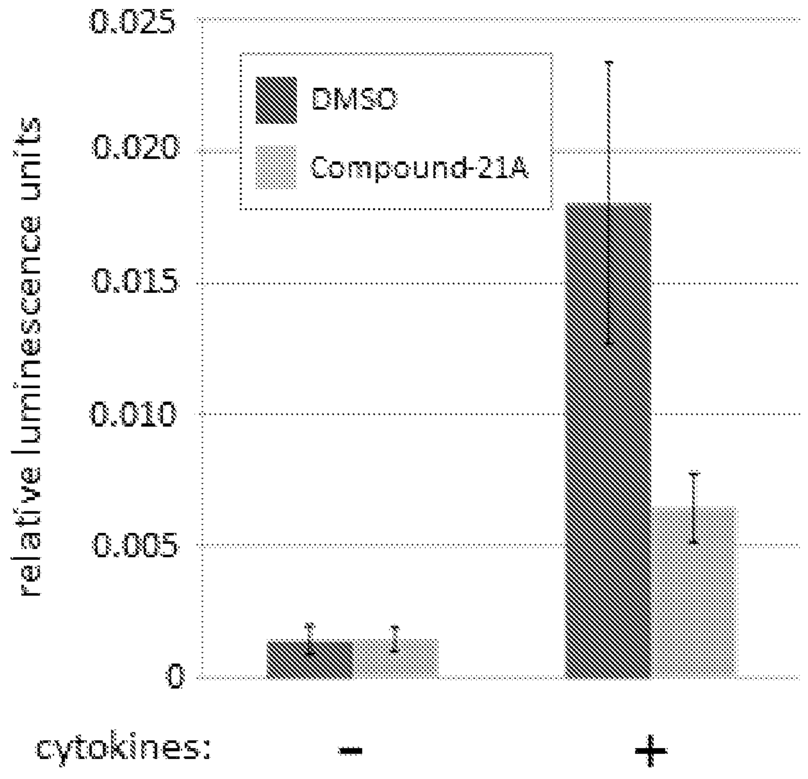
FIG. 7: Compound-21A inhibits cytokine-induced STAT1 reporter gene activity.
Figure 8:
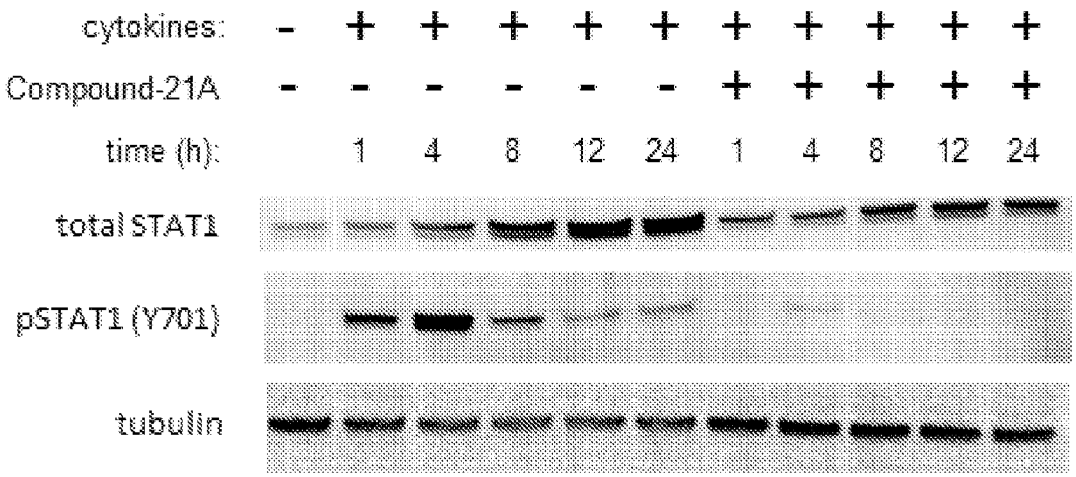
FIG. 8: Suppression of STAT1 phosphorylation by Compound-21A.
Figure 9:
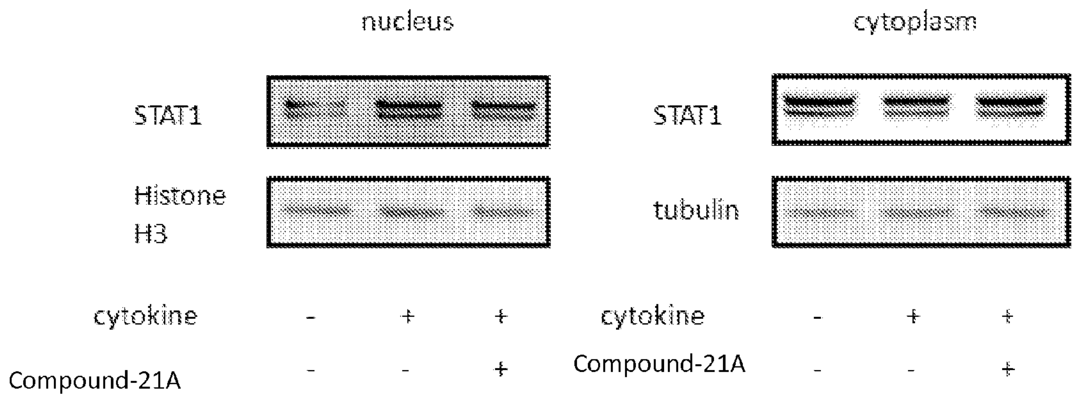
FIG. 9: Inhibition of nuclear STAT1 translocation by Compound-21A.
Figure 10:
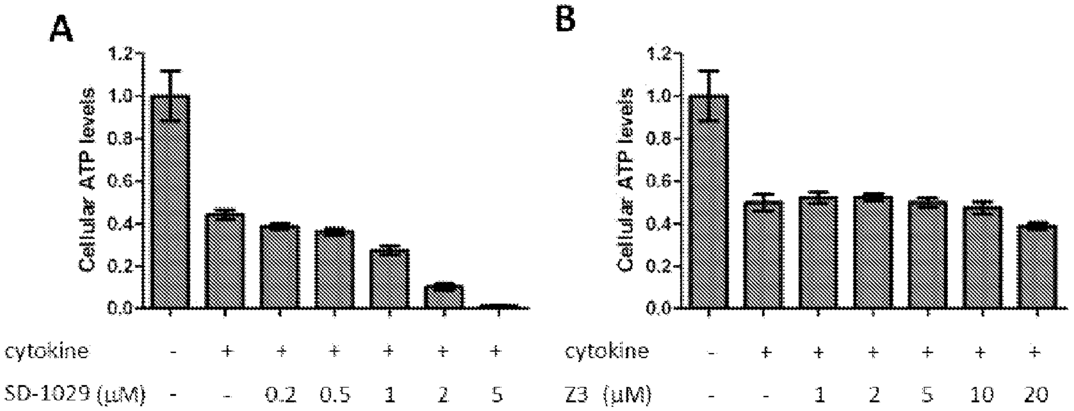
FIG. 10: The effect of putative JAK2 inhibitors, SD-1029 and Z3, on cytokine-induced beta cell apoptosis.
Figure 11:
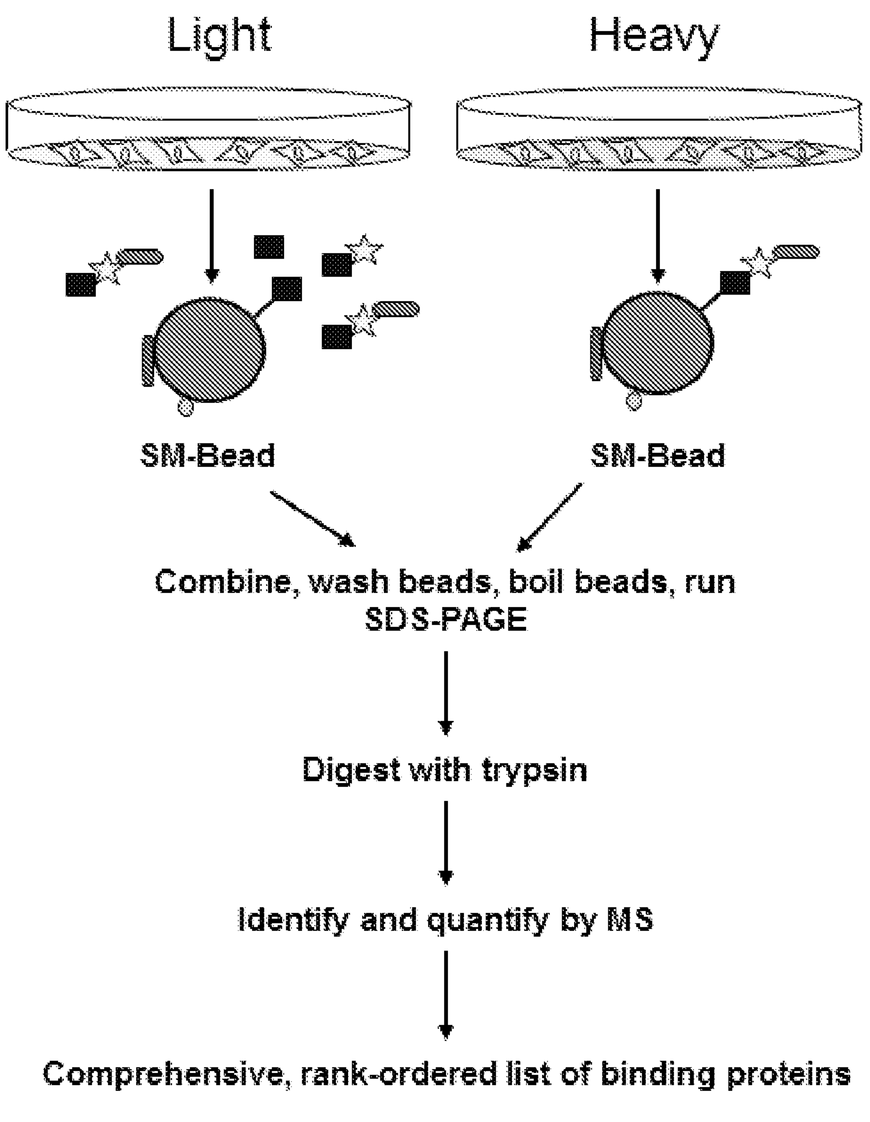
FIG. 11: Schematic of candidate protein binder by Stable Isotope Labeling by Amino Acids in Cell Culture (SILAC).
Figure 13:
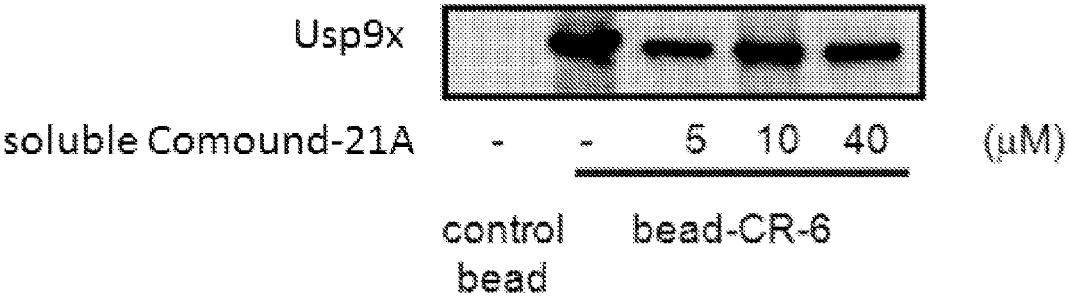
FIG. 13: Usp9x isolated by low-throughput Compound-21A pull-down and Western blot.
Figure 14:
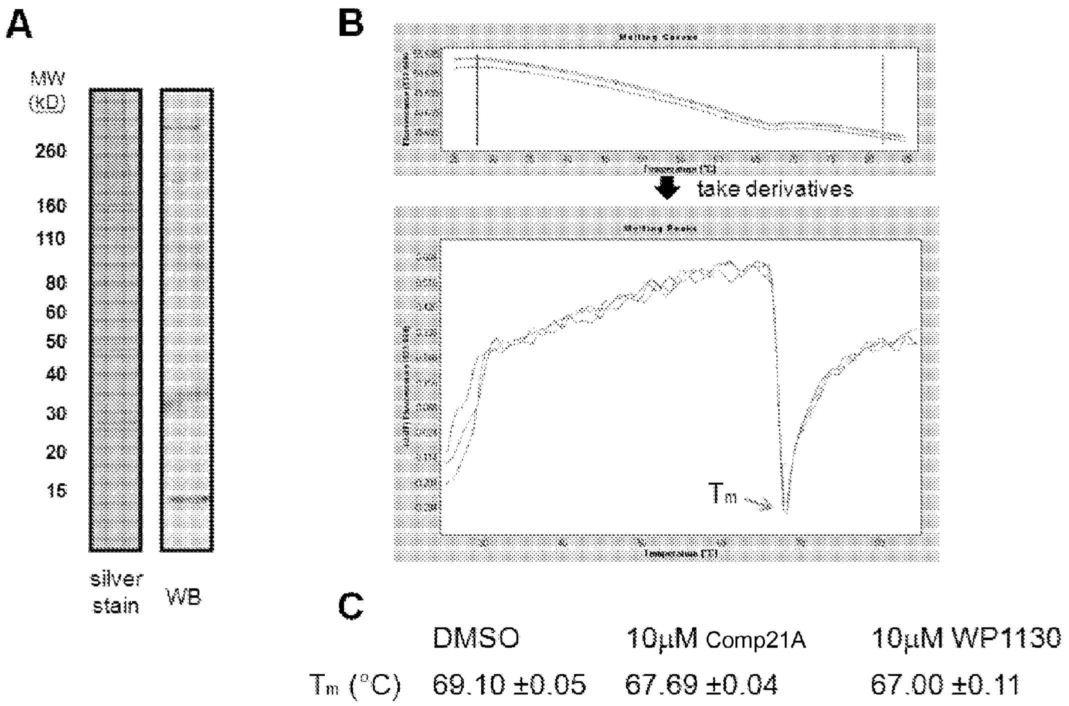
FIG. 14: Usp9x purification and thermal shift assay and comparison of Compound-21A with non-specific debiquitinase inhibitor WP1130, suggests binding.
Figure 15:
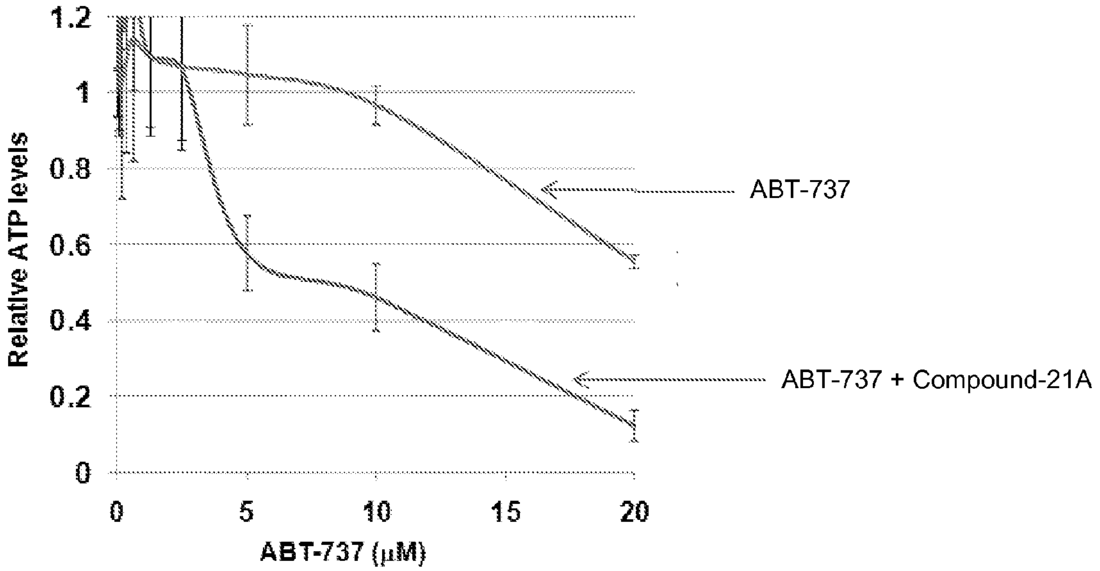
FIG. 15: Compound-21 enhances effect of ABT-737 on DLD-1 cell death.
Figure 16:
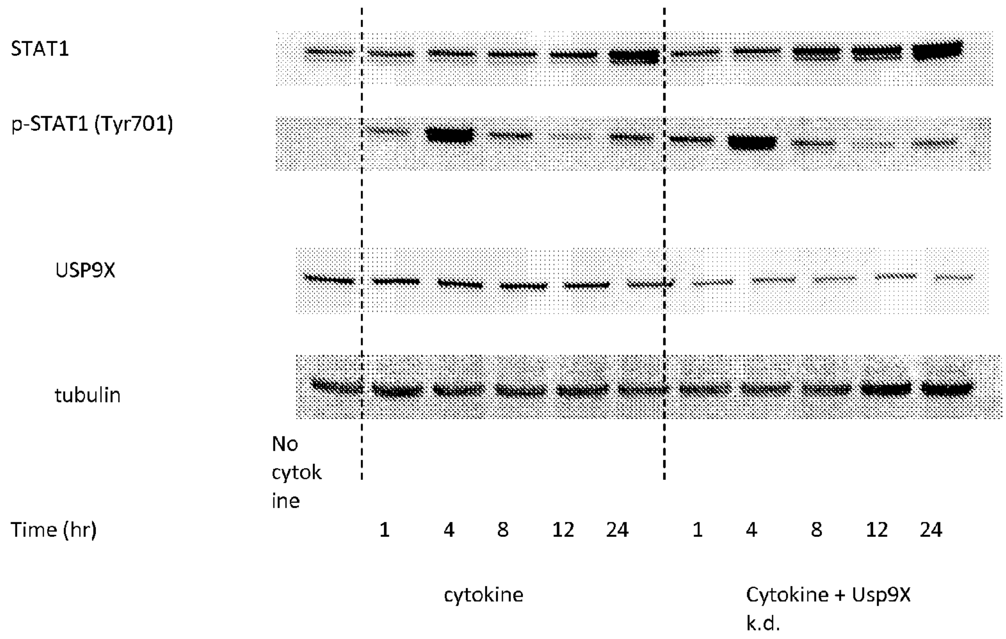
FIG. 16: STAT1 levels and phosphorylation after Usp9x knock-down.

| Accession No. | Description |
|---|---|
| 1370218_at | lactate dehydrogenase B, Ldhb |
| 1393307_at | Phosphatase and actin regulator 3, Phactr3 |
| 1372365_at | Ras and Rab interactor 2 (predicted), Rin2_predicted |
| 1386960_at | solute carrier family 37 (glucose-6-phosphate transporter), member 4, Slc37a4 |
| 1372117_at | myotubularin related protein 10, Mtmr10 |
| 1383443_at | similar to UPF0308 protein C9orf21, LOC498685 |
| 1374236_at | leucine-rich repeat LGI family, member 2 (predicted), Lgi2_predicted |
| 1391194_at | Sal-like 1 (*Drosophila*) (predicted), Sall1_predicted |
| 1398606_at | golgi integral membrane protein 4, Golim4 |
| 1390289_at | FIG4 homolog (*S. cerevisiae*), Fig4 |
| 1371421_at | similar to 3-oxoacid CoA transferase 1, LOC678860 |
| 1379257_at | erythrocyte protein band 4.1-like 4a (predicted), Epb4.1l4a_predicted |
| 1370941_at | platelet derived growth factor receptor, alpha polypeptide, Pdgfra |
| 1392739_a_at | endonuclease/exonuclease/phosphatase family domain containing 1, Eepd1 |
| 1376187_at | Solute carrier family 35 (UDP-glucuronic acid/UDP-N-acetylgalactosamine dual transporter), member D1 (predicted), Slc35d1_predicted |
| 1397267_at | RIM binding protein 2, Rimbp2 |
| 1384009_at | nuclear prelamin A recognition factor, Narf |
| 1384238_at | tweety homolog 2 (*Drosophila*), Ttyh2 |
| 1385175_at | homeo box B13 (predicted), Hoxb13_predicted |
| 1389054_at | similar to RIKEN cDNA 0610040J01, LOC498368 |
| 1396492_at | Nfat activating molecule with ITAM motif 1, Nfam1 |
| 1375909_at | similar to glutathione transferase GSTM7-7, MGC108896 |
| 1392040_at | spindle assembly 6 homolog (*C. elegans*) (predicted), Sass6_predicted |
| 1375353_at | Cdk5 and Abl enzyme substrate 1 (predicted), Cables1_predicted |
| 1390993_at | phenazine biosynthesis-like protein domain containing, Pbld |
| 1372069_at | ankyrin repeat domain 15, Ankrd15 |
| 1389787_at | PTK7 protein tyrosine kinase 7 (predicted), Ptk7_predicted |
| 1390168_a_at | DPH4 homolog (JJJ3, *S. cerevisiae*), Dph4 |
| 1397861_at | V-set and transmembrane domain containing 2B, Vstm2b |
| 1368160_at | insulin-like growth factor binding protein 1, Igfbp1 |
| 1382478_at | BTB (POZ) domain containing 3 (predicted), Btbd3_predicted |
| 1389003_at | Rho-related BTB domain containing 3 (predicted), Rhobtb3_predicted |
| 1370407_at | prenylcysteine oxidase 1, Pcyox1 |
| 1384331_at | sulfiredoxin 1 homolog (*S. cerevisiae*), Srxn1 |
| 1392789_at | solute carrier family 25, member 36, Slc25a36 |
| 1390481_a_at | ubiquitin-conjugating enzyme E2T (putative) (predicted), Ube2t_predicted |
| 1377599_at | lipin 1, Lpin1 |
| 1369686_at | doublecortin-like kinase 1, Dclk1 |
| 1370106_at | fibroblast growth factor 18, Fgf18 |
| 1390050_at | similar to Golgi phosphoprotein 2 (Golgi membrane protein GP73), LOC680692 /// LOC682869 |
| 1390647_at | putative homeodomain transcription factor 2 (predicted), Phtf2_predicted |
| 1371131_a_at | thioredoxin interacting protein, Txnip |
| 1388703_at | endothelial cell adhesion molecule, Esam |
| 1381969_at | similar to Recombining binding protein suppressor of hairless (J kappa-recombination signal binding protein) (RBP-J kappa), LOC679028 |
| 1379541_at | transmembrane and tetratricopeptide repeat containing 4, Tmtc4 |
| 1373398_at | Tripartite motif protein 37 (predicted), Trim37_predicted |
| 1367806_at | glutaminase, Gls |
| 1388973_at | procollagen, type IX, alpha 1, Col9a1 |
| 1385321_at | similar to Protein arginine N-methyltransferase 4 (Heterogeneous nuclear ribonucleoprotein methyltransferase-like protein 4), LOC688502 |
| 1370416_at | Max dimerization protein 3, Mxd3 |
| 1376873_at | cerebellin 1, Cbln1 |
| 1375423_at | hypothetical protein LOC689959, LOC689959 |
| 1373291_at | deleted in liver cancer 1, Dlc1 |
| 1377729_at | elongation of very long chain fatty acids (FEN1/Elo2, SUR4/Elo3, yeast)-like 4 (predicted), Elovl4_predicted |
| 1392943_at | membrane bound O-acyltransferase domain containing 2, Mboat2 |
| 1367899_at | coagulation factor II (thrombin) receptor, F2r |

TABLE 1-continued

| Accession No. | Description |
|---|---|
| 1389067_at | solute carrier organic anion transporter family, member 4a1, Slco4a1 |
| 1370158_at | myosin, heavy polypeptide 10, non-muscle, Myh10 |
| 1396112_at | myotubularin related protein 10, Mtmr10 |
| 1387503_at | carboxypeptidase N, polypeptide 1, Cpn1 |
| 1389632_at | Rho-related BTB domain containing 1 (predicted), Rhobtb1_predicted |
| 1386129_at | inhibitor of growth family, member 2, Ing2 |
| 1377669_at | RAB27A, member RAS oncogene family, Rab27a |
| 1379817_at | purine-rich element binding protein G (predicted), Purg_predicted |
| 1379302_at | recombining binding protein suppressor of hairless (*Drosophila*) (predicted) /// similar to Recombining binding protein suppressor of hairless (J kappa-recombination signal binding protein) (RBP-J kappa), LOC679028 /// Rbpsuh_predicted |
| 1374333_at | similar to RIKEN cDNA 1110007C09 (predicted), RGD1306058_predicted |
| 1383433_at | kelch-like 23 (*Drosophila*) (predicted), Klhl23_predicted |
| 1370059_at | neurofilament, light polypeptide, Nefl |
| 1368174_at | EGL nine homolog 3 (*C. elegans*), Egln3 |
| 1391871_at | StAR-related lipid transfer (START) domain containing 13, Stard13 |
| 1395160_at | proline-rich transmembrane protein 3, Prrt3 |
| 1367869_at | oxidation resistance 1, Oxr1 |
| 1381974_at | BTB (POZ) domain containing 3 (predicted), Btbd3_predicted |
| 1393101_at | F-box and leucine-rich repeat protein 10, Fbxl10 |
| 1374846_at | hexamethylene bis-acetamide inducible 1, Hexim1 |
| 1374748_at | serine hydroxymethyltransferase 1 (soluble), Shmt1 |
| 1375877_at | synaptotagmin IV, Syt4 |
| 1398296_at | glycerophosphodiester phosphodiesterase 1, Gde1 |
| 1371963_at | propionyl-coenzyme A carboxylase, alpha polypeptide, Pcca |
| 1398484_at | similar to TBC1 domain family, member 8 (with GRAM domain); vascular Rab-GAP/TBC-containing (predicted), RGD1308221_predicted |
| 1391077_at | claspin homolog (*Xenopus laevis*) (predicted), Clspn_predicted |
| 1369735_at | growth arrest specific 6, Gas6 |
| 1390406_at | Rho GTPase activating protein 18 (predicted), Arhgap18_predicted |
| 1384516_at | Metal response element binding transcription factor 2, Mtf2 |
| 1370247_a_at | peripheral myelin protein 22, Pmp22 |
| 1387623_at | stanniocalcin 1, Stc1 |
| 1386577_at | kelch-like 23 (*Drosophila*) (predicted), Klhl23_predicted |
| 1370237_at | hydroxyacyl-Coenzyme A dehydrogenase, Hadh |
| 1385302_at | glycerophosphodiester phosphodiesterase domain containing 1 (predicted), Gdpd1_predicted |
| 1373959_at | protein phosphatase 2 (formerly 2A), regulatory subunit A (PR 65), beta isoform, Ppp2r1b |
| 1398398_at | homeo box A10, Hoxa10 |
| 1383601_at | CDNA clone MGC: 188768 IMAGE: 9101044, --- |
| 1370268_at | potassium voltage-gated channel, shaker-related subfamily, member 5, Kcna5 |
| 1389549_at | proline synthetase co-transcribed (predicted), Prosc_predicted |
| 1374160_at | transmembrane and coiled-coil domains 2, Tmcc2 |
| 1374890_at | Transcribed locus, strongly similar to NP_005656.4 ecotropic viral integration site 5 [*Homo sapiens*], --- |
| 1390228_at | amine oxidase, flavin containing 1 (predicted), Aof1_predicted |
| 1378235_at | glycerophosphodiester phosphodiesterase domain containing 1 (predicted), Gdpd1_predicted |
| 1392406_at | IAP promoted placental gene (predicted), Ipp_predicted |
| 1371983_at | Josephin domain containing 1, Josd1 |
| 1389791_at | ceroid-lipofuscinosis, neuronal 8, Cln8 |
| 1392165_at | inhibitor of growth family, member 2, Ing2 |
| 1387805_at | BCL2/adenovirus E1B 19 kDa-interacting protein 3, Bnip3 |
| 1374491_at | CKLF-like MARVEL transmembrane domain containing 8, Cmtm8 |
| 1387310_at | ATPase, Ca++ transporting, type 2C, member 2, Atp2c2 |
| 1384852_at | RAB27A, member RAS oncogene family, Rab27a |
| 1368924_at | growth hormone receptor, Ghr |
| 1368964_at | leucine rich repeat protein 3, neuronal, Lrrn3 |
| 1376213_at | similar to Rap2-binding protein 9, MGC124740 |
| 1369696_at | Ras-related GTP binding B, RragB |

TABLE 1-continued

| Accession No. | Description |
|---|---|
| 1373043_at | stromal cell-derived factor 2-like 1 (predicted), Sdf2l1_predicted |
| 1372782_a_at | adenosine monophosphate deaminase 2 (isoform L), Ampd2 |
| 1383382_at | similar to jumonji protein, LOC681740 |
| 1390028_at | dual-specificity tyrosine-(Y)-phosphorylation regulated kinase 2 (predicted), Dyrk2_predicted |
| 1383326_a_at | programmed cell death 4, Pdcd4 |
| 1399005_at | protein phosphatase 2, regulatory subunit B (B56), alpha isoform (predicted), Ppp2r5a_predicted |
| 1389301_at | similar to muscleblind-like 2 isoform 1, LOC680445 |
| 1368440_at | solute carrier family 3, member 1, Slc3a1 |
| 1377869_at | CCR4 carbon catabolite repression 4-like B (*S. cerevisiae*), Ccrn4lb |
| 1372093_at | Max interacting protein 1, Mxi1 |
| 1370548_at | solute carrier family 16 (monocarboxylic acid transporters), member 10, Slc16a10 |
| 1390249_at | septin 14, Sept14 |
| 1388919_at | zinc finger protein 541, Zfp541 |
| 1397173_at | similar to Serine/threonine-protein kinase WNK3 (Protein kinase, lysine-deficient 3) (predicted), RGD1563131_predicted |
| 1382814_at | odd Oz/ten-m homolog 3 (*Drosophila*) (predicted), Odz3_predicted |
| 1373659_at | hypothetical protein LOC688257, LOC688257 |
| 1391906_at | cortistatin /// kinesin family member 1B, Cort /// Kif1b |
| 1378430_at | monooxygenase, DBH-like 1, Moxd1 |
| 1373656_at | protein phosphatase 1, regulatory subunit 3D, Ppp1r3d |
| 1376758_at | inhibitor of growth family, member 1, Ing1 |
| 1375059_at | zinc finger protein 652, Zfp652 |
| 1374957_at | similar to ribosomal protein L27a (predicted), RGD1560633_predicted |
| 1384877_at | aquaporin 11, Aqp11 |
| 1370054_at | cyclin-dependent kinase inhibitor 2C (p18, inhibits CDK4), Cdkn2c |
| 1367755_at | cysteine dioxygenase 1, cytosolic, Cdo1 |
| 1383328_x_at | programmed cell death 4, Pdcd4 |
| 1379440_at | follistatin-like 3, Fstl3 |
| 1395623_at | glutaminyl-peptide cyclotransferase-like (predicted), Qpctl_predicted |
| 1370036_at | sulfite oxidase, Suox |
| 1369670_at | Cd200 antigen, Cd200 |
| 1392953_at | protein tyrosine phosphatase-like (proline instead of catalytic arginine), member a, Ptpla |
| 1383534_at | Transcribed locus, moderately similar to XP_001479249.1 PREDICTED: similar to zinc finger protein 605 [*Mus musculus*], --- |
| 1384885_at | tektin 2, Tekt2 |
| 1368122_at | ring finger protein 103, Rnf103 |
| 1373625_at | serine hydroxymethyltransferase 1 (soluble), Shmt1 |
| 1388856_at | kit ligand, Kitl |
| 1367702_at | acyl-Coenzyme A dehydrogenase, medium chain, Acadm |
| 1374625_at | hairy and enhancer of split 6 (*Drosophila*), Hes6 |
| 1369785_at | phosphoribosyl pyrophosphate amidotransferase, Ppat |
| 1385829_at | obscurin-like 1, Obsl1 |
| 1383962_at | SIVA1, apoptosis-inducing factor, Siva1 |
| 1383666_at | peptidyl-tRNA hydrolase 1 homolog (*S. cerevisiae*) (predicted), Ptrh1_predicted |
| 1373345_at | adhesion molecule with Ig like domain 2, Amigo2 |
| 1391919_at | transcription elongation regulator 1-like, Tcerg1l |
| 1384392_at | cytochrome P450, family 26, subfamily b, polypeptide 1, Cyp26b1 |
| 1374540_at | cell division cycle associated 7, Cdca7 |
| 1385503_at | similar to O-acetyltransferase, LOC678772 |
| 1393439_a_at | progressive ankylosis, Ank |
| 1374030_at | similar to KIAA0999 protein, LOC684112 |
| 1377995_at | integrin alpha FG-GAP repeat containing 3, Itfg3 |
| 1393218_at | similar to 2410024A21Rik protein, RGD1304878 |
| 1383722_at | proline synthetase co-transcribed (predicted), Prosc_predicted |
| 1374235_at | regulator of calcineurin 2, Rcan2 |
| 1372248_at | sestrin 1 (predicted), Sesn1_predicted |
| 1387670_at | glycerol-3-phosphate dehydrogenase 2, mitochondrial, Gpd2 |
| 1387032_at | cholecystokinin, Cck |
| 1395269_s_at | gamma-aminobutyric acid (GABA-A) receptor, subunit delta, Gabrd |
| 1387662_at | synaptotagmin IV, Syt4 |

TABLE 1-continued

| Accession No. | Description |
|---|---|
| 1369010_at | CHK2 checkpoint homolog (*S. pombe*), Chek2 |
| 1393347_at | integrin alpha L, Itgal |
| 1376963_at | dual-specificity tyrosine-(Y)-phosphorylation regulated kinase 2 (predicted), Dyrk2_predicted |
| 1371763_at | similar to RIKEN cDNA 4931406C07, RGD1309534 |
| 1386978_at | BCL2/adenovirus E1B interacting protein 3-like, Bnip3l |
| 1370814_at | dehydrogenase/reductase (SDR family) member 4, Dhrs4 |
| 1369457_a_at | synaptotagmin-like 4, Sytl4 |
| 1367853_at | solute carrier family 12 (sodium/potassium/chloride transporters), member 2, Slc12a2 |
| 1392079_at | A kinase (PRKA) anchor protein 7, Akap7 |
| 1395968_at | similar to Myosin-15 (Myosin XV) (Unconventional myosin-15), LOC688264 |
| 1369412_a_at | solute carrier family 19 (sodium/hydrogen exchanger), member 1, Slc19a1 |
| 1381515_at | CDNA clone IMAGE: 7123062, --- |
| 1370120_at | follistatin-like 3, Fstl3 |
| 1379258_at | kelch-like 5 (*Drosophila*), Klhl5 |
| 1373734_at | Solute carrier organic anion transporter family, member 3a1, Slco3a1 |
| 1389084_at | Transcribed locus, weakly similar to XP_001480799.1 PREDICTED: hypothetical protein [*Mus musculus*], --- |
| 1393109_at | CDNA clone IMAGE: 7302574, --- |
| 1373480_at | heat shock 70 kDa protein 12A (predicted), Hspa12a_predicted |
| 1367791_at | receptor (calcitonin) activity modifying protein 1, Ramp1 |
| 1396317_at | cell cycle progression 1 (predicted), Ccpg1_predicted |
| 1387521_at | programmed cell death 4, Pdcd4 |
| 1374976_a_at | Sterol O-acyltransferase 1, Soat1 |
| 1384210_at | MICAL C-terminal like, Micalcl |
| 1369000_at | neurotrophic tyrosine kinase, receptor, type 1, Ntrk1 |
| 1389876_at | Calcium/calmodulin-dependent protein kinase II inhibitor 1, Camk2n1 |
| 1371679_at | synaptopodin 2, Synpo2 |
| 1383444_at | solute carrier family 24 (sodium/potassium/calcium exchanger), member 2, Slc24a2 |
| 1379108_at | Similar to ADP-ribosylation factor guanine nucleotide factor 6 isoform a (predicted), RGD1559968_predicted |
| 1387271_at | phytanoyl-CoA hydroxylase, Phyh |
| 1390207_at | large tumor suppressor 2 (predicted), Lats2_predicted |
| 1368514_at | monoamine oxidase B, Maob |
| 1393196_at | kelch-like 23 (*Drosophila*) (predicted), Klhl23_predicted |
| 1379608_at | RGD1560010 (predicted), RGD1560010_predieted |
| 1388958_a_at | solute carrier family 2 (facilitated glucose transporter), member 4, Slc2a4 |
| 1383300_at | kelch-like 24 (*Drosophila*), Klhl24 |
| 1374557_at | G protein-coupled receptor 177, Gpr177 |
| 1371113_a_at | transferrin receptor, Tfrc |
| 1393848_at | ribonucleotide reductase M2, Rrm2 |

The invention further relates to a compound of Formula II:

Formula II

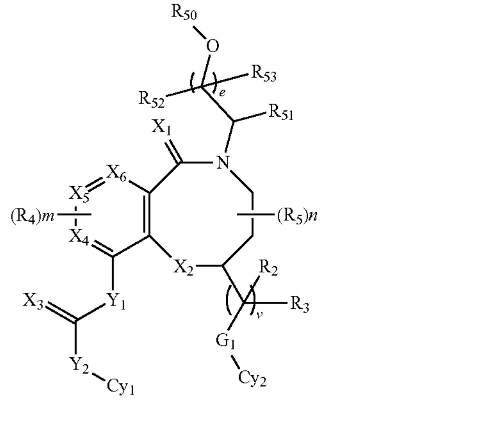

Wherein e is 0, 1, 2, 3 or 4;

$R_{50}$ is —C(O)$R_{54}$, —C(O)N(H)$R_{54}$, —C(S)$R_{54}$, —C(S)N(H)$R_{54}$;

wherein $R_{54}$ is alkyl or substituted alkyl, $—(CH_2)_2O(CH_2CH_2O)_fCH_2CH_2NH_2$, $—(CH_2)_2—O—(CH_2CH_2)_g NH_2$, $—(CH_2CH_2)_gNH_2$, $—(CH_2)_2—O—(CH_2CH_2O)_f CH_2CH_2SH$, $—(CH_2)_2—O—(CH_2CH_2)_g SH$, $—(CH_2CH_2)_gOH$, $—(CH_2)_2—O—(CH_2CH_2O)_f CH_2CH_2OH$, $—(CH_2)_2—O—(CH_2CH_2)_gOH$, $—(CH_2CH_2)_gOH$;

Wherein each f and g is independently, an integer between 0 and 500, preferably, 0, 1, 2, 3, 4, 5, 6, 7, 8, 9, 10, 11, 12, 13, 14, 15 or 17.

Each $R_{51}$, $R_{52}$ and $R_{53}$ is independently hydrogen, halogen, —$OR_{10}$, —$SR_{10}$, —$NR_{10}R_{11}$, —C(O)$R_{10}$, —C(O)$OR_{10}$, —C(O)$NR_{10}R_{11}$, —N($R_{10}$)C(O)$R_{11}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, optionally substituted aliphatic, optionally substituted aryl or optionally substituted heterocyclyl.

The compounds of Formula II can be immobilized onto a surface or a bead through the $R_{50}$ group. The immobilized compounds can be used to identify proteins, genes or DNA that can interact with the immobilized compound.

In a preferred embodiment, the invention relates to a compound of Formula II having the structure:

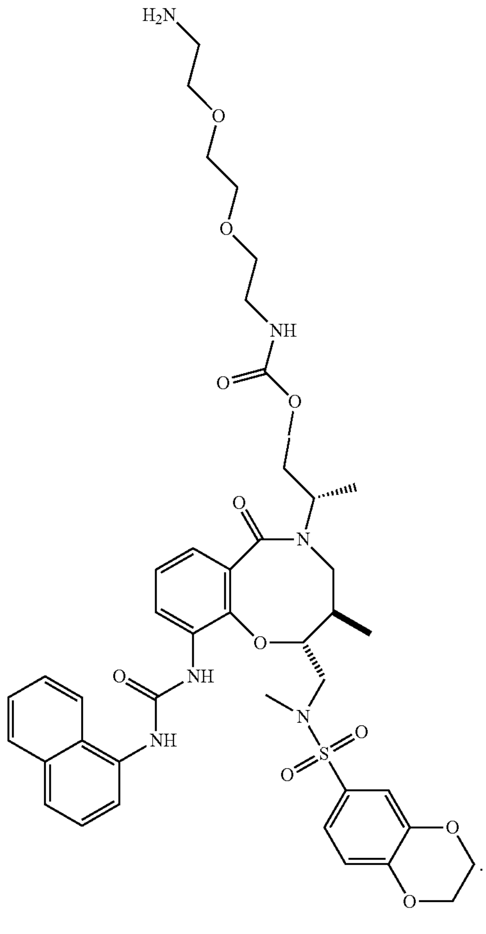 [SMILES: C[C@@H]1CN([C@@H](C)COC(=O)NCCOCCOCCN)C(=O)c2cccc(NC(=O)Nc3cccc4ccccc34)c2O[C@H]1CN(C)S(=O)(=O)c1ccc2c(c1)OCCO2]

DEFINITIONS

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include branched, straight chain and cyclic, substituted or unsubstituted saturated aliphatic hydrocarbon radicals/groups having the specified number of carbons. Preferred alkyl groups comprise about 1 to about 24 carbon atoms ("$C_1$-$C_{24}$") preferably about 7 to about 24 carbon atoms ("$C_7$-$C_{24}$"), preferably about 8 to about 24 carbon atoms ("$C_8$-$C_{24}$"), preferably about 9 to about 24 carbon atoms ("$C_9$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3—CH_2—$), or in other instances, a bivalent linking moiety can be "alkyl," in which case those skilled in the art will understand the alkyl to be a divalent radical (e.g., $—CH_2—CH_2—$), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The term carbocyclic biaryl refers to fused bicyclic moieties, typically containing 4-20 carbon atoms. An example is naphthalene. The biaryl groups may contain 1-4 heteroatoms. Examples include indoles, isoindoles, quinolines, isoquinolines, benzofurans, isobenzofurans, benzothiophenes, benzo[c]thiophenes, benzimidazoles, purines, indazoles, benzoxazole, benzisoxazole, benzothiazole, quinoxalines, quinazolines, cinnolines, and the like.

The terms "compound" and "drug" as used herein all include pharmaceutically acceptable salts, co-crystals, solvates, hydrates, polymorphs, enantiomers, diastereoisomers, racemates and the like of the compounds and drugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-($\beta$) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a “therapeutically effective amount” of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect).

In certain embodiments, one or more therapeutic agents of the dosage unit may exist in an extended or control release formulation and additional therapeutic agents may not exist in extended release formulation. In one embodiment, the extended release contemplates the substantially continuous delivery of drug over an extended period of time, such as greater than one, two, three, four or more weeks. For example, an agent described herein may exist in a controlled release formulation or extended release formulation in the same dosage unit with another agent that may or may not be in either a controlled release or extended release formulation. Thus, in certain embodiments, it may be desirable to provide for the immediate release of one or more of the agents described herein, and the controlled release of one or more other agents. The rate of delivery may be altered, for example, by varying the lactide/glycolide ratio in a poly(D,L-lactide-co-glycolide) encapsulation. Other polymers that may be used include polyacetal polymers, polyorthoesters, polyesteramides, polycaprolactone and copolymers thereof, polycarbonates, polyhydroxybuterate and copolymers thereof, polymaleamides, copolyaxalates and polysaccharides. In one embodiment of the invention, a compound of formula I is formulated with an extended release component, such as a coated extended release matrix, an extended release matrix, or an extended release bead matrix. In one example, a compound of Formula I is used in combination with a polymer matrix (e.g., Eudragit), Hydroxypropyl methyl cellulose (HPMC) and/or a polymer coating (e.g., Eudragit). Such formulations can, for example, be compressed into solid tablets or granules or formed into pellets for capsules or tablets. Extended release oral formulation can be prepared using additional methods known in the art. For example, a suitable extended release form of a compound of Formula I may be a matrix tablet composition. Suitable matrix forming materials include, for example, waxes (e.g., carnauba, bees wax, paraffin wax, ceresine, shellac wax, fatty acids, and fatty alcohols), oils, hardened oils or fats (e.g., hardened rapeseed oil, castor oil, beef tallow, palm dil, and soya bean oil), and polymers (e.g., hydroxypropyl cellulose, polyvinylpyrrolidone, hydroxypropyl methyl cellulose, and polyethylene glycol). Other suitable matrix tabletting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Multi-layered tablets are especially preferred when the active ingredients have markedly different pharmacokinetic profiles. Extended release formulations can be made by spray drying polymer-drug mixtures, emulsion-based technologies, coacervation based technologies, film casting, extrusion based technologies and other processes to manufacture polymer-drug microparticles possessing an extended release profile. Examples of suitable extended release technologies that can be used to incorporate the compounds of formula I described herein include, without limitation, the MEDISORB® technology, as described in, for example, U.S. Pat. No. 6,264,987 to Wright, U.S. Pat. No. 5,654,008 and/or U.S. Pat. No. 5,792,477, for example; the PROLEASE® technology, as described, for example in U.S. Pat. No. 6,358,443 to Herbert; the technologies described by Southern Research Institute, as described for example in U.S. Pat. No. 6,306,425; and “Method of Preparing Sustained Release Microparticles,” U.S. Application No. 60/441,946, filed Jan. 23, 2003, and the technologies described by Alza Corp., including the ALZAMER® Depot injection technology. The contents of these patents are incorporated herein by reference in their entirety.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Synthesis of Compound 21A

Compound 21

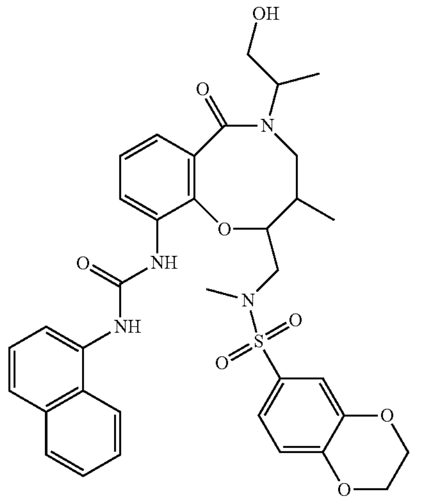

Compound 21A

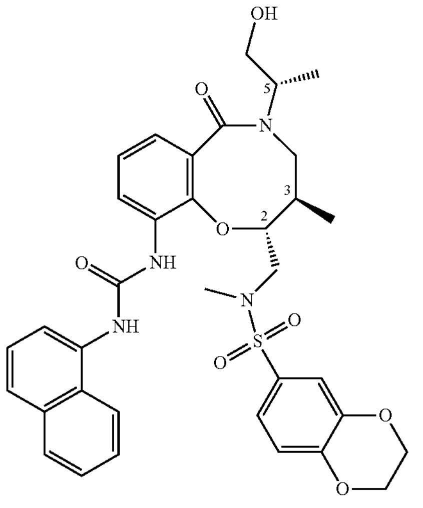

Scheme 1

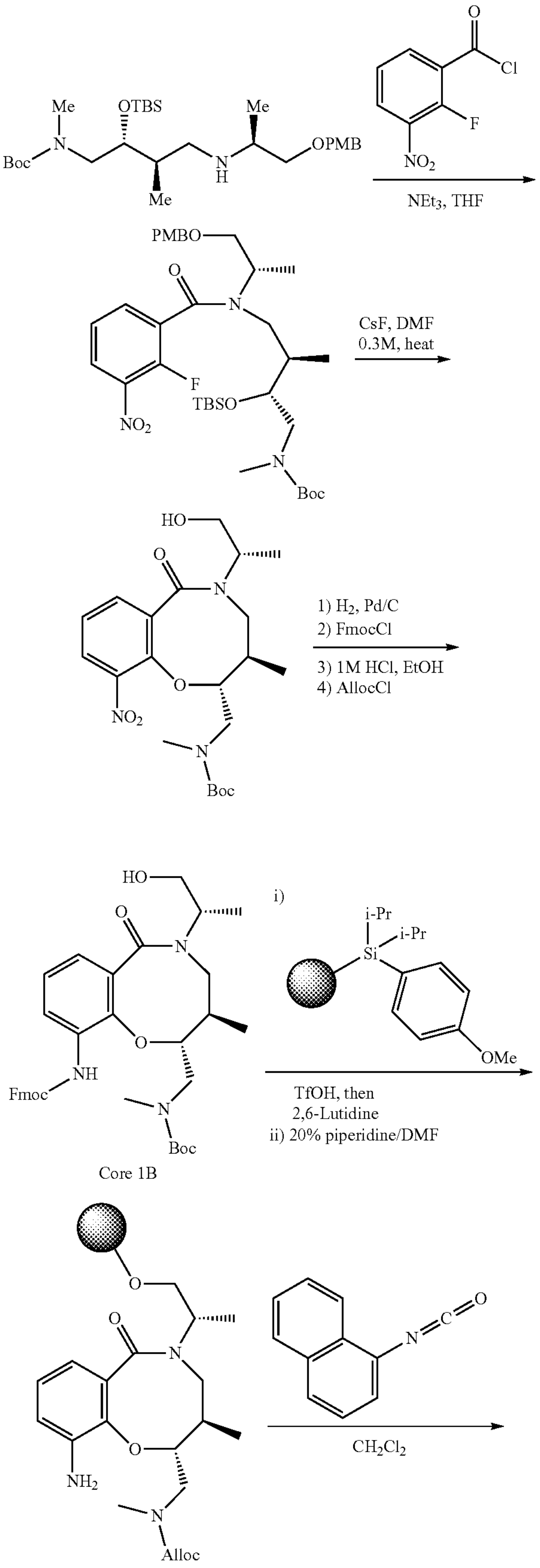

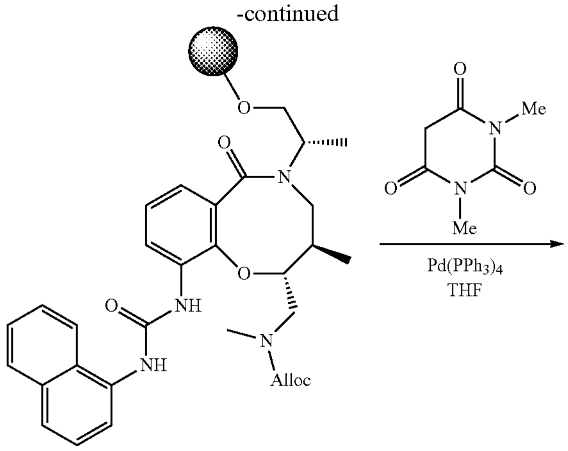

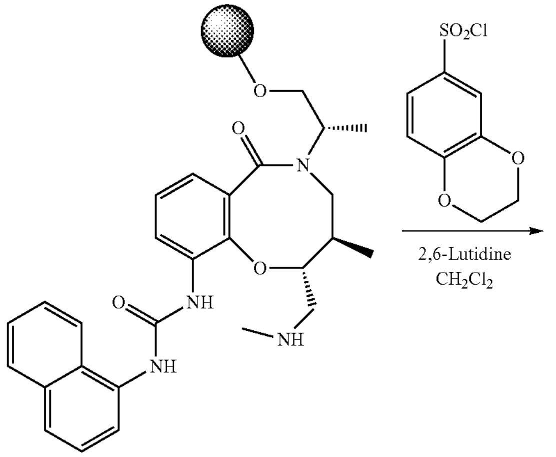

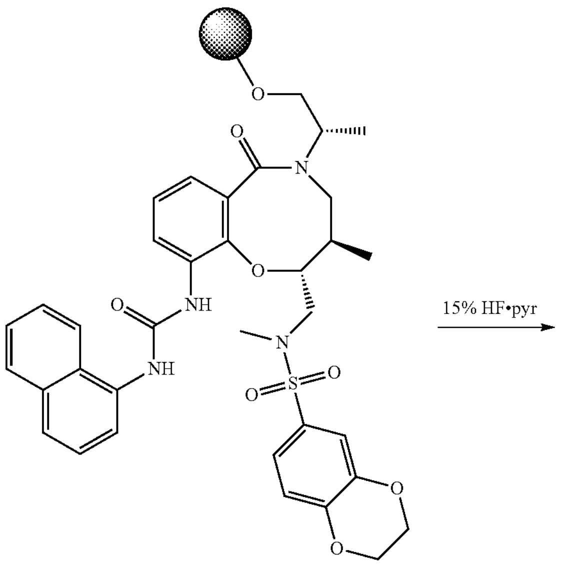

-continued

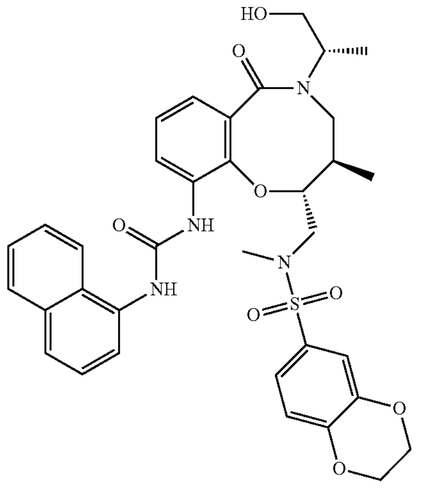 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)OCCO2]

tert-butyl((2R,3R)-2-((tert-butyldimethylsilyl)oxy)-4-(((S)-1-((4-methoxybenzyl)oxy)-propan-2-yl)amino)-3-methylbutyl)(methyl)carbamate, EMF-2

This compound was synthesized according to literature procedure (*J. Am. Chem. Soc.* Marcaurelle, L., et al, accepted).

EMF-4

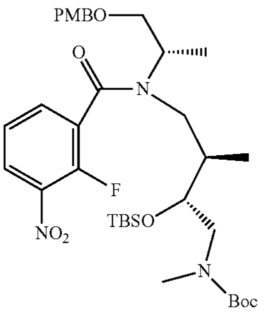

tert-Butyl-((2R,3R)-2-((tert-butyldimethylsilyl)oxy)-4-(2-fluoro-N-((S)-1-((4-methoxybenzyl)oxy)propan-2-yl)-3-nitrobenzamido)-3-methylbutyl)(methyl) carbamate, EMF-4

To a stirred solution of EMF-2 (21 g, 40.0 mmol, 1 equiv) and 2-fluoro-3-nitrobenzoyl chloride (20.36 g, 100 mmol, 2.5 equiv) in $CH_2Cl_2$ (120 mL) at 0° C. was added triethyl amine ($NEt_3$) (27.7 mL, 200 mmol, 5 equiv). The reaction was allowed to warm to room temperature as it stirred, and no starting material remained after 1.5 h. $H_2O$ (50 mL) was added to the reaction and it was extracted with $CH_2Cl_2$ (2×100 mL). The combined organic portion was dried over $MgSO_4$, filtered, and concentrated. The crude material was purified by silica gel chromatography in Ethyl Acetate (EtOAc)/hexanes (10%→30%) to give the product. HRMS (ESI) calculated for $C_{35}H_{55}FN_3O_8Si$ $[M+H]^+$: 692.3737, found: 692.3764.

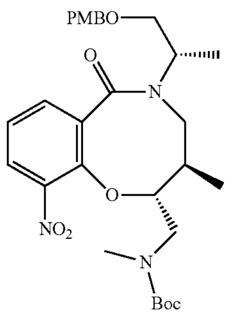

tert-Butyl(((2R,3R)-5-(S)-1-((4-methoxybenzyl)oxy)propan-2-yl)-3-methyl-10-nitro-6-oxo-3,4,5,6-tetrahydro-2H-benzo[b][1,5]oxazocin-2-yl)methyl)(methyl)carbamate, EMF-5

To a stirred solution of EMF-4 (24.5 g, 35.4 mmol, 1 equiv) in N,N-Dimethylformamide (DMF, 708 mL) was added CsF (10.76 g, 70.8 mmol (2 equiv). The resulting suspension was heated to 85° C. for 5 h. The solvent was then removed under reduced pressure, and the crude solid was dissolved in EtOAc (250 mL), washed with $H_2O$ (1×100 mL) and brine (1×100 mL), dried over $Na_2SO_4$, filtered, and concentrated. The product was used in the next reaction without purification. HRMS (ESI) calcd for $C_{29}H_{39}N_3NaO_8$ $[M+Na]^+$: 580.2629, found: 580.2614.

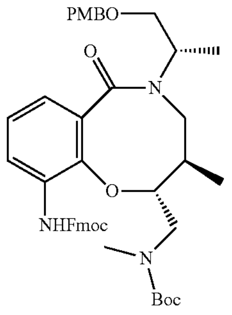

tert-Butyl(((2R,3R)-10-((((9H-fluoren-9-yl)methoxy)carbonyl)amino)-5-((S)-1-((4-methoxybenzyl)oxy)propan-2-yl)-3-methyl-6-oxo-3,4,5,6-tetrahydro-2H-benzo[b][1,5]oxazocin-2-yl)methyl)(methyl)carbamate, EMF-6

A mixture of compound EMF-5 (7.51 g, 13.47 mmol, 1 equiv) and Pd/C (1.43 g, 1.347 mmol, 0.1 equiv) in EtOH (500 mL) were stirred under $H_2$ at 40° C. No starting material remained after 2 h, and the reaction was cooled, filtered through Celite, and concentrated. The crude material was used in the next reaction without purification. The product (0.852 g, 1.614 mmol) was taken up in 10% aqueous $NaHCO_3$ (10 mL) in dioxane (60 mL), and a solution of FmocCl (2.088 g, 8.07 mmol, 5 equiv) in dioxane (5 mL) at 0° C. was added via syringe. The resulting cloudy solution was allowed to stir for 15 min at 0° C. and then room temperature overnight. The solution became clear as it warmed to room temperature. The reaction was quenched with sat. $NH_4Cl$ solution and extracted with EtOAc (2×100 mL). The combined organic portion was dried over $MgSO_4$, filtered, and concentrated. The crude material was purified by silica gel chromatography (EtOAc/hexanes gradient). HRMS (ESI) calcd for $C_{44}H_{51}N_3NaO_8$: 772.3568 $[M+Na]^+$ found: 772.3593.

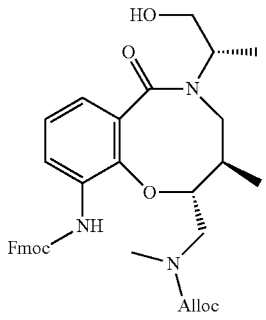

Allyl (((2R,3R)-10-((((9H-fluoren-9-yl)methoxy)carbonyl)amino)-5-((S)-1-hydroxypropan-2-yl)-3-methyl-6-oxo-3,4,5,6-tetrahydro-2H-benzo[b][1,5]oxazocin-2-yl)methyl)(methyl)carbamate, EMF-7

To a stirred solution of EMF-6 in $CH_2Cl_2$ (200 mL, 0.1 M) was added 2,6-lutidine (9.94 mL, 85 mmol, 4.0 equiv), and TBSOTf (14.7 mL, 64 mmol, 3.0 equiv). The mixture was stirred for 2 h and then quenched with saturated $NH_4Cl$ solution and extracted with EtOAc. The combined organic extracts were dried over $MgSO_4$, filtered, and concentrated. The resulting oil was dissolved in $CH_2Cl_2$ (120 mL) and cooled to −78° C. before triethylamine (12.5 mL, 90 mmol, 5.0 equiv) and allyl chloroformate (1.78 mL, 16.7 mmol, 1.0 equiv) were added. After 10 minutes, the reaction was quenched with saturated $NH_4Cl$ and extracted with $CH_2Cl_2$. The combined organic extracts were dried over $MgSO_4$, filtered, and concentrated. The crude material was purified by silica gel chromatography (EtOAc/hexanes 30%→50%) to give the product (12.2 g, 78%).

The product (12.2 g, 16.6 mmol, 1.0 equiv) was then dissolved in $CH_2Cl_2$ (200 mL) and pH 7 buffer (15 mL). The mixture was cooled to 0° C. and dichloro dicyano quinone (DDQ; 5.66 g, 24.9 mmol, 1.5 equiv) was added. The mixture was stirred for 10 minutes at 0° C. and then 1 h at room temperature before quenching with $H_2O$. The product was then extracted with $CH_2Cl_2$, and the combined organic portion was washed with saturated $NaHCO_3$ before activated carbon was added. The mixture was then filtered through Celite, and the Celite was washed several times with hot $CH_2Cl_2$. The filtrate was concentrated and the crude material was purified by silica gel chromatography (0%→5% MeOH/$CH_2Cl_2$) to give the product (10.0 g, 98%). HRMS (ESI) calcd for $C_{35}H_{40}N_3O_7$ $[M+H]^+$: 614.2861, found: 614.2840.

General Protocol A for Cleavage of the Compound from the Lantern and its Characterization for Qualitative Analysis A portion of each product was used to assure that each reaction was complete. To complete this qualitative analysis and characterization, one segment of a lantern (¼) was severed and placed in a polypropylene vial (or 96-well plate) and HF/pyridine (200 μL) was added to completely submerge the lantern. The reaction was allowed to sit at room temperature for 3 h. The reaction was then quenched by slow addition of methoxytrimethylsilane (400 μL, >2 equiv). After 15 min, the quenched solution was then removed and combined with additional methanol (MeOH) washes (2×200 μL). The product was dried under reduced pressure to yield a solid which was dissolved in dimethyl sulfoxide (DMSO) and analyzed by ultraperformance liquid chromatography/mass spectrometer (UPLC/MS).

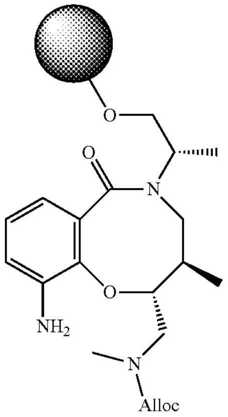

EMF-31

Allyl (((2R,3R)-10-amino-5-((S)-1-hydroxypropan-2-yl)-3-methyl-6-oxo-3,4,5,6-tetrahydro-2H-benzo[b][1,5]oxazocin-2-yl)methyl)(methyl)carbamate/EMF-31

Core 1B was synthesized as shown on the scheme 1 above. Core 1B (353 mg, 0.576 mmol) was rigorously dried by evaporating with benzene (3×5 mL) to azeotrope water. The white solid was dried under reduced pressure overnight. SynPhase L-series alkyl tethered diisopropylarylsilane lanterns (32 Lanterns, ~15 μmol/lantern) were prepared for loading by washing with $CH_2Cl_2$ (3×20 min) and dried overnight under reduced pressure. The lanterns were then activated in an oven-dried vial by addition of 3% TfOH in $CH_2Cl_2$. The vial was shaken for 10 minutes, and the lanterns turned bright red. The liquid was removed, 2,6-lutidine was added, and the lanterns were shaken until the red color disappeared. A small amount of $CH_2Cl_2$ was added to the lanterns followed by core 1B (353 mg, 0.576 mmol, 1.2 equiv) in $CH_2Cl_2$. Enough $CH_2Cl_2$ was added to cover the lanterns, and the reaction was shaken for 60 hours. The reaction solvent was then removed, and the lanterns were washed with $CH_2Cl_2$ (2×8 mL) and DMF (2×8 mL). The lanterns were shaken in 20% piperidine in DMF (8 mL) for 30 minutes to remove the Fmoc protecting group. The lanterns were then washed with DMF (2×8 mL), 3:1 THF/$H_2O$ (1×8 mL), 3:1 THF:isopropanol (1×8 mL), THF (1×8 mL), and $CH_2Cl_2$ (2×8 mL). General protocol A was used to release the compound from the lantern for subsequent for characterization to ascertain that the reaction was complete. LRMS $(M+H)^+$: 392.19.

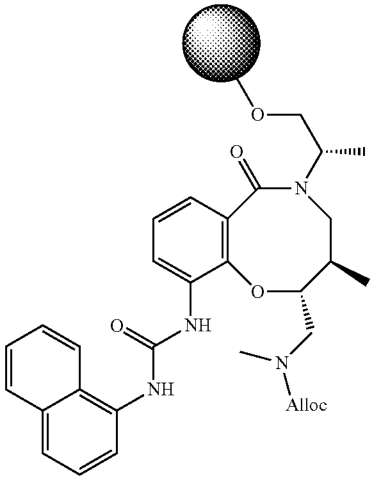

EMF-32

Allyl (((2R,3R)-5-((S)-1-hydroxypropan-2-yl)-3-methyl-10-(3-(naphthalen-1-yl)ureido)-6-oxo-3,4,5,6-tetrahydro-2H-benzo[b][1,5]oxazocin-2-yl)methyl)(methyl)carbamate/EMF-32

To EMF-31 (26¾ lanterns, 0.401 mmol) in $CH_2Cl_2$ (8 mL) was added 1-isocyanatonaphthalene (1.357 g, 8.02 mmol, 20 equiv). The vial was sealed and shaken at room temperature for 36 h. The reaction mixture was then removed and the lanterns were washed with $CH_2Cl_2$ (1×8 mL), DMF (2×8 mL), THF/$H_2O$ (3:1, 1×8 mL), THF/isopropanol (3:1, 1×8 mL), THF (1×8 mL), and $CH_2Cl_2$ (2×8 mL). General protocol A was used to release the compound from the lantern for subsequent for characterization to ascertain that the reaction was complete. LRMS $(M+H)^+$: 561.20.

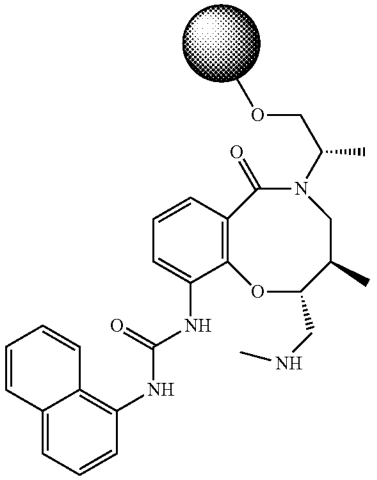

EMF-37

1-((2R,3R)-5-((S)-1-Hydroxypropan-2-yl)-3-methyl-2-((methylamino)methyl)-6-oxo-3,4,5,6-tetrahydro-2H-benzo[b][1,5]oxazocin-10-yl)-3-(naphthalen-1-yl)urea/EMF-37

To EMF-32 (26½ lanterns, 0.383 mmol) in THF (8 mL) was added dimethylbarbituric acid (1.798 g, 11.51 mmol, 30 equiv) and $Pd(PPh_3)_4$ (444 mg, 0.384 mmol, 1.0 equiv). The vial was sealed and the reaction was allowed to shake at room temperature overnight. The reaction mixture was then removed, and the lanterns were washed with $CH_2Cl_2$ (2×8 mL) and DMF (5×8 mL). The lanterns were then shaken in DMF (8 mL) overnight. The solvent was removed and the lanterns were washed with DMF (2×8 mL), THF/$H_2O$ (3:1, 1×8 mL), THF/isopropanol (3:1, 1×8 mL), THF (1×8 mL), and $CH_2Cl_2$ (2×8 mL). General protocol A was used to release the compound from the lantern for subsequent for characterization to ascertain that the reaction was complete. LRMS $(M+H)^+$: 477.22.

Compound-21A

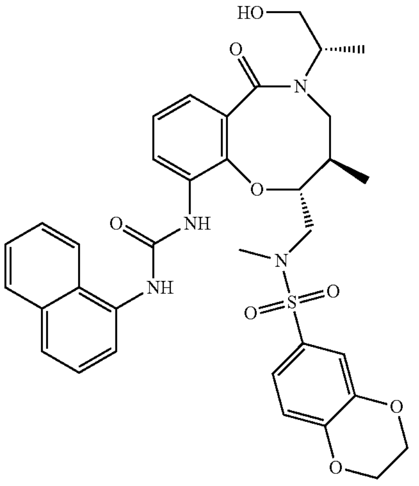

N-(((2R,3R)-5-((S)-1-Hydroxypropan-2-yl)-3-methyl-10-(3-(naphthalen-1-yl)ureido)-6-oxo-3,4,5,6-tetrahydro-2H-benzo[b][1,5]oxazocin-2-yl)methyl)-N-methyl-2,3-dihydrobenzo-[b][1,4]dioxine-6-sulfonamide/Compound 21A: $EC_{50}$=770 nM To EMF-37 (11¼ lanterns, 0.169 mmol) in $CH_2Cl_2$ (8 mL) was added 2,6-lutidine (490 uL, 4.22 mmol, 25 equiv) and 2,3-dihydrobenzo[b][1,4]dioxine-6-sulfonyl chloride (792 mg, 3.38 mmol, 20 equiv). The reaction was allowed to shake for 60 h, and the reaction mixture was removed. The lanterns were washed with $CH_2Cl_2$ (1×8 mL), DMF (2×8 mL), THF/$H_2O$ (3:1, 1×8 mL), THF/isopropanol (3:1, 1×8 mL), THF (1×8 mL), and $CH_2Cl_2$ (2×8 mL). General Protocol A was used to release the compound from the lantern for subsequent for characterization to ascertain that the reaction was complete. The remaining lanterns were then cleaved according to General Protocol A to give the product as a white solid. LRMS $(M+H)^+$: 675.21.

Example 2

Synthesis of Compound-20A

Compound 20

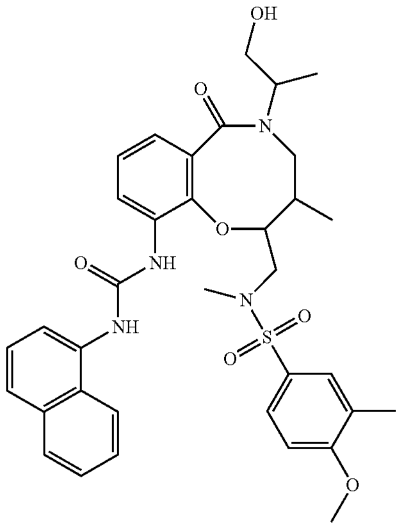

Compound 20A

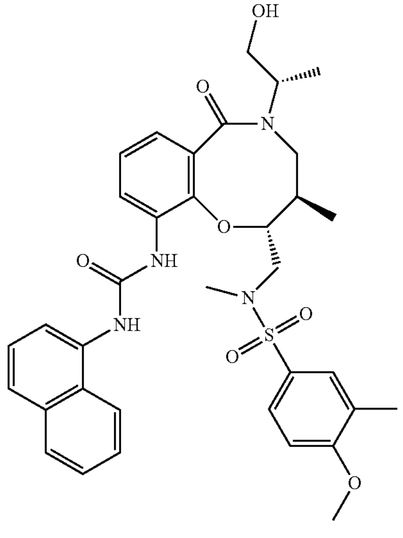

N-(((2R,3R)-5-((S)-1-hydroxypropan-2-yl)-3-methyl-10-(3-(naphthalen-1-yl)ureido)-6-oxo-3,4,5,6-tetrahydro-2H-benzo[b][1,5]oxazocin-2-yl)methyl)-4-methoxy-N,3-dimethylbenzenesulfonamide/Compound 20A/$EC_{50}$=0.314 uM Compound-20A was synthesized in the same manner as Compound-21A above except p-methoxy-m-methyl sulfonyl chloride was used in place of 2,3-dihydrobenzo[b][1,4]dioxine-6-sulfonyl chloride in the final reaction to yield the product as a white solid.

Example 3

Synthesis of Compound-1A

Compound 1A

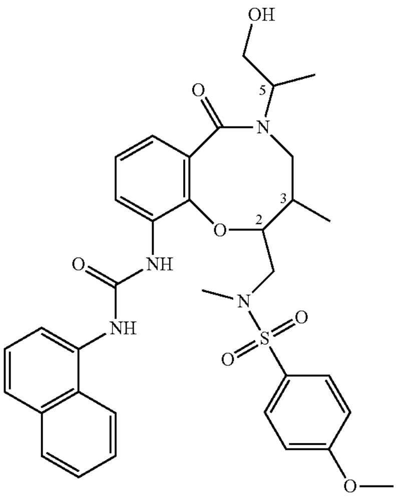

| Compound No. | Stereochemistry |
|---|---|
| 1A | 2R, 3R, 5S |
| 1B | 2S, 3S, 5R |
| 1C | 2R, 3R, 5R |
| 1D | 2S, 3S, 5S |
| 1E | 2R, 3S, 5S |
| 1F | 2S, 3R, 5R |
| 1G | 2R, 3S, 5R |
| 1H | 2S, 3R, 5S |

N-(((2R,3R)-5-((S)-1-hydroxypropan-2-yl)-3-methyl-10-(3-(naphthalen-1-yl)ureido)-6-oxo-3,4,5,6-tetrahydro-2H-benzo[b][1,5]oxazocin-2-yl)methyl)-4-methoxy-N-methylbenzenesulfonamide/Compound-1A/$EC_{50}$=0.423 μM Compound-1A was synthesized in the same manner as Compound-21A above except p-methoxy sulfonyl chloride was used in place of 2,3-dihydrobenzo[b][1,4]dioxine-6-sulfonyl chloride in the final reaction to yield the product as a white solid.

Example 4

Synthesis of Compound-2A

Compound-2A

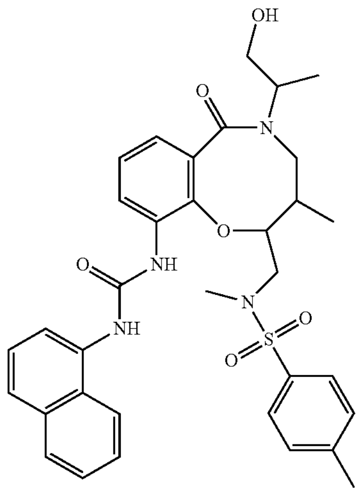

| Compound No. | Stereochemistry |
|---|---|
| 2A | 2R, 3R, 5S |
| 2B | 2R, 3R, 5R |

N-(((2R,3R)-5-((S)-1-hydroxypropan-2-yl)-3-methyl-10-(3-(naphthalen-1-yl)ureido)-6-oxo-3,4,5,6-tetrahydro-2H-benzo[b][1,5]oxazocin-2-yl)methyl)-N,4-dimethylbenzenesulfonamide/Compound-2A/$EC_{50}$=5.5 uM Compound-2A was synthesized in the same manner as Compound-21A above except p-methyl sulfonyl chloride was used in place of 2,3-dihydrobenzo[b][1,4]dioxine-6-sulfonyl chloride in the final reaction to yield the product as a white solid.

Compound 3

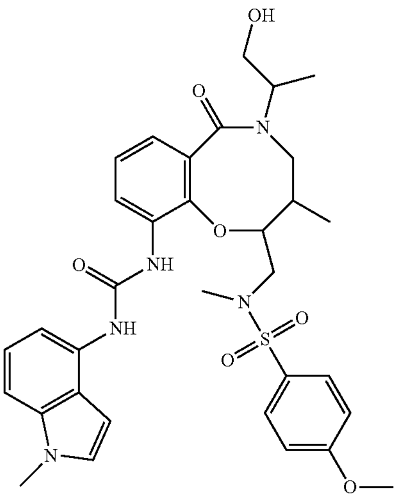

Compound 3A

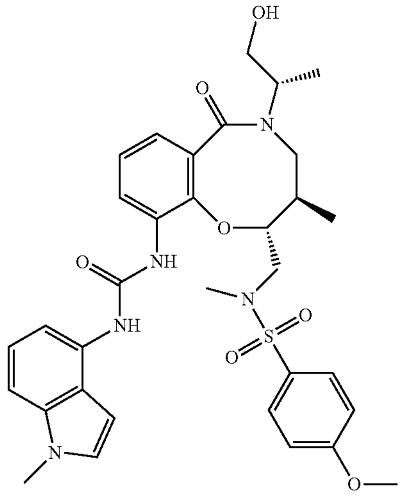

N-(((2R,3R)-5-((S)-1-hydroxypropan-2-yl)-3-methyl-10-(3-(1-methyl-1H-indol-4-yl)ureido)-6-oxo-3,4,5,6-tetrahydro-2H-benzo[b][1,5]oxazocin-2-yl)methyl)-N,4-dimethylbenzenesulfonamide/Compound-3A Compound 3A was synthesized using a procedure similar to the synthesis of Compound-21A described above.

Compound 30A

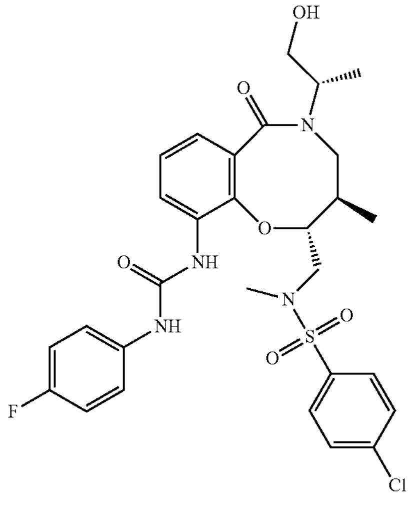

4-Chloro-N-(((2R,3R)-10-(3-(4-fluorophenyl)ureido)-5-((S)-1-hydroxypropan-2-yl)-3-methyl-6-oxo-3,4,5,6-tetrahydro-2H-benzo[b][1,5]oxazocin-2-yl)methyl)-N-methylbenzenesulfonamide Compound-30A was synthesized in the same manner as Compound-21A above except that p-fluorobenzene isocyanate was used in place of 1-isocyanatonaphthalene in the reaction with the aniline and p-chloro sulfonyl chloride was used in place of 2,3-dihydrobenzo[b][1,4]dioxine-6-sulfonyl chloride in the final reaction to yield the product as a white solid.

Compound 32A

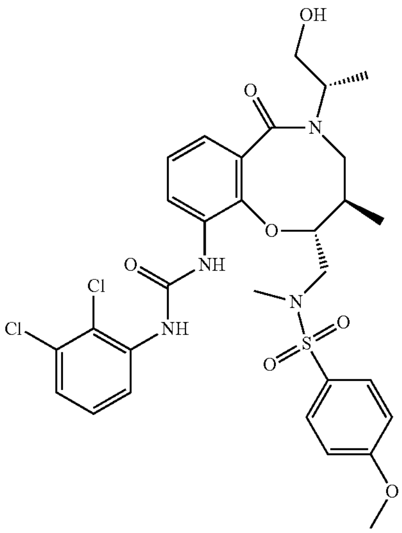

N-(((2R,3R)-10-(3-(2,3-Dichlorophenyl)ureido)-5-((S)-1-hydroxypropan-2-yl)-3-methyl-6-oxo-3,4,5,6-tetrahydro-2H-benzo[b][1,5]oxazocin-2-yl)methyl)-4-methoxy-N-methylbenzenesulfonamide Compound-32A was synthesized in the same manner as Compound-21A above except that o,m-dichlorobenzene isocyanate was used in place of 1-isocyanatonaphthalene in the reaction with the aniline and p-methoxy sulfonyl chloride was used in place of 2,3-dihydrobenzo[b][1,4]dioxine-6-sulfonyl chloride in the final reaction to yield the product as a white solid.

The compounds were analyzed for activity utilizing methods described in Chou et al. (ACS Chem. Biol. 2010 Aug. 20; 5(8):729-34).

Cell Culture and Reagents:

INS-1E cells (generously provided by C. Wollheim and P. Maechler, University of Geneva) were maintained in RPMI 1640 containing 11 mM glucose, 10% fetal bovine serum, 10 mM HEPES, 50 μM 2-mercaptoethanol, 1 mM sodium pyruvate, cultivated at 37° C. with 5% $CO_2$ in a humidified atmosphere, and split every week. Recombinant rat IL-1β and recombinant mouse TNF-α were purchased from R&D Systems. Recombinant mouse IFN-γ, Griess reagent, and dexamethasone were purchased from Sigma. CellTiter-Glo and Caspase-Glo 3/7 reagents were purchased from Promega. Alsterpaullone and Ro 31-8220 were purchased from EMD Biosciences. The pyrazole derivatives were purchased from Maybridge. CHIR99021 was synthesized as described in Wang et al. (Proc. Natl. Acad. Sci. U.S.A. 106, 1427-1432, 2009).

High-Throughput Screening for Compounds Affecting Cellular ATP Levels:

INS-1E cells were seeded at 10,000 cells per well using a Multidrop Combi (Thermo Labsystems) in white optical 384-well plates (Corning Life Sciences). After overnight incubation, medium was removed and 50 μL of RPMI containing 1% FBS and a combination of cytokines (10 ng $mL^{-1}$ IL-1β, 50 ng $mL^{-1}$ IFN-γ, 25 ng$mL^{-1}$ TNF-α) was added to every well. Using libraries of compounds dissolved in DMSO and a CyBi-Well pin-transfer robot (CyBio Corp.), 0.1 μL of each compound was added. After 48 h, medium was removed and 20 μL of CellTiter-Glo reagent was added. Luminescence was measured after 10 min of incubation using an EnVision plate reader (PerkinElmer).

Screening Data Analysis:

Instrument output files were processed using Pipeline Pilot (Accelrys) and input to MATLAB (The MathWorks) for data normalization. Compound performance scores relative to a distribution of mock-treated (DMSO) wells were calculated using a revised version of the scoring system underlying ChemBank. (Seiler et al., Nucleic Acids Res. 36, D351-359, 2008). The role of replicate treatments was further developed as follows: first, mock-treatment distributions were modeled using all mock-treated wells measured on a single day, regardless of their nominal replicate; second, per-compound scores weighted each in-plate background-subtracted measurement by the uncertainty in that measurement, using the method of maximum likelihood. The uncertainty in a single background-subtracted measurement was estimated using the number of mock-treated wells on the plate and, as a measure of the assay noise, the standard deviation of the per-day mock-treatment distribution. The signal, a weighted average of differences, was scaled by the noise, the standard deviation of the mock treatment distribution.

Measurement of Cellular Nitrite Production:

INS-1E cells were seeded and treated as described for high-throughput screening. After treatment with cytokine and compounds for 48 h, 10 μL of modified Griess reagent (1:1 mixture of 1% sulfanilamide in 30% acetic acid and 0.1% N-(1-naphthyl)ethylenediamine dihydrochloride in 60% acetic acid) was added to each well. After 5 min of incubation at RT, the absorbance at 540 nm was measured using an EnVision (Perkin Elmer) plate reader.

Caspase-3 Activity Assay:

INS-1E cells were seeded at 5,000 cells per well in white optical 384-well plates and treated as described for highthroughput screening. After treatment with cytokines and compounds for 48 h, medium was removed and 20 μL Caspase-Glo 3/7 reagent was added. Luminescence was measured after 2 h of incubation using an EnVision plate reader. The data from the screening is tabulated in Table 3 below.

Glucose-Stimulated Insulin Secretion:

INS-1E cells were seeded in 96-well plates at 20,000 cells per well and incubated for 48 h in 100 μL of fresh RPMI containing 1% FBS and the cytokine cocktail, in the presence or absence of compounds. Cells were washed and incubated for 2 h in KRBH (135 mM NaCl, 3.6 mM KCl, 5 mM $NaHCO_3$, 0.5 mM $NaH_2PO_4$, 0.5 mM $MgCl_2$, 1.5 mM $CaCl_2$, 10 mM HEPES, pH 7.4, 0.1% BSA) without glucose. Cells were subsequently incubated with KRBH containing 2 or 15 mM glucose for 1 h. The supernatant was taken for measurement of released insulin, and 100 μL of acidified ethanol was added to each well for extraction and measurement of cellular insulin content. Insulin was measured with a rat insulin ELISA kit (Alpco).

The activity data for some of the compounds of the invention is tabulated in Table 3 below. In these assays, the following grading was used: I>0.1 μM; II>10 μM; III>20 μM; IV>25 μM.

TABLE 3

| Compound No. | CTG $EC_{50}$ in HTS (μM) | Caspase $EC_{50}$ (μM) |
|---|---|---|
| 1A | I | I |
| 1B | IV | IV |
| 1C | III | IV |
| 1D | III | IV |

TABLE 3-continued

| Compound No. | CTG $EC_{50}$ in HTS (μM) | Caspase $EC_{50}$ (μM) |
|---|---|---|
| 1E | IV | IV |
| 1F | III | IV |
| 1G | IV | IV |
| 1H | NT | NT |
| 2A | II | IV |
| 2B | III | III |
| 3A | IV | II |
| 4A | IV | IV |
| 5A | I | IV |
| 6A | IV | IV |
| 7A | IV | IV |
| 8A | IV | IV |
| 9A | IV | IV |
| 10A | III | IV |
| 11A | II | IV |
| 12A | IV | IV |
| 13A | IV | IV |
| 14A | IV | IV |
| 15A | IV | IV |
| 16A | II | IV |
| 17A | IV | IV |
| 18A | IV | IV |
| 19A | IV | IV |
| 20A | I | I |
| 21A | I | II |
| 22A | NA | NA |
| 23A | IV | IV |
| 24A | IV | IV |
| 25A | IV | IV |
| 26A | IV | IV |
| 27A | IV | IV |
| 28A | NT | NT |
| 29A | NT | NT |
| 30A | IV | IV |
| 31A | III | III |
| 32A | III | IV |
| 33A | IV | IV |
| 34A | IV | IV |
| 35A | IV | IV |
| 36A | IV | IV |
| 37A | IV | IV |
| 37B | IV | |
| 38A | IV | IV |
| 39A | IV | IV |
| 40A | IV | IV |
| 41A | IV | IV |
| 42A | IV | IV |
| 43A | IV | IV |
| 44A | IV | IV |
| 45A | IV | IV |
| 46A | IV | IV |
| 47A | IV | IV |
| 48A | IV | IV. |

IA = Inactive
NA = Not Applicable
NT = Not Tested.

Measurement of Cellular ATP Levels.

INS-1E cells were seeded at 10,000 cells/well using a Multidrop Combi (Thermo Labsystems) in white optical 384-well plates (Corning Life Sciences). After overnight incubation, medium was removed and 50 μL RPMI containing the treated compound, 1% FBS and a combination of cytokines (10 ng/mL IL-1β, 50 ng/mL IFN-γ, 25 ng/mL TNF-α) was added to every well. After incubation for 48 hr, medium was removed and 20 μL CellTiter-Glo reagent was added. Luminescence was measured after 10-min incubation using an EnVision plate reader (PerkinElmer).

Gene-Expression Profiling and Gene-Set Enrichment Analysis (GSEA).

We performed gene-expression profiling on INS-1E cells using the Affymetrix Rat 230 2.0 array. Data normalization and gene-set enrichment analysis (GSEA) were performed using GenePattern (http://genepattern.broadinstitute.org) as described in Subramanian A et al. (2005) *Proc. Natl. Acad. Sci. USA* 102:15545-15550.

GAS Reporter Assay.

INS-1E cells were transfected with plasmids (GAS reporter assay kit) using DharmaFECT reagent according to the manufacturer's protocol (SABiosciences) in white optical 384-well plates (Corning Life Sciences). After overnight incubation, medium was removed and 50 μL RPMI containing the treated compound, 1% FBS and a combination of cytokines (10 ng/mL IL-1β, 50 ng/mL IFN-γ, 25 ng/mL TNF-α) was added to every well. After treatment with cytokines and compounds for 18 hr, luminescence was measure using Dual-Glo according to the manufacturer's protocol (Promega).

RNA Interference and Western Blotting.

siRNAs (100 nM) were transfected into INS-1E cells (5,000 cells/well in a 384-well plate) using DharmaFECT reagent. Transfected cells were cultured for 72 hr, then collected for Western blot analysis and cell-based assays. For Western blotting, cells were lysed in RIPA buffer. Total protein was separated by 4-12% SDS-PAGE and transferred to a PVDF membrane. Blots were developed using the chemiluminescence detection system SuperSignal (Thermo Fisher Scientific) and light emission was captured using an Imaging Station 4000MM (Carestream).

Quantitative PCR for mRNA Levels.

Following knock-down by siRNA, cells were lysed and RNA was isolated using the RNeasy Mini Kit (Qiagen) according to the manufacturer's protocol. RNA was reverse transcribed with random primers using the High Capacity cDNA Reverse Transcription Kit with RNase inhibitor (Applied Biosystems). Quantitative PCR was performed with Power SYBR Green PCR Master Mix (Applied Biosystems) on an Applied Biosystems 7900HT real-time PCR machine using primers for rat Mcm6 and Blvrb from SABiociences.

Kinase Profiling.

Kinase profiling was performed by Millipore (KinaseProfiler) according to the manufacturer's protocols. ATP concentrations were within 15 μM of the apparent KM for each enzyme.

SILAC and Mass Spectrometry.

We performed stable isotope labeling of amino acids in cell culture (SILAC) on INS-1E cells, followed by mass spectrometry to identify proteins enriched in the absence of soluble BRD0476 competitor, as described in Ong S E et al. (2009) *Proc. Natl. Acad. Sci. USA* 106:4617-4622.

Purification of Recombinant USP9X.

For each purification, fifty 25-cm dishes of confluent HEK-293 cell lines stably expressing wild-type USP-9X (provided by Dr. Dario Alessi, University of Dundee, Scotland) were employed. Cells were washed twice with ice-cold PBS and lysed in 1 ml of ice-cold lysis buffer. The combined lysates were centrifuged at 26000 g for 30 min at 4° C. and the supernatant incubated with 0.2 ml of rabbit IgG-agarose beads (Sigma) for 1 h at 4° C. The IgG-agarose was washed extensively with lysis buffer containing 0.15 M NaCl, then with several washes in buffer B prior to incubation with 0.250 ml of buffer B containing 0.1 mg of TEV protease (Invitrogen). After 3 h at 4° C.~70-90% of the TAP-tagged protein had been cleaved from the IgG-agarose and the eluted protein was incubated with 0.1 ml of rabbit calmodulin-Sepharose (Roche) equilibrated in buffer C. After 1 h at 4° C., the calmodulin-Sepharose was washed with buffer C. To elute the protein, the calmodulin-Sepharose was then incubated with 0.1 ml of buffer D for 10 min at 4° C. The eluate was removed from the beads and the elution repeated two or three times. To remove the NaCl present in the buffer containing the eluate protein, the eluates were centrifuged at 1500 g for 1 min at 4° C. in protein desalting spin columns. Lysis buffer contained 50 mM Tris/HCl (pH 7.5), 1 mM EGTA, 1 mM EDTA, 1% (w/v) Nonidet P40, 1 mM sodium orthovanadate, 10 mM sodium b-glycerophosphate, 50 mM sodium fluoride, 5 mM sodium pyrophosphate, 0.27 M sucrose, 1 mM DTT (dithiothreitol) and complete proteinase inhibitor cocktail (one tablet/50 ml). Buffer B contained 50 mM Tris/HCl (pH 7.5), 0.15 M NaCl, 0.27 M sucrose, 1% (w/v) Nonidet P40 and 1 mM DTT. Buffer C contained 50 mM Tris/HCl (pH 7.5), 0.15 M NaCl, 1 mM $MgCl_2$, 1 mM imidazole, 2 mM $CaCl_2$, 0.27 M sucrose and 1 mM DTT. Buffer D contained 50 mM Tris/HCl (pH 7.5), 20 mM EGTA, 150 mM NaCl and 5 mM DTT. TBS-Tween buffer contained 50 mM Tris/HCl (pH 7.5), 0.15 M NaCl and 0.2% (v/v) Tween 20.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of Formula I or a prodrug or metabolite thereof;

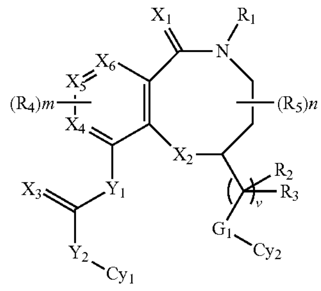

wherein, each $X_1$ and $X_3$ is independently —O— or —S—;

each $X_4$, $X_5$ and $X_6$ is independently —CH or —N—;

each $X_2$, $Y_1$ and $Y_2$ is independently —$NR_{10}$, —S— or —O—;

$Cy_1$ is an optionally substituted aryl group;

$Cy_2$ is an optionally substituted cycloalkyl, optionally substituted cycloalkenyl, optionally substituted heterocyclyl or optionally substituted aryl containing one, two or three rings;

$R_1$ is hydrogen, halogen, aliphatic, substituted aliphatic, aryl or substituted aryl;

each $R_2$, $R_3$, $R_4$ and $R_5$ is independently selected from absent, hydrogen, halogen, —$OR_{10}$, —$SR_{10}$, —$NR_{10}R_{11}$, —$C(O)R_{10}$, —$C(O)OR_{10}$, —$C(O)NR_{10}R_{11}$, —$N(R_{10})C(O)R_{11}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, optionally substituted aliphatic, optionally substituted aryl or optionally substituted heterocyclyl;

$G_1$ is —$N(R_{10})C(O)$—, —$N(R_{10})C(S)$—, —$N(R_{10})S(O)_2$—, —$N(R_{10})S(O)_2$—$[C(R_{10})(R_{11})]_W$—, —$N(R—_{10})C(O)$—$[C(R_{10})(R_{11})]_W$—, —$N(R_{10})C(S)$—$[C(R_{10})(R_{11})]_W$—, —$N(R_{10})C(O)N(R_{11})$—, —$N(R—_{10})C(S)N(R_{11})$—, —C(O)O— or —C(O)O—$[C(R_{10})(R_{11})]_W$—;

each n and m is independently selected from 0, 1, 2 or 3;

each v and w is independently selected from 0, 1, 2, 3, 4, 5 or 6;

each $R_{10}$, $R_{11}$, $R_{12}$, $R_{13}$ and $R_{14}$ is independently absent, hydrogen, halogen, OH, —SH, —$NH_2$, —$CF_3$, —CN, —$NO_2$, —$N_3$, —C(O)OH, —C(O)$NH_2$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two of $R_{10}$, $R_{11}$, $R_{12}$, $R_{13}$ and $R_{14}$ together with the atoms to which they are attached and any intervening atoms may form an additional optionally substituted, 3, 4, 5, 6 or 7 membered ring.

2. A compound of claim 1, wherein $Cy_1$ is selected from;

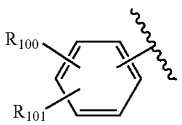
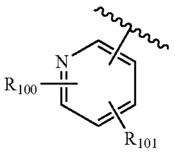
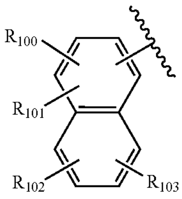
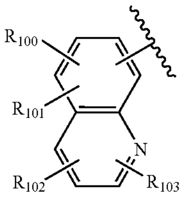
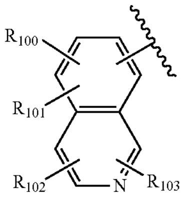
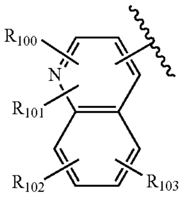
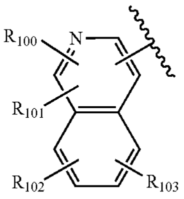
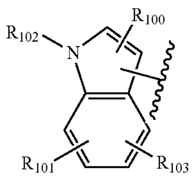
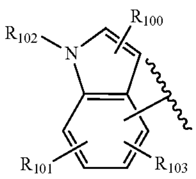

wherein each $R_{100}$, $R_{101}$, $R_{102}$ and $R_{103}$ is independently absent, hydrogen, halogen, —$OR_{10}$, —$SR_{11}$, —$NR_{10}R_{11}$, —C(O)$R_{10}$, —C(O)$OR_{10}$, —C(O)$NR_{10}R_{11}$, —N($R_{10}$)C(O)$R_{11}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl.

3. A compound of claim 1, wherein $Cy_2$ is selected from:

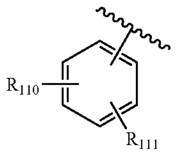
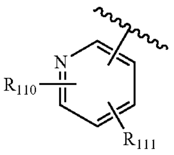
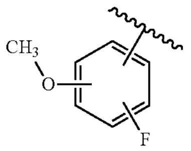
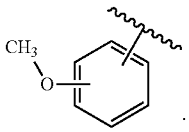
.

4. A compound of claim 1, wherein $X_1$ is —O— or $X_2$ is —O— or $X_3$ is —O— or $X_5$ is —CH or $X_6$ is —CH or $Y_1$ is —NH or $Y_2$ is —NH or $G_1$ is —N(H)S(O)$_2$—.

5. A compound of claim 1, wherein n is 1, and $R_5$ is —$CH_3$.

6. A compound of claim 1, wherein m is 0.

7. A compound of claim 1, wherein $R_1$ is hydroxyl substituted alkyl.

8. A compound of claim 1, wherein $R_2$ and $R_3$ are hydrogen and v is 1.

9. A compound of claim 1, wherein $Cy_1$ is naphthyl.

10. A compound of claim 1, wherein $Cy_2$ is an optionally substituted aryl.

11. A compound selected from Table A, or a pharmaceutically acceptable prodrug or metabolite thereof:

TABLE A

| No. | Compound |
|---|---|
| 1 | 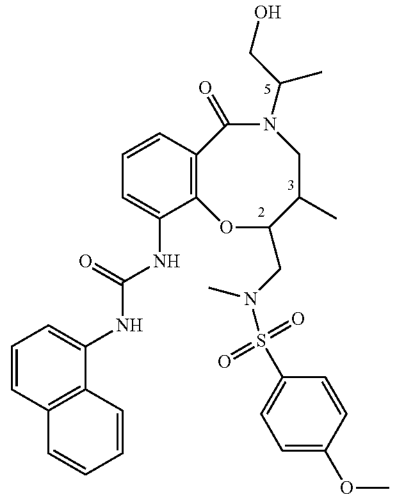 [SMILES: COc1ccc(S(=O)(=O)N(C)CC2Oc3c(NC(=O)Nc4cccc5ccccc45)cccc3C(=O)N(C(C)CO)CC2C)cc1] |

TABLE A-continued
| No. | Compound |
| --- | --- |
| 2 | 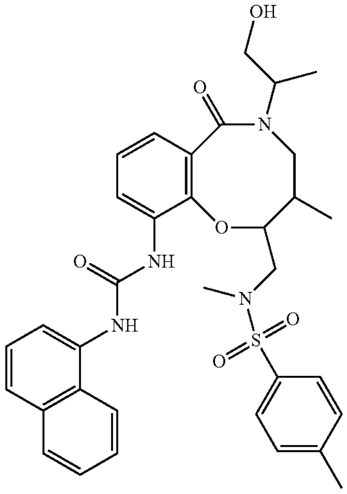 [SMILES: Cc1ccc(S(=O)(=O)N(C)CC2Oc3c(NC(=O)Nc4cccc5ccccc45)cccc3C(=O)N(C(C)CO)CC2C)cc1] |
| 3 | 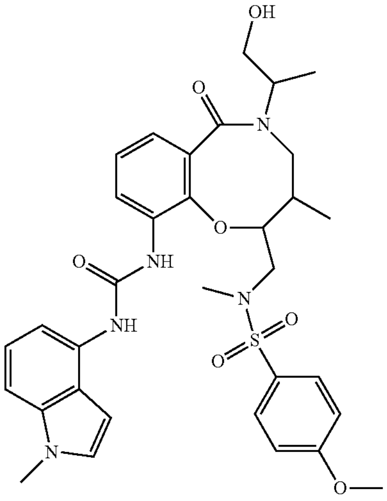 [SMILES: COc1ccc(S(=O)(=O)N(C)CC2Oc3c(NC(=O)Nc4cccc5c4ccn5C)cccc3C(=O)N(C(C)CO)CC2C)cc1] |
| 4 | 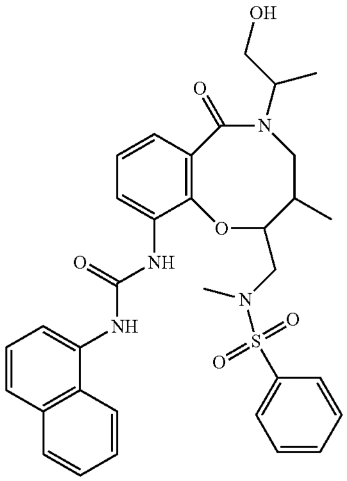 [SMILES: CC1CN(C(C)CO)C(=O)c2cccc(NC(=O)Nc3cccc4ccccc34)c2OC1CN(C)S(=O)(=O)c1ccccc1] |
| 5 | 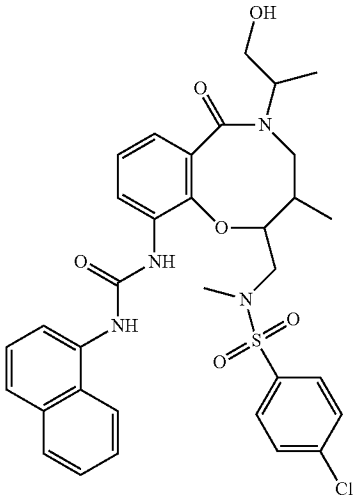 [SMILES: CC1CN(C(C)CO)C(=O)c2cccc(NC(=O)Nc3cccc4ccccc34)c2OC1CN(C)S(=O)(=O)c1ccc(Cl)cc1] |
| 6 | 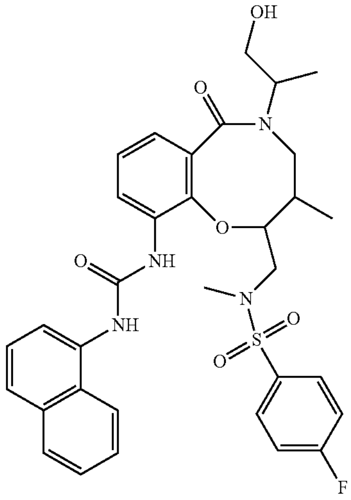 [SMILES: CC1CN(C(C)CO)C(=O)c2cccc(NC(=O)Nc3cccc4ccccc34)c2OC1CN(C)S(=O)(=O)c1ccc(F)cc1] |
| 7 | 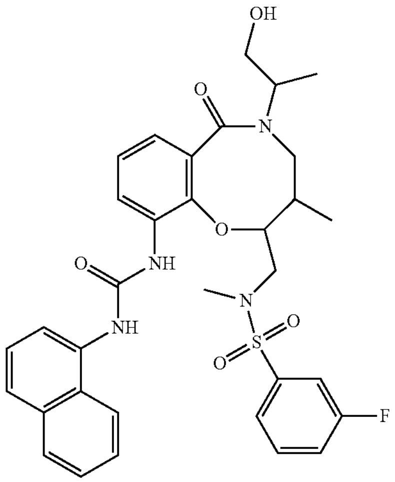 [SMILES: CC1CN(C(C)CO)C(=O)c2cccc(NC(=O)Nc3cccc4ccccc34)c2OC1CN(C)S(=O)(=O)c1cccc(F)c1] |

TABLE A-continued
| No. | Compound |
|---|---|
| 8 | 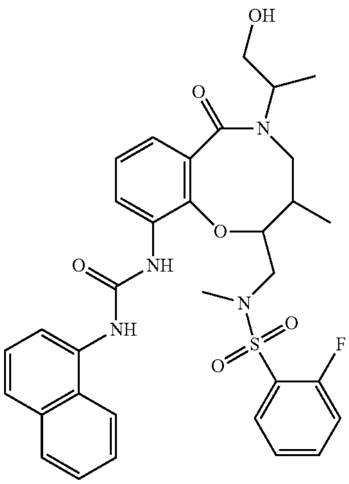 [SMILES: CC1CN(C(C)CO)C(=O)c2cccc(NC(=O)Nc3cccc4ccccc34)c2OC1CN(C)S(=O)(=O)c1ccccc1F] |
| 9 | 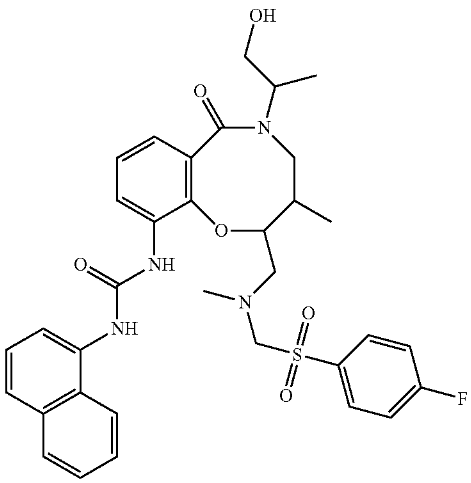 [SMILES: CC1CN(C(C)CO)C(=O)c2cccc(NC(=O)Nc3cccc4ccccc34)c2OC1CN(C)CS(=O)(=O)c1ccc(F)cc1] |
| 10 | 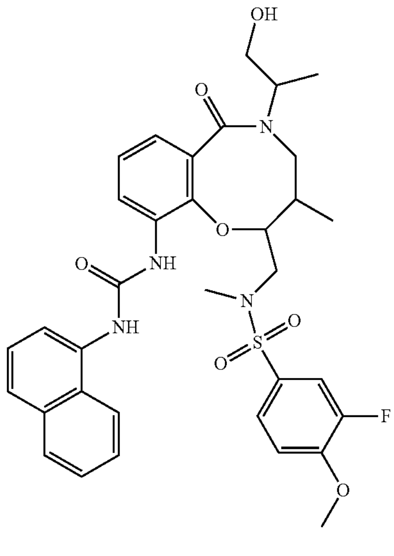 [SMILES: COc1ccc(S(=O)(=O)N(C)CC2Oc3c(NC(=O)Nc4cccc5ccccc45)cccc3C(=O)N(C(C)CO)CC2C)cc1F] |
TABLE A-continued
| No. | Compound |
|---|---|
| 11 | 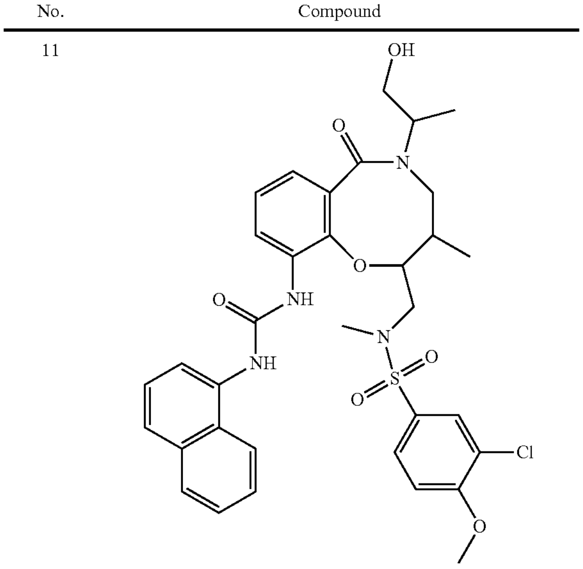 |
| 12 | 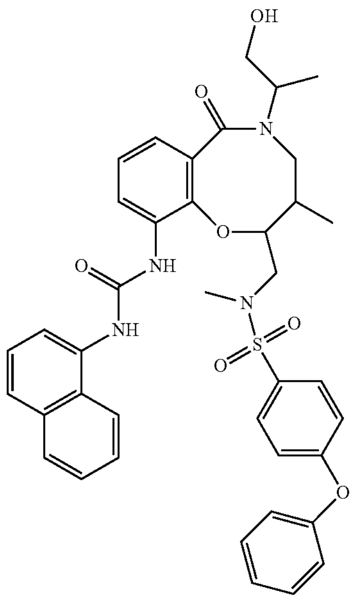 [SMILES: CC1CN(C(C)CO)C(=O)c2cccc(NC(=O)Nc3cccc4ccccc34)c2OC1CN(C)S(=O)(=O)c1ccc(Oc2ccccc2)cc1] |

TABLE A-continued
| No. | Compound |
|---|---|
| 13 | 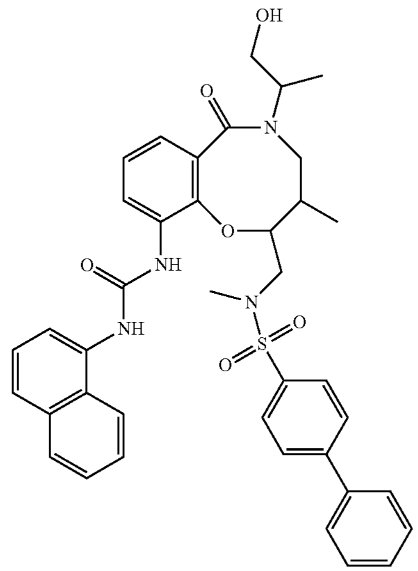 [SMILES: CC1CN(C(C)CO)C(=O)c2cccc(NC(=O)Nc3cccc4ccccc34)c2OC1CN(C)S(=O)(=O)c1ccc(-c2ccccc2)cc1] |
| 14 | 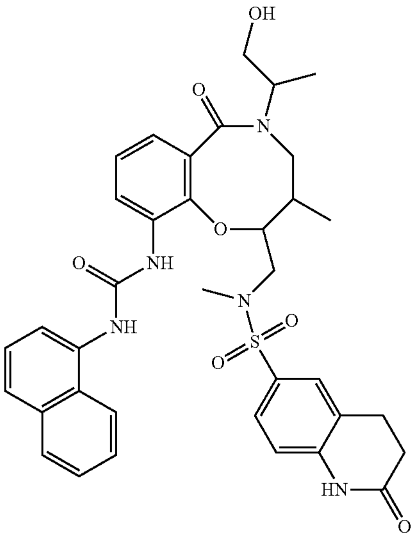 [SMILES: CC1CN(C(C)CO)C(=O)c2cccc(NC(=O)Nc3cccc4ccccc34)c2OC1CN(C)S(=O)(=O)c1ccc2c(c1)CCC(=O)N2] |
| 15 | 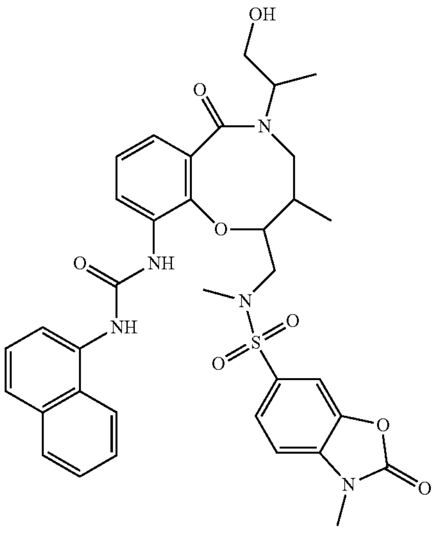 [SMILES: CC1CN(C(C)CO)C(=O)c2cccc(NC(=O)Nc3cccc4ccccc34)c2OC1CN(C)S(=O)(=O)c1ccc2c(c1)oc(=O)n2C] |
TABLE A-continued
| No. | Compound |
|---|---|
| 16 | 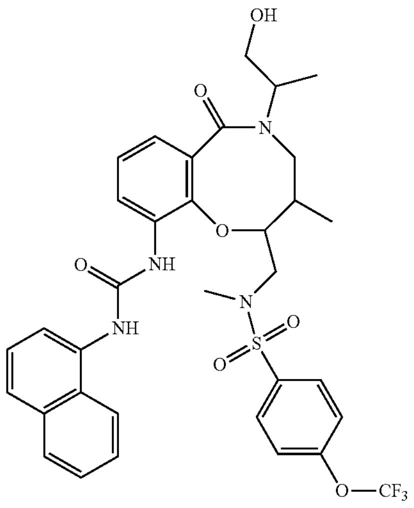 [SMILES: CC1CN(C(C)CO)C(=O)c2cccc(NC(=O)Nc3cccc4ccccc34)c2OC1CN(C)S(=O)(=O)c1ccc(OC(F)(F)F)cc1] |
| 17 | 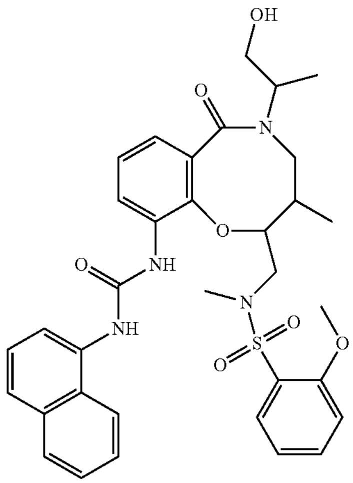 [SMILES: COc1ccccc1S(=O)(=O)N(C)CC1Oc2c(NC(=O)Nc3cccc4ccccc34)cccc2C(=O)N(C(C)CO)CC1C] |
| 18 | 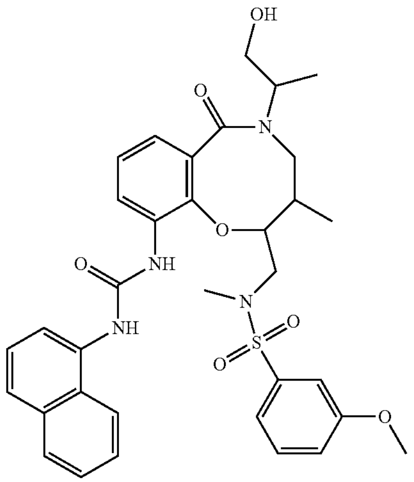 [SMILES: COc1cccc(S(=O)(=O)N(C)CC2Oc3c(NC(=O)Nc4cccc5ccccc45)cccc3C(=O)N(C(C)CO)CC2C)c1] |

TABLE A-continued
| No. | Compound |
|---|---|
| 19 | 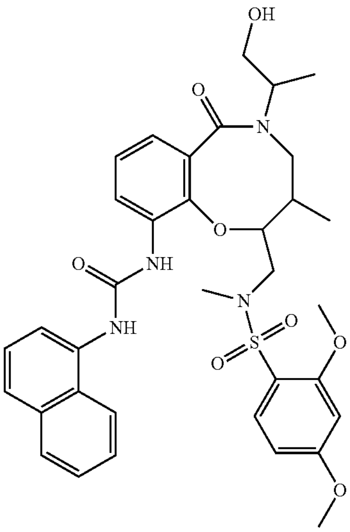 [SMILES: COc1ccc(S(=O)(=O)N(C)CC2Oc3c(NC(=O)Nc4cccc5ccccc45)cccc3C(=O)N(C(C)CO)CC2C)c(OC)c1] |
| 20 | 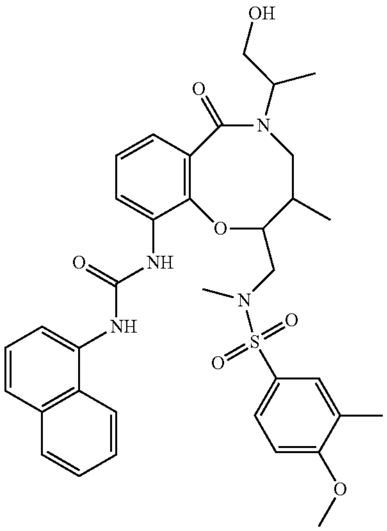 [SMILES: COc1ccc(S(=O)(=O)N(C)CC2Oc3c(NC(=O)Nc4cccc5ccccc45)cccc3C(=O)N(C(C)CO)CC2C)cc1C] |
| 21 | 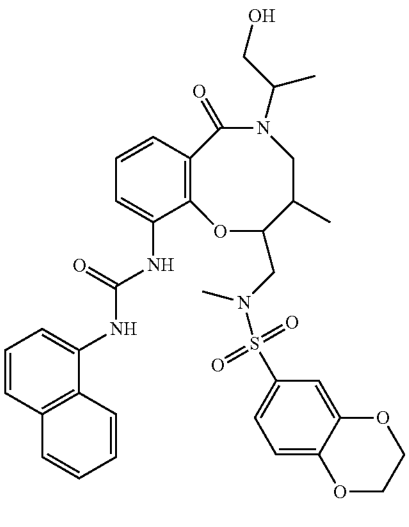 [SMILES: CC1CN(C(C)CO)C(=O)c2cccc(NC(=O)Nc3cccc4ccccc34)c2OC1CN(C)S(=O)(=O)c1ccc2c(c1)OCCO2] |
TABLE A-continued
| No. | Compound |
|---|---|
| 22 | 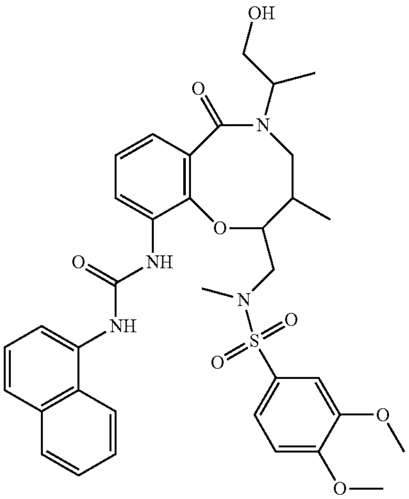 [SMILES: COc1ccc(S(=O)(=O)N(C)CC2Oc3c(NC(=O)Nc4cccc5ccccc45)cccc3C(=O)N(C(C)CO)CC2C)cc1OC] |
| 23 | 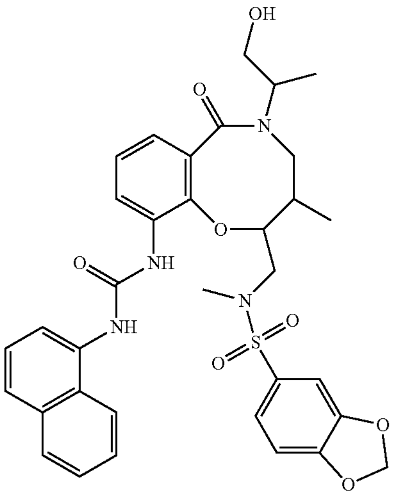 [SMILES: CC1CN(C(C)CO)C(=O)c2cccc(NC(=O)Nc3cccc4ccccc34)c2OC1CN(C)S(=O)(=O)c1ccc2c(c1)OCO2] |
| 24 | 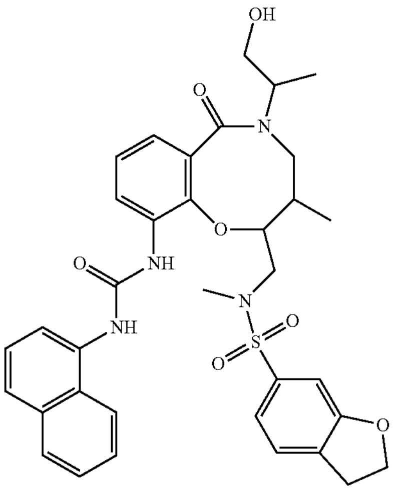 [SMILES: CC1CN(C(C)CO)C(=O)c2cccc(NC(=O)Nc3cccc4ccccc34)c2OC1CN(C)S(=O)(=O)c1ccc2c(c1)OCC2] |

TABLE A-continued
| No. | Compound |
| --- | --- |
| 25 | 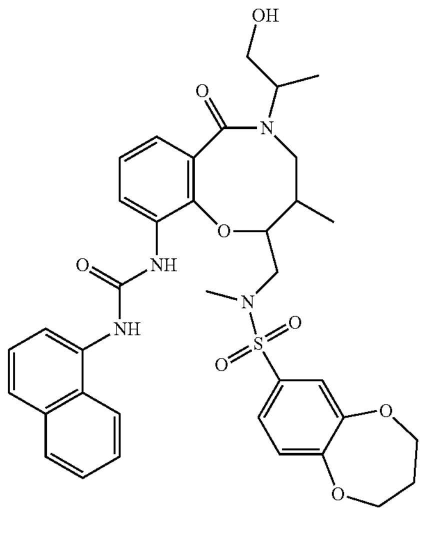 [SMILES: CC1CN(C(C)CO)C(=O)c2cccc(NC(=O)Nc3cccc4ccccc34)c2OC1CN(C)S(=O)(=O)c1ccc2c(c1)OCCCO2] |
| 26 | 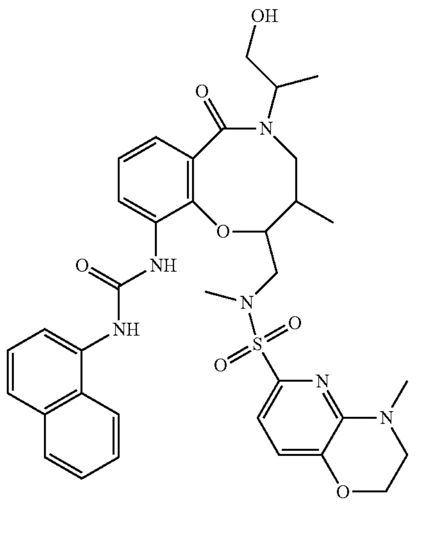 [SMILES: CC1CN(C(C)CO)C(=O)c2cccc(NC(=O)Nc3cccc4ccccc34)c2OC1CN(C)S(=O)(=O)c1ccc2c(n1)N(C)CCO2] |
| 27 | 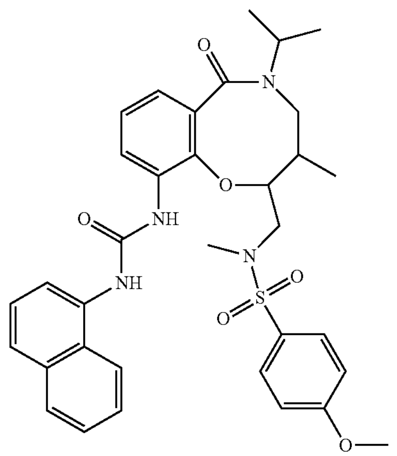 [SMILES: COc1ccc(S(=O)(=O)N(C)CC2Oc3c(NC(=O)Nc4cccc5ccccc45)cccc3C(=O)N(C(C)C)CC2C)cc1] |
TABLE A-continued
| No. | Compound |
| --- | --- |
| 28 | 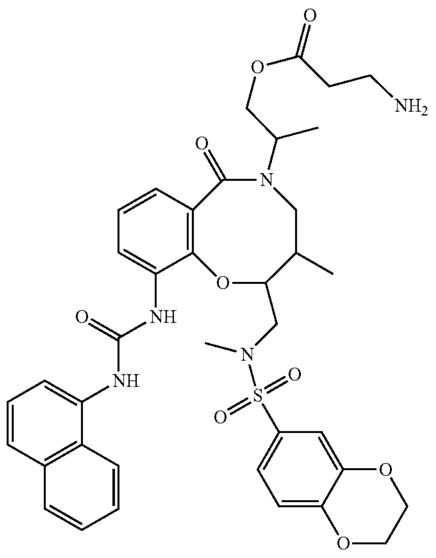 [SMILES: CC1CN(C(C)COC(=O)CCN)C(=O)c2cccc(NC(=O)Nc3cccc4ccccc34)c2OC1CN(C)S(=O)(=O)c1ccc2c(c1)OCCO2] |
| 29 | 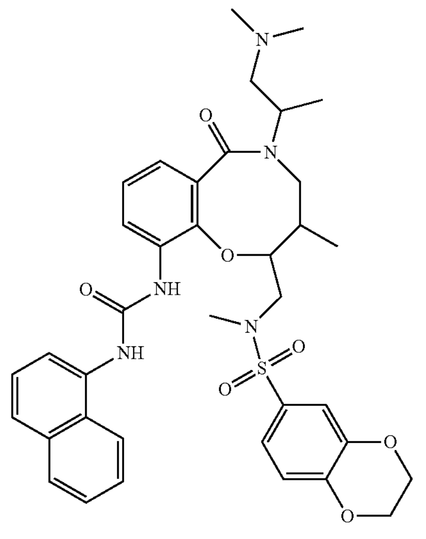 [SMILES: CC1CN(C(C)CN(C)C)C(=O)c2cccc(NC(=O)Nc3cccc4ccccc34)c2OC1CN(C)S(=O)(=O)c1ccc2c(c1)OCCO2] |
| 30 | 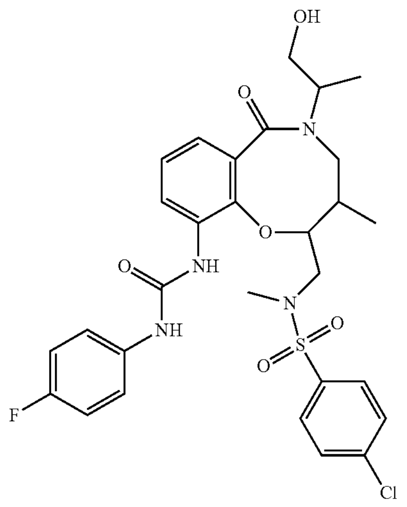 [SMILES: CC1CN(C(C)CO)C(=O)c2cccc(NC(=O)Nc3ccc(F)cc3)c2OC1CN(C)S(=O)(=O)c1ccc(Cl)cc1] |

TABLE A-continued
| No. | Compound |
| --- | --- |
| 31 | 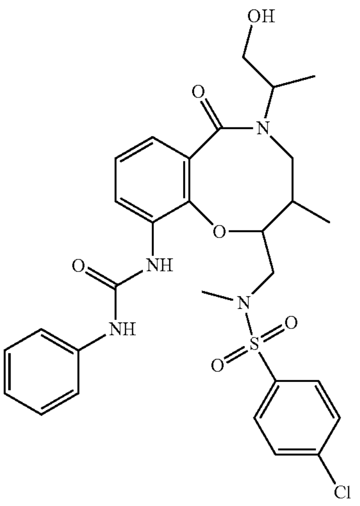 [SMILES: CC1CN(C(C)CO)C(=O)c2cccc(NC(=O)Nc3ccccc3)c2OC1CN(C)S(=O)(=O)c1ccc(Cl)cc1] |
| 32 | 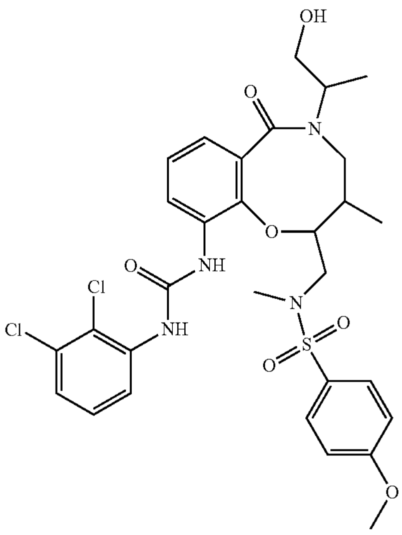 [SMILES: COc1ccc(S(=O)(=O)N(C)CC2Oc3c(NC(=O)Nc4cccc(Cl)c4Cl)cccc3C(=O)N(C(C)CO)CC2C)cc1] |
| 33 | 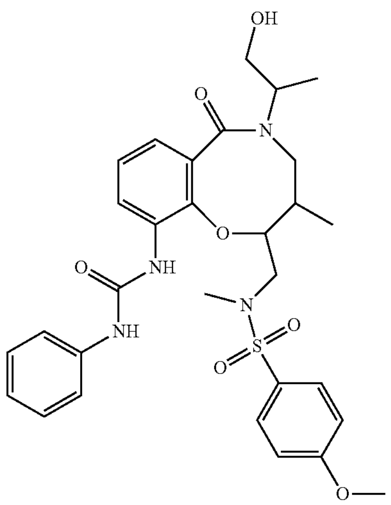 [SMILES: COc1ccc(S(=O)(=O)N(C)CC2Oc3c(NC(=O)Nc4ccccc4)cccc3C(=O)N(C(C)CO)CC2C)cc1] |
TABLE A-continued
| No. | Compound |
| --- | --- |
| 34 | 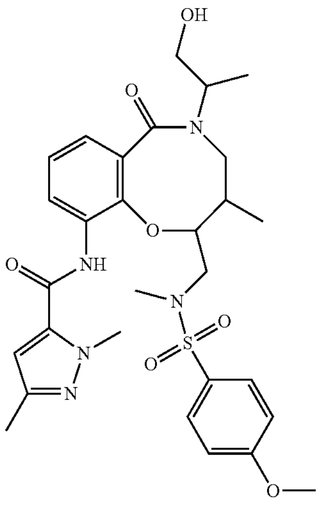 |
| 35 | 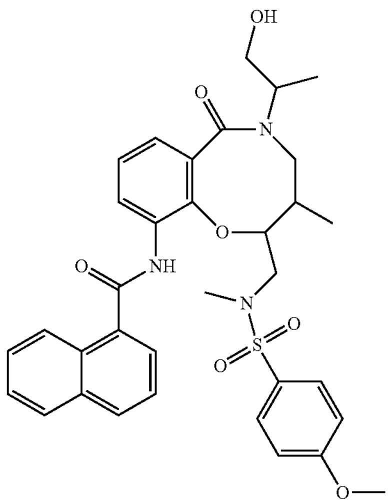 [SMILES: COc1ccc(S(=O)(=O)N(C)CC2Oc3c(NC(=O)c4cccc5ccccc45)cccc3C(=O)N(C(C)CO)CC2C)cc1] |
| 36 | 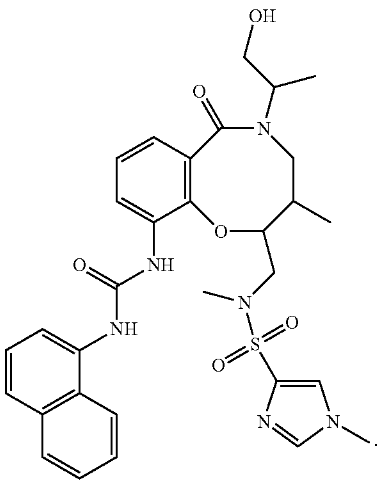 [SMILES: CC1CN(C(C)CO)C(=O)c2cccc(NC(=O)Nc3cccc4ccccc34)c2OC1CN(C)S(=O)(=O)c1cn(C)cn1] |
12. A compound selected from Table B, or a pharmaceutically acceptable prodrug or metabolite thereof:

TABLE B
| No. | Compound |
| --- | --- |
| 1A | 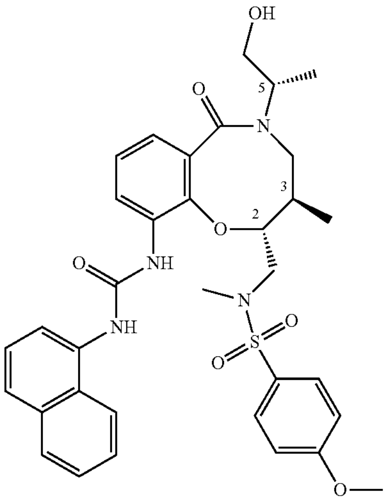 [SMILES: COc1ccc(S(=O)(=O)N(C)C[C@@H]2Oc3c(NC(=O)Nc4cccc5ccccc45)cccc3C(=O)N([C@@H](C)CO)C[C@H]2C)cc1] |
| 2A | 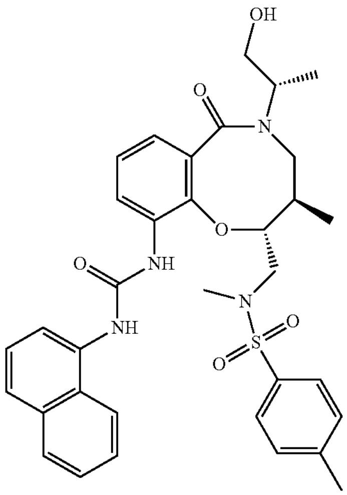 [SMILES: Cc1ccc(S(=O)(=O)N(C)C[C@@H]2Oc3c(NC(=O)Nc4cccc5ccccc45)cccc3C(=O)N([C@@H](C)CO)C[C@H]2C)cc1] |
| 3A | 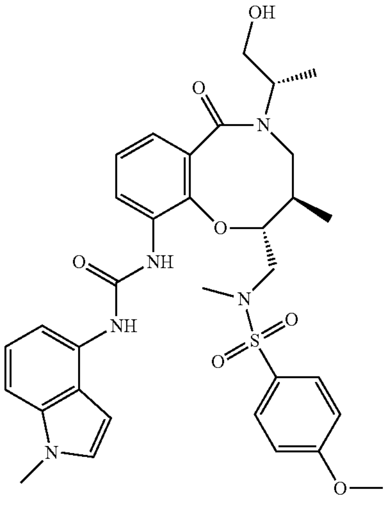 [SMILES: COc1ccc(S(=O)(=O)N(C)C[C@@H]2Oc3c(NC(=O)Nc4cccc5c4ccn5C)cccc3C(=O)N([C@@H](C)CO)C[C@H]2C)cc1] |
TABLE B-continued
| No. | Compound |
| --- | --- |
| 4A | 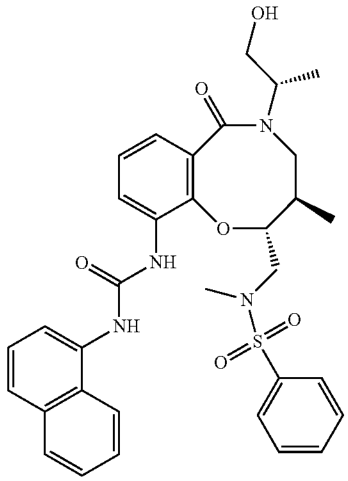 [SMILES: C[C@@H]1CN([C@@H](C)CO)C(=O)c2cccc(NC(=O)Nc3cccc4ccccc34)c2O[C@H]1CN(C)S(=O)(=O)c1ccccc1] |
| 5A | 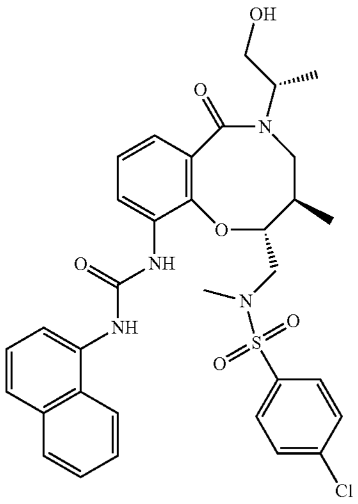 [SMILES: C[C@@H]1CN([C@@H](C)CO)C(=O)c2cccc(NC(=O)Nc3cccc4ccccc34)c2O[C@H]1CN(C)S(=O)(=O)c1ccc(Cl)cc1] |
| 6A | 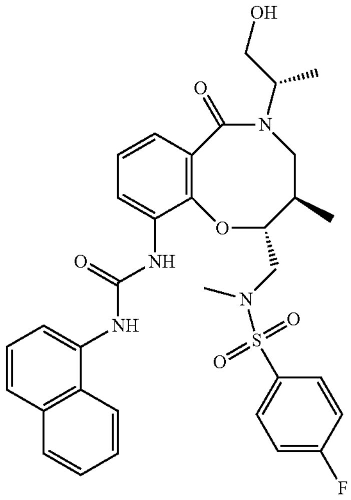 [SMILES: C[C@@H]1CN([C@@H](C)CO)C(=O)c2cccc(NC(=O)Nc3cccc4ccccc34)c2O[C@H]1CN(C)S(=O)(=O)c1ccc(F)cc1] |

TABLE B-continued
| No. | Compound |
|---|---|
| 7A | 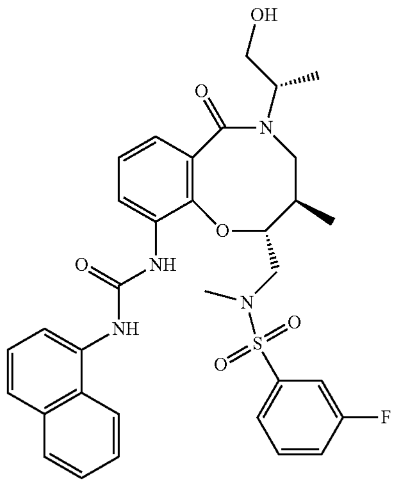 [SMILES: C[C@@H]1CN([C@@H](C)CO)C(=O)c2cccc(NC(=O)Nc3cccc4ccccc34)c2O[C@H]1CN(C)S(=O)(=O)c1cccc(F)c1] |
| 8A | 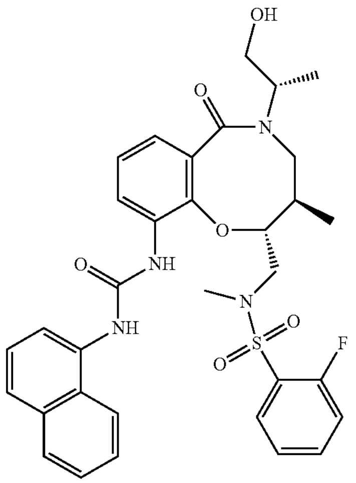 [SMILES: C[C@@H]1CN([C@@H](C)CO)C(=O)c2cccc(NC(=O)Nc3cccc4ccccc34)c2O[C@H]1CN(C)S(=O)(=O)c1ccccc1F] |
| 9A | 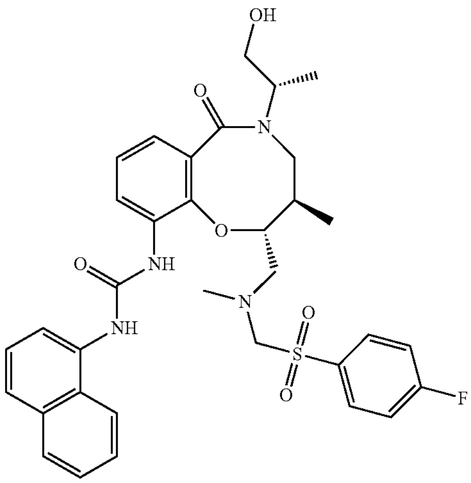 [SMILES: C[C@@H]1CN([C@@H](C)CO)C(=O)c2cccc(NC(=O)Nc3cccc4ccccc34)c2O[C@H]1CN(C)CS(=O)(=O)c1ccc(F)cc1] |
TABLE B-continued
| No. | Compound |
|---|---|
| 10A | 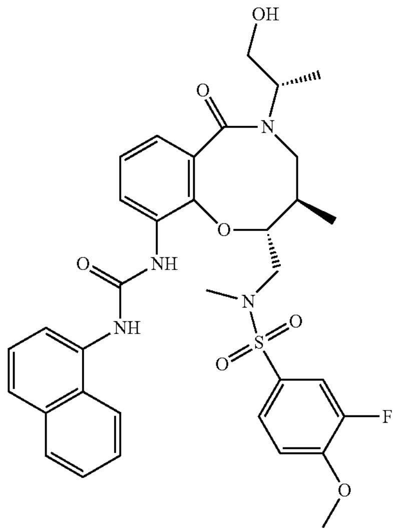 [SMILES: COc1ccc(S(=O)(=O)N(C)C[C@@H]2Oc3c(NC(=O)Nc4cccc5ccccc45)cccc3C(=O)N([C@@H](C)CO)C[C@H]2C)cc1F] |
| 11A | 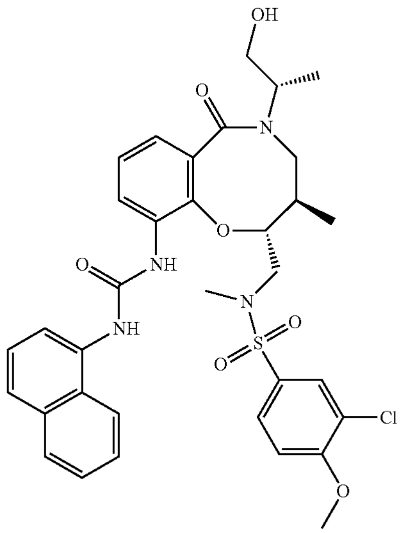 [SMILES: COc1ccc(S(=O)(=O)N(C)C[C@@H]2Oc3c(NC(=O)Nc4cccc5ccccc45)cccc3C(=O)N([C@@H](C)CO)C[C@H]2C)cc1Cl] |

TABLE B-continued
| No. | Compound |
|---|---|
| 12A | 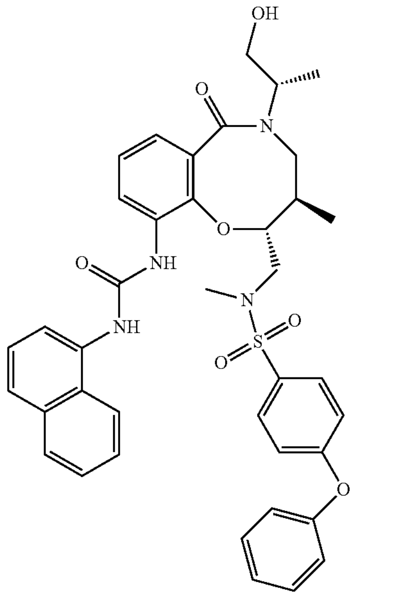 [SMILES: C[C@@H]1CN([C@@H](C)CO)C(=O)c2cccc(NC(=O)Nc3cccc4ccccc34)c2O[C@H]1CN(C)S(=O)(=O)c1ccc(Oc2ccccc2)cc1] |
| 13A | 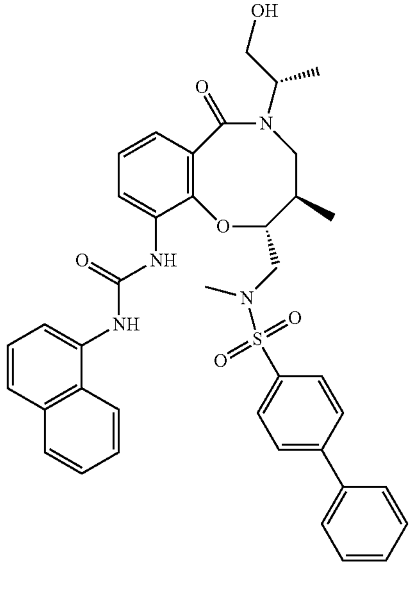 [SMILES: C[C@@H]1CN([C@@H](C)CO)C(=O)c2cccc(NC(=O)Nc3cccc4ccccc34)c2O[C@H]1CN(C)S(=O)(=O)c1ccc(-c2ccccc2)cc1] |
TABLE B-continued
| No. | Compound |
|---|---|
| 14A | 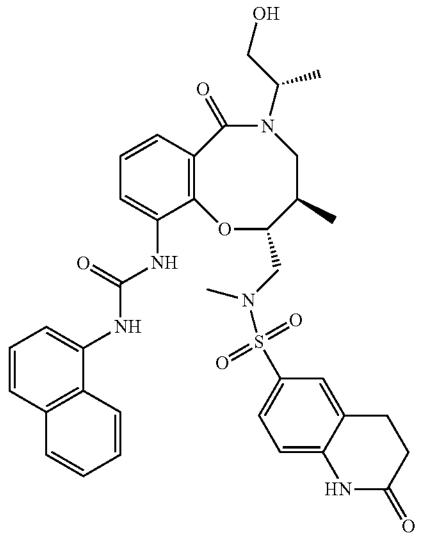 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)CCC(=O)N2] |
| 15A | 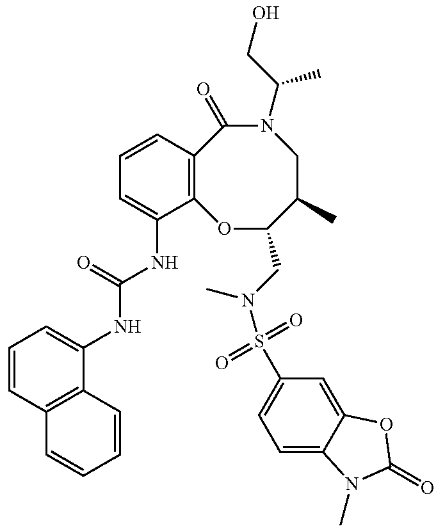 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)oc(=O)n2C] |
| 16A | 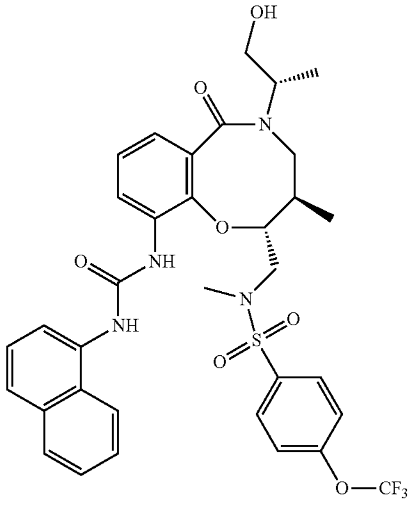 [SMILES: C[C@@H]1CN([C@@H](C)CO)C(=O)c2cccc(NC(=O)Nc3cccc4ccccc34)c2O[C@H]1CN(C)S(=O)(=O)c1ccc(OC(F)(F)F)cc1] |

TABLE B-continued
| No. | Compound |
| --- | --- |
| 17A | 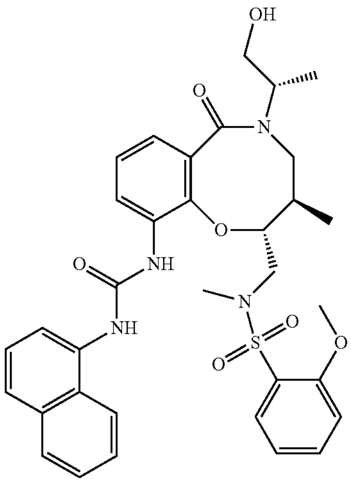 [SMILES: COc1ccccc1S(=O)(=O)N(C)C[C@@H]1Oc2c(NC(=O)Nc3cccc4ccccc34)cccc2C(=O)N([C@@H](C)CO)C[C@H]1C] |
| 18A | 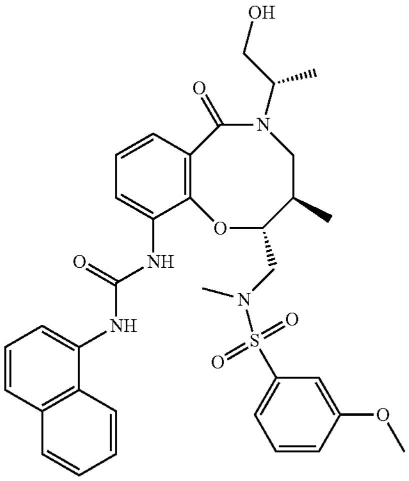 [SMILES: COc1cccc(S(=O)(=O)N(C)C[C@@H]2Oc3c(NC(=O)Nc4cccc5ccccc45)cccc3C(=O)N([C@@H](C)CO)C[C@H]2C)c1] |
| 19A | 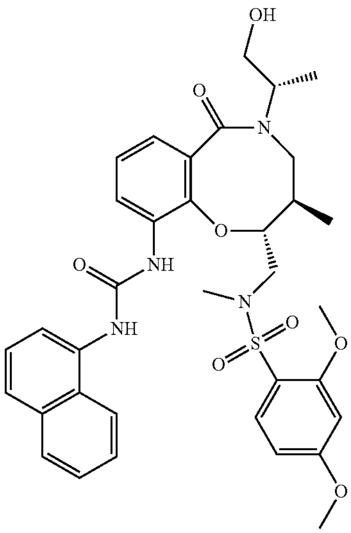 [SMILES: COc1ccc(S(=O)(=O)N(C)C[C@@H]2Oc3c(NC(=O)Nc4cccc5ccccc45)cccc3C(=O)N([C@@H](C)CO)C[C@H]2C)c(OC)c1] |
TABLE B-continued
| No. | Compound |
| --- | --- |
| 20A | 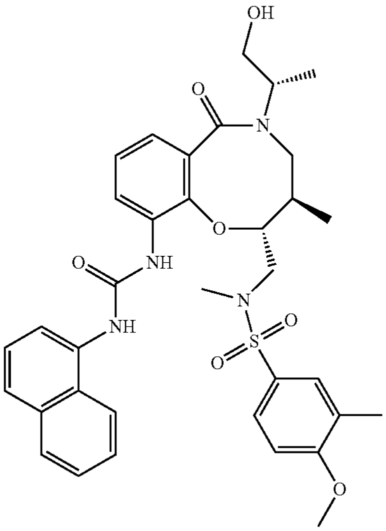 [SMILES: COc1ccc(S(=O)(=O)N(C)C[C@@H]2Oc3c(NC(=O)Nc4cccc5ccccc45)cccc3C(=O)N([C@@H](C)CO)C[C@H]2C)cc1C] |
| 21A | 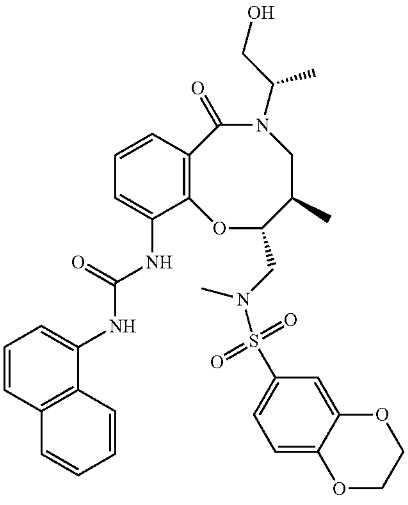 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)OCCO2] |
| 22A | 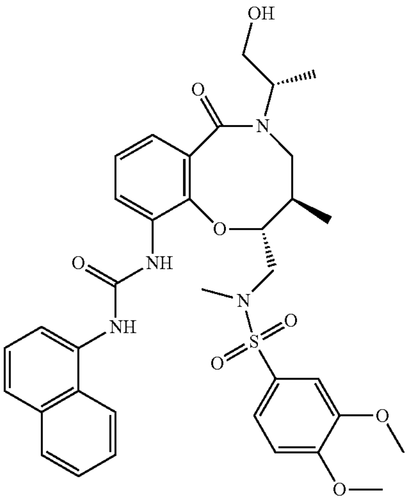 [SMILES: COc1ccc(S(=O)(=O)N(C)C[C@@H]2Oc3c(NC(=O)Nc4cccc5ccccc45)cccc3C(=O)N([C@@H](C)CO)C[C@H]2C)cc1OC] |

| No. | Compound |
|---|---|
| 23A | 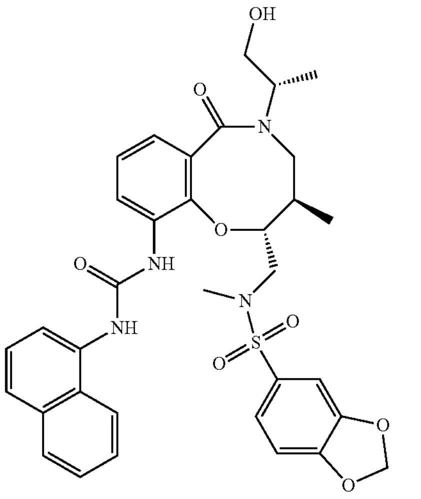 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)OCO2] |
| 24A | 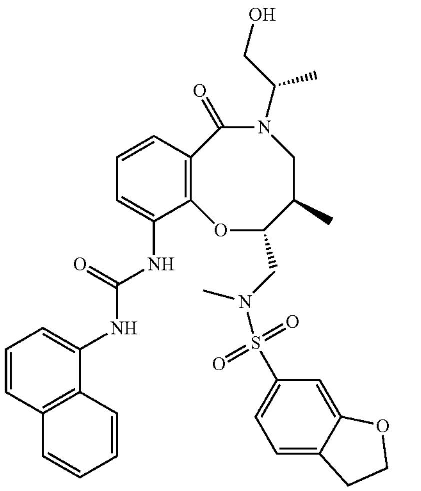 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)OCC2] |
| 25A | 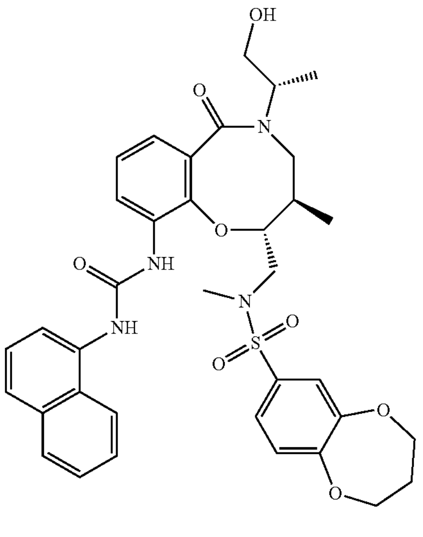 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(c1)OCCCO2] |
| No. | Compound |
|---|---|
| 26A | 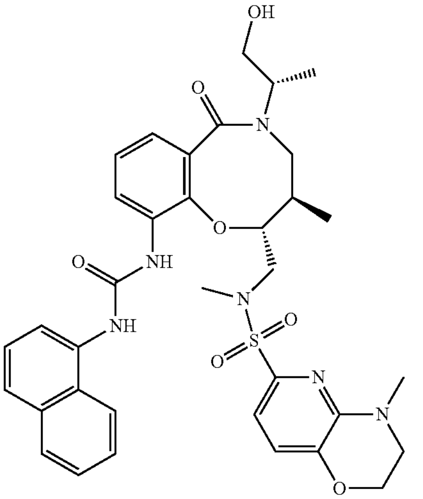 [SMILES: C[C@@H]1CN([C@@H](C)CO)C(=O)c2cccc(NC(=O)Nc3cccc4ccccc34)c2O[C@H]1CN(C)S(=O)(=O)c1ccc2c(n1)N(C)CCO2] |
| 27A | 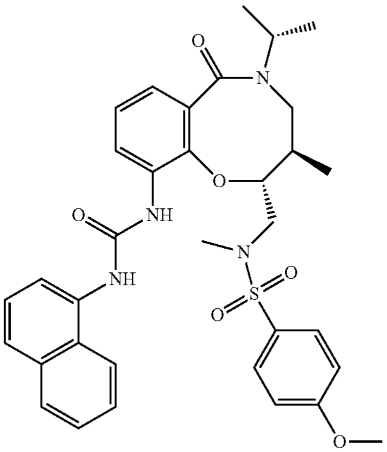 |
| 28A | 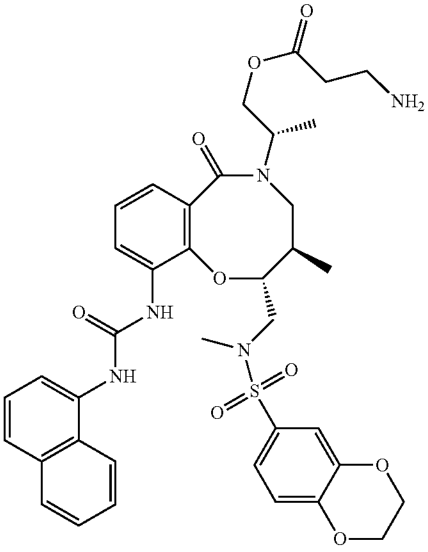 [SMILES: C[C@@H]1CN([C@@H](C)COC(=O)CCN)C(=O)c2cccc(NC(=O)Nc3cccc4ccccc34)c2O[C@H]1CN(C)S(=O)(=O)c1ccc2c(c1)OCCO2] |

TABLE B-continued
| No. | Compound |
|---|---|
| 29A | 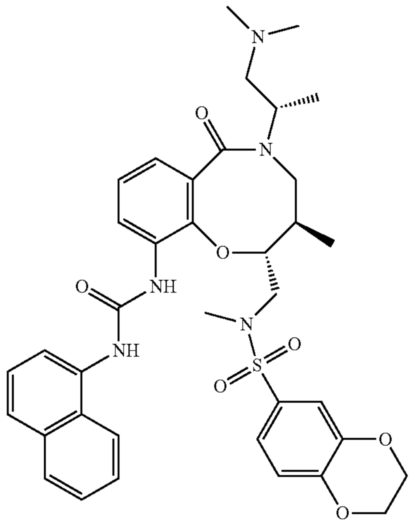 [SMILES: C[C@@H]1CN([C@@H](C)CN(C)C)C(=O)c2cccc(NC(=O)Nc3cccc4ccccc34)c2O[C@H]1CN(C)S(=O)(=O)c1ccc2c(c1)OCCO2] |
| 30A | 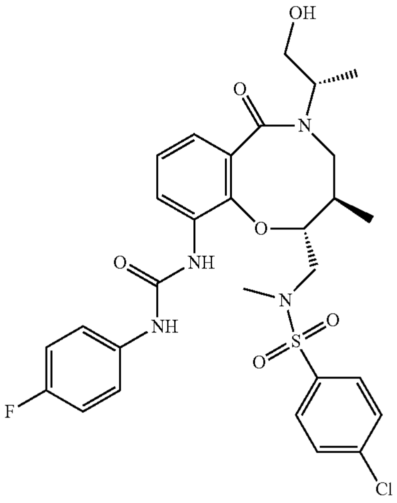 [SMILES: C[C@@H]1CN([C@@H](C)CO)C(=O)c2cccc(NC(=O)Nc3ccc(F)cc3)c2O[C@H]1CN(C)S(=O)(=O)c1ccc(Cl)cc1] |
| 31A | 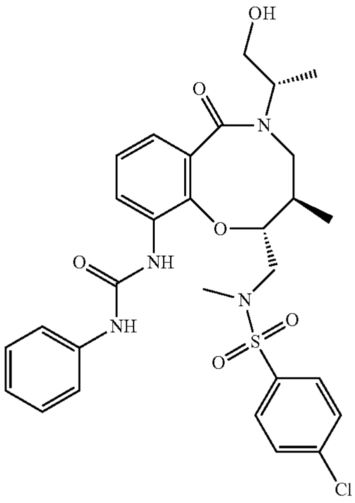 [SMILES: C[C@@H]1CN([C@@H](C)CO)C(=O)c2cccc(NC(=O)Nc3ccccc3)c2O[C@H]1CN(C)S(=O)(=O)c1ccc(Cl)cc1] |
TABLE B-continued
| No. | Compound |
|---|---|
| 31B | 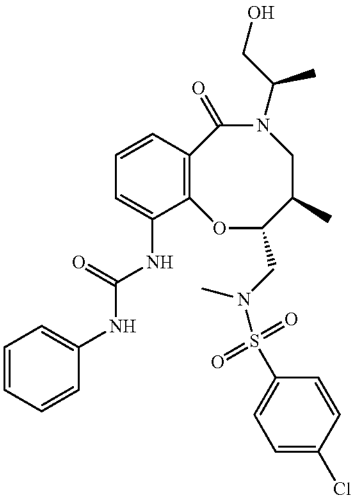 [SMILES: C[C@@H]1CN([C@H](C)CO)C(=O)c2cccc(NC(=O)Nc3ccccc3)c2O[C@H]1CN(C)S(=O)(=O)c1ccc(Cl)cc1] |
| 32A | 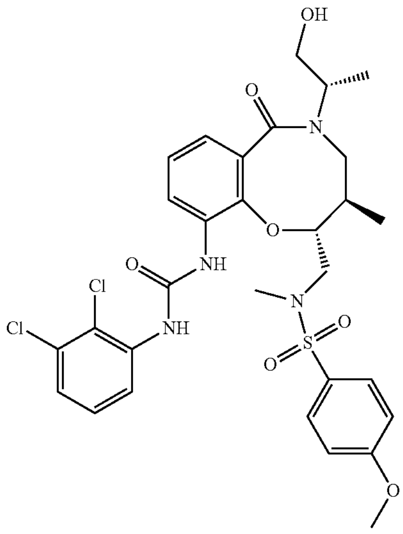 [SMILES: COc1ccc(S(=O)(=O)N(C)C[C@@H]2Oc3c(NC(=O)Nc4cccc(Cl)c4Cl)cccc3C(=O)N([C@@H](C)CO)C[C@H]2C)cc1] |
| 33A | 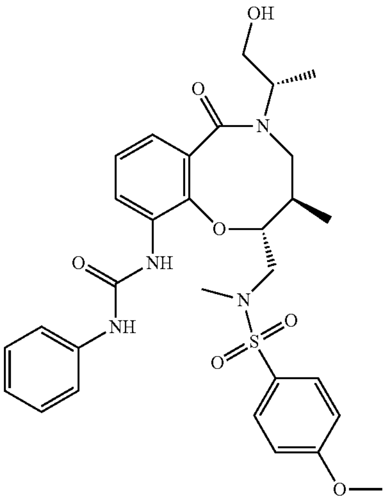 [SMILES: COc1ccc(S(=O)(=O)N(C)C[C@@H]2Oc3c(NC(=O)Nc4ccccc4)cccc3C(=O)N([C@@H](C)CO)C[C@H]2C)cc1] |

TABLE B-continued
| No. | Compound |
|---|---|
| 34A | 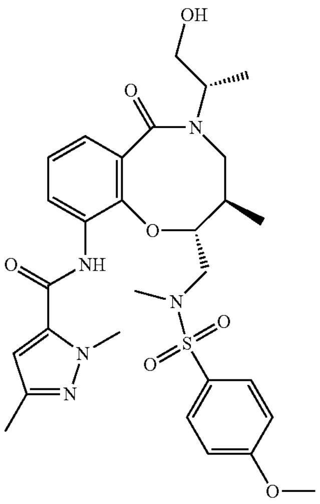 |
| 35A | 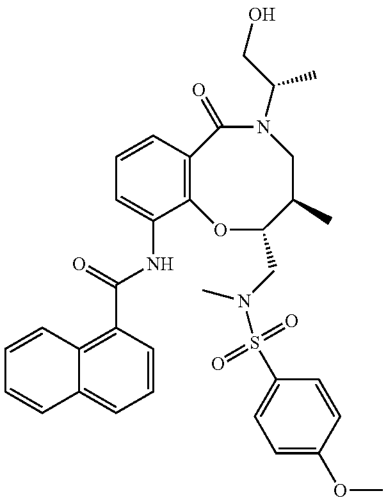 [SMILES: COc1ccc(S(=O)(=O)N(C)C[C@@H]2Oc3c(NC(=O)c4cccc5ccccc45)cccc3C(=O)N([C@@H](C)CO)C[C@H]2C)cc1] |
| 36A | 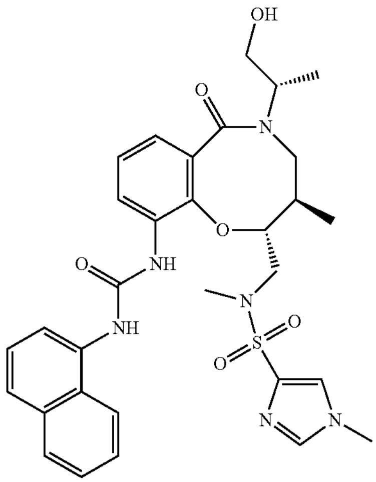 [SMILES: C[C@@H]1CN([C@@H](C)CO)C(=O)c2cccc(NC(=O)Nc3cccc4ccccc34)c2O[C@H]1CN(C)S(=O)(=O)c1cn(C)cn1] |
TABLE B-continued
| No. | Compound |
|---|---|
| 37A | 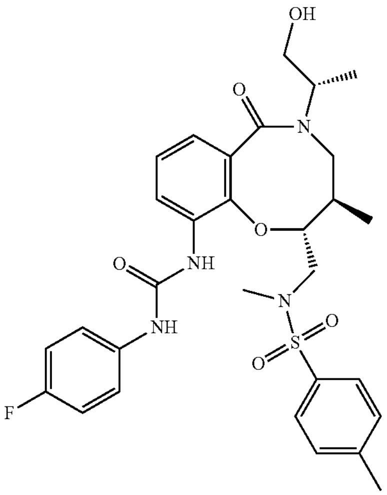 [SMILES: Cc1ccc(S(=O)(=O)N(C)C[C@@H]2Oc3c(NC(=O)Nc4ccc(F)cc4)cccc3C(=O)N([C@@H](C)CO)C[C@H]2C)cc1] |
| 37B | 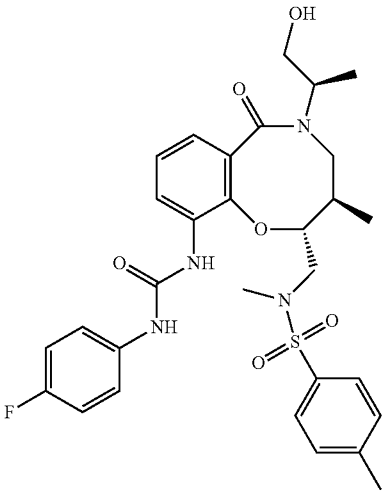 [SMILES: Cc1ccc(S(=O)(=O)N(C)C[C@@H]2Oc3c(NC(=O)Nc4ccc(F)cc4)cccc3C(=O)N([C@H](C)CO)C[C@H]2C)cc1] |
| 38A | 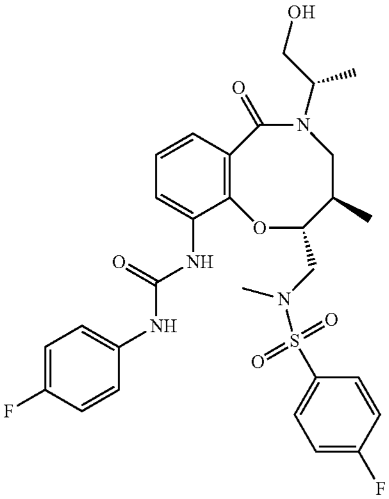 [SMILES: C[C@@H]1CN([C@@H](C)CO)C(=O)c2cccc(NC(=O)Nc3ccc(F)cc3)c2O[C@H]1CN(C)S(=O)(=O)c1ccc(F)cc1] |

TABLE B-continued
| No. | Compound |
| --- | --- |
| 39A | 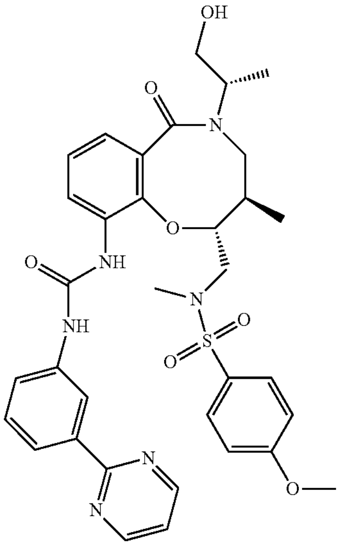 [SMILES: COc1ccc(S(=O)(=O)N(C)C[C@@H]2Oc3c(NC(=O)Nc4cccc(-c5ncccn5)c4)cccc3C(=O)N([C@@H](C)CO)C[C@H]2C)cc1] |
| 40A | 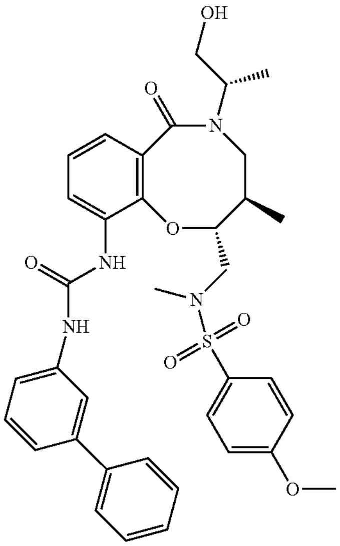 [SMILES: COc1ccc(S(=O)(=O)N(C)C[C@@H]2Oc3c(NC(=O)Nc4cccc(-c5ccccc5)c4)cccc3C(=O)N([C@@H](C)CO)C[C@H]2C)cc1] |
| 41A | 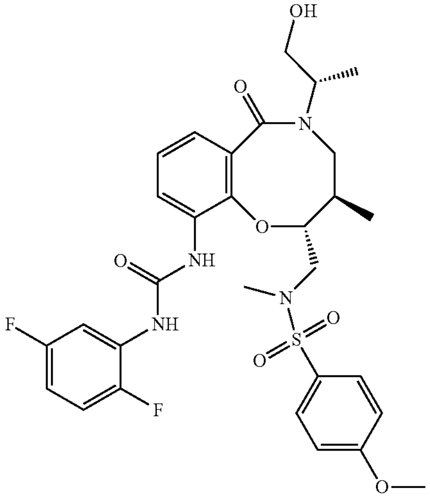 [SMILES: COc1ccc(S(=O)(=O)N(C)C[C@@H]2Oc3c(NC(=O)Nc4cc(F)ccc4F)cccc3C(=O)N([C@@H](C)CO)C[C@H]2C)cc1] |
TABLE B-continued
| No. | Compound |
| --- | --- |
| 42A | 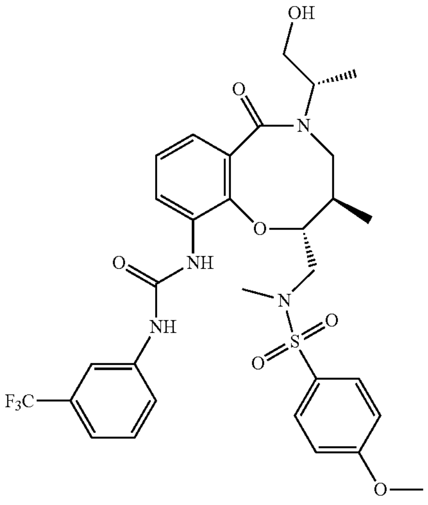 [SMILES: COc1ccc(S(=O)(=O)N(C)C[C@@H]2Oc3c(NC(=O)Nc4cccc(C(F)(F)F)c4)cccc3C(=O)N([C@@H](C)CO)C[C@H]2C)cc1] |
| 43A | 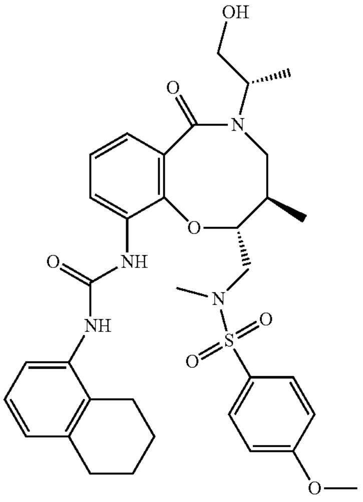 [SMILES: COc1ccc(S(=O)(=O)N(C)C[C@@H]2Oc3c(NC(=O)Nc4cccc5c4CCCC5)cccc3C(=O)N([C@@H](C)CO)C[C@H]2C)cc1] |
| 44A | 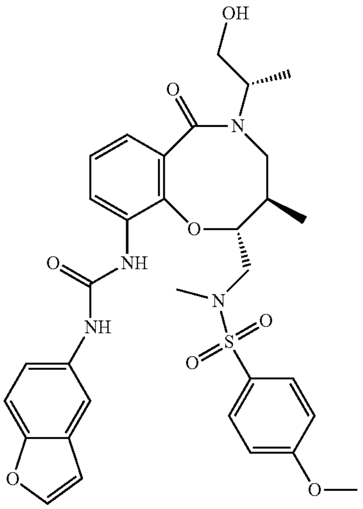 [SMILES: COc1ccc(S(=O)(=O)N(C)C[C@@H]2Oc3c(NC(=O)Nc4ccc5occc5c4)cccc3C(=O)N([C@@H](C)CO)C[C@H]2C)cc1] |

TABLE B-continued

| No. | Compound |
| --- | --- |
| 45A | 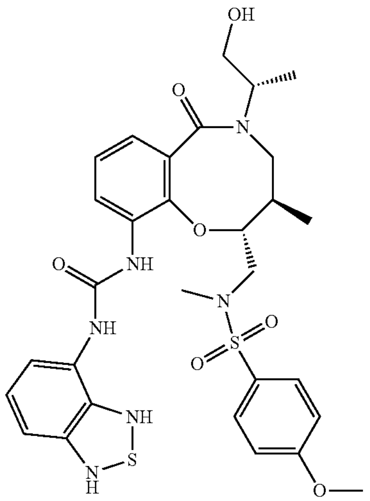 [SMILES: COc1ccc(S(=O)(=O)N(C)C[C@@H]2Oc3c(NC(=O)Nc4cccc5c4NSN5)cccc3C(=O)N([C@@H](C)CO)C[C@H]2C)cc1] |
| 46A | 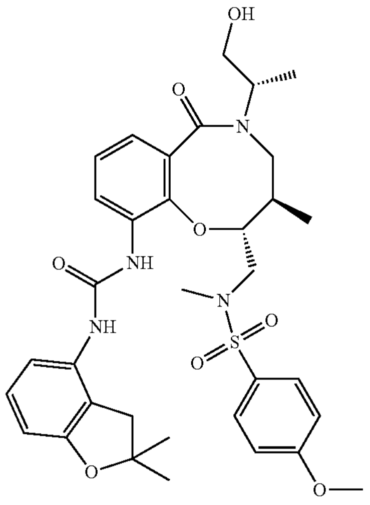 [SMILES: COc1ccc(S(=O)(=O)N(C)C[C@@H]2Oc3c(NC(=O)Nc4cccc5c4CC(C)(C)O5)cccc3C(=O)N([C@@H](C)CO)C[C@H]2C)cc1] |
| 47A | 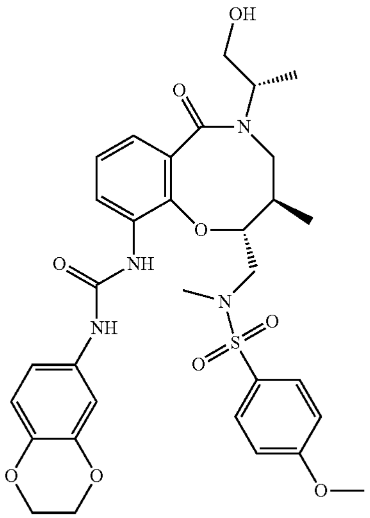 [SMILES: COc1ccc(S(=O)(=O)N(C)C[C@@H]2Oc3c(NC(=O)Nc4ccc5c(c4)OCCO5)cccc3C(=O)N([C@@H](C)CO)C[C@H]2C)cc1] |

TABLE B-continued

| No. | Compound |
| --- | --- |
| 48A | 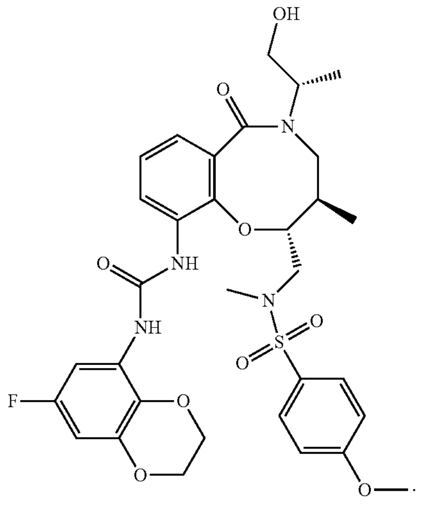 [SMILES: COc1ccc(S(=O)(=O)N(C)C[C@@H]2Oc3c(NC(=O)Nc4cc(F)cc5c4OCCO5)cccc3C(=O)N([C@@H](C)CO)C[C@H]2C)cc1] |

13. A method for the treatment of an autoimmune disease comprising the step of administering a compound of claim 1, to a patient in need thereof.

14. The method of claim 13, wherein said autoimmune disease is selected from multiple sclerosis, Crohn's disease, lupus erythematosus, rheumatoid arthritis, osteoarthritis, psoriasis, ulcerative colitis, type-1 diabetes, pancreatitis, asthma, idiopathic thrombocytopenia purpura, uveitis, Guillain-Barre syndrome or myasthenia gravis.

15. The method of claim 13, wherein said autoimmune disease is type-1 diabetes.

16. The method of claim 13, wherein said autoimmune disease is rheumatoid arthritis.

17. The method of claim 13, wherein said autoimmune disease is lupus.

18. A method of suppressing cytokine-induced beta-cell apoptosis comprising the step of administering a compound according to claim 1.

19. A method of preparing pancreatic islet cells for preservation or transplantation comprising the step of bringing a compound of claim 1, into contact with said pancreatic islet cells.

20. The method according to claim 19, wherein said pancreatic islet cells are Langerhans cells.

21. The method of improving glycemic control in a patient comprising the step of administering a compound of claim 1, to a patient in need thereof.

22. A method of treating a BCL-2 mediated disease or disorder by administering a compound according to claim 1, to a subject in need thereof.

23. The method according to claim 22, wherein said disease or disorder is a cell proliferative disorder.

24. The method according to claim 23, wherein said cell proliferative disorder is selected from the cell proliferative disorder is selected from breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

25. A method of treating a deubiquitinase mediated disease or disorder comprising administering to a subject in need thereof a compound according to claim 1.

26. A composition comprising a compound according to claim 1 and an inhibitor of a BCL-2 protein.

27. The composition according to claim 26, wherein said inhibitor of a BCL-2 protein is selected from ABT-263, ABT-737, gossypol, chelerythrine chloride, apogossypolone, antimycin A, TW-37, HA14-1, obatoclax (GX15-070), ApoG2, NMB and TM12-06.

28. The composition according to claim 27, wherein said inhibitor of BCL-2 protein is ABT-737.

29. A method of treating BCL-2 mediated disease or disorder by administering a composition according to claim 27 to a subject in need thereof.

30. The method according to claim 29, wherein said disease or disorder is a cell proliferative disorder.

31. The method according to claim 30, wherein said cell proliferative disorder is selected from the cell proliferative disorder is selected from breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

32. A method for treating a disease or disorder mediated by the abnormal or aberrant expression of one or more gene or gene product selected from

TABLE 1

| Accession No. | Description |
|---|---|
| 1370202_at | HRAS like suppressor 3, Hrasls3 |
| 1369268_at | activating transcription factor 3, Atf3 |

TABLE 1-continued

| Accession No. | Description |
|---|---|
| 1372013_at | interferon induced transmembrane protein 1 (predicted), Ifitm1_predicted |
| 1377156_at | similar to Transcription factor 7-like 2 (HMG box transcription factor 4) (T-cell-specific transcription factor 4) (TCF-4) (hTCF-4), LOC683733 |
| 1384391_at | retinol dehydrogenase 10 (all-trans), Rdh10 |
| 1373923_at | Retinol dehydrogenase 10 (all-trans), Rdh10 |
| 1368868_at | A kinase (PRKA) anchor protein (gravin) 12, Akap12 |
| 1393351_at | Retinol dehydrogenase 10 (all-trans), Rdh10 |
| 1367918_at | fasciculation and elongation protein zeta 1 (zygin I), Fez1 |
| 1368869_at | A kinase (PRKA) anchor protein (gravin) 12, Akap12 |
| 1388102_at | leukotriene B4 12-hydroxydehydrogenase, Ltb4dh |
| 1392547_at | hypothetical LOC302884, MGC105649 |
| 1396327_at | cytochrome P450, family 2, subfamily j, polypeptide 10 (predicted), Cyp2j10_predicted |
| 1368751_at | potassium voltage-gated channel, delayed-rectifier, subfamily S, member 3, Kcns3 |
| 1373309_at | transmembrane protein 86A (predicted), Tmem86a_predicted |
| 1368375_a_at | interleukin 15, Il15 |
| 1370427_at | platelet derived growth factor, alpha, Pdgfa |
| 1388502_at | inositol polyphosphate-5-phosphatase B, Inpp5b |
| 1372111_at | met proto-oncogene /// caveolin, caveolae protein 1 /// wingless-related MMTV integration site 2 /// ankyrin repeat, SAM and basic leucine zipper domain containing 1 /// cortactin binding protein 2 /// suppression of tumorigenicity 7 /// caveolin 2, Asz1 /// Cav1 /// Cav2 /// Cttnbp2 /// Met /// ST7 /// Wnt2 |
| 1374469_at | Transcribed locus, strongly similar to XP_578186.2 PREDICTED: similar to oxidation resistance 1 [*Rattus norvegicus*], — |
| 1378679_at | ubiquitin specific peptidase 25, Usp25 |
| 1379375_at | Platelet derived growth factor, alpha, Pdgfa |
| 1372302_at | family with sequence similarity 82, member C, Fam82c |
| 1372182_at | phosphofructokinase, platelet, Pfkp |
| 1386979_at | developmentally regulated protein TPO1, Tpo1 |
| 1390847_at | transmembrane protein 86A (predicted), Tmem86a_predicted |
| 1390226_at | similar to hypothetical protein LOC340061 (predicted), RGD1562552_predicted |
| 1374519_at | dedicator of cytokinesis 7, Dock7 |
| 1371033_at | transporter 1, ATP-binding cassette, sub-family B (MDR/TAP) /// transporter 2, ATP-binding cassette, sub-family B (MDR/TAP) /// proteosome (prosome, macropain) subunit, beta type 9 /// similar to butyrophilin-like 8 (predicted) /// RT1 class II, locus Da /// RT1 class II, locus Db1 /// major histocompatibility complex, class II, DM beta /// major histocompatibility complex, class II, DM alpha /// RT1 class II, locus Ba /// RT1 class II, locus Bb /// RT1 class II, locus DOb /// butyrophilin-like 4 /// butyrophilin-like 5 /// butyrophilin-like 3 /// Tesb pseudogene, Btnl3 /// Btnl4 /// Btnl5 /// Hla-dma /// Hla-dmb /// Psmb9 /// RGD1562488_predicted /// RT1-Ba /// RT1-Bb /// RT1-Da /// RT1-Db1 /// RT1-DOb /// Tap1 /// Tap2 /// Tesb |
| 1385502_at | Tripartite motif protein 21 (predicted), Trim21_predicted |
| 1371491_at | Notch gene homolog 1 (*Drosophila*), Notch1 |
| 1373911_at | periostin, osteoblast specific factor (predicted), Postn_predicted |
| 1393806_at | MANSC domain containing 1, Mansc1 |
| 1373912_at | Ectonucleotide pyrophosphatase/phosphodiesterase 4 (predicted), Enpp4_predicted |
| 1388936_at | cadherin 11, Cdh11 |
| 1374404_at | Jun oncogene, Jun |
| 1382074_at | ring finger protein 19B, Rnf19b |
| 1370974_at | vacuolar protein sorting 54 (yeast), Vps54 |
| 1368144_at | regulator of G-protein signaling 2, Rgs2 |
| 1369788_s_at | Jun oncogene, Jun |
| 1389528_s_at | Jun oncogene, Jun |
| 1369519_at | endothelin 1, Edn1 |
| 1395124_at | tryptophanyl-tRNA synthetase, Wars |
| 1376977_at | Prostaglandin E receptor 3 (subtype EP3), Ptger3 |
| 1373961_at | similar to 4930453N24Rik protein, MGC95208 |
| 1387398_at | protein kinase inhibitor, alpha, Pkia |
| 1389365_at | similar to CG3740-PA, LOC690000 |
| 1368856_at | Janus kinase 2, Jak2 |
| 1374499_at | CDNA clone MGC: 187619 IMAGE: 8367117, — |

TABLE 1-continued

| Accession No. | Description |
|---|---|
| 1377893_at | similar to CG3740-PA, LOC690000 |
| 1387074_at | regulator of G-protein signaling 2, Rgs2 |
| 1372602_at | starch binding domain 1, Stbd1 |
| 1395135_at | Williams Beuren syndrome chromosome region 27, Wbscr27 |
| 1398840_at | vesicle-associated membrane protein 5, Vamp5 |
| 1387800_at | Fas death domain-associated protein, Daxx |
| 1373761_at | similar to Protein FAM60A (Tera protein), LOC686611 |
| 1386998_at | aldolase C, Aldoc |
| 1384457_at | similar to Fbxw17 protein (predicted), RGD1566133_predicted |
| 1371071_at | guanine nucleotide binding protein, beta 4, Gnb4 |
| 1369319_at | ADP-ribosylation factor-like 6 interacting protein 5, Arl6ip5 |
| 1385210_at | dedicator of cytokinesis 5 (predicted), Dock5_predicted |
| 1388469_at | Insulin-like growth factor I mRNA, 3' end of mRNA, — |
| 1385961_at | Kruppel-like factor 5, Klf5 |
| 1394077_at | Rho family GTPase 3, Rnd3 |
| 1376026_at | downstream neighbor of SON, Donson |
| 1368111_at | ankyrin repeat and BTB (POZ) domain containing 2, Abtb2 |
| 1375870_a_at | RNA binding motif, single stranded interacting protein 1, Rbms1 |
| 1375739_at | EH-domain containing 4, Ehd4 |
| 1383915_at | hypothetical protein LOC686120, LOC686120 |
| 1390507_at | interferon stimulated exonuclease 20, Isg20 |
| 1373143_at | similar to hypothetical protein FLJ10652, RGD1309621 |
| 1379558_at | Similar to zinc finger protein 748 isoform 2, LOC680222 |
| 1380110_at | Janus kinase 2, Jak2 |
| 1389263_at | retinoic acid induced 14, Rai14 |
| 1373412_at | 5'-nucleotidase, cytosolic III (predicted), Nt5c3_predicted |
| 1387851_at | phosphotriesterase related, Pter |
| 1387035_a_at | Rho GTPase activating protein 17, Arhgap17 |
| 1377663_at | Rho family GTPase 3, Rnd3 |
| 1368321_at | early growth response 1, Egr1 |
| 1380513_at | RNA polymerase II associated protein 2, Rpap2 |
| 1390237_at | translocase of inner mitochondrial membrane 8 homolog a1 (yeast), Timm8a1 |
| 1368571_at | CAP-GLY domain containing linker protein 2, Clip2 |
| 1372056_at | CKLF-like MARVEL transmembrane domain containing 6, Cmtm6 |
| 1368982_at | protein kinase inhibitor, alpha, Pkia |
| 1388574_at | tryptophanyl-tRNA synthetase, Wars |
| 1373775_at | NEDD8 ultimate buster-1, Nub1 |
| 1383013_at | Kruppel-like factor 13, Klf13 |
| 1389732_at | Similar to CG4025-PA, LOC679937 |
| 1387294_at | SH3-domain binding protein 5 (BTK-associated), Sh3bp5 |
| 1385294_at | ets variant gene 6 (TEL oncogene), Etv6 |
| 1388027_a_at | reticulon 4, Rtn4 |
| 1370428_x_at | RT1 class Ib, locus Aw2 /// RT1 class Ia, locus A1 /// RT1 class Ia, locus A2 /// RT1 class Ib, locus Cl /// RT1 class II, locus DOa /// RT1 class II, locus Ha /// TAP binding protein /// discoidin domain receptor family, member 1 /// leucocyte specific transcript 1 /// Fas death domain-associated protein /// UDP-Gal:betaGlcNAc beta 1,3-galactosyltransferase, polypeptide 4 /// synaptic Ras GTPase activating protein 1 homolog (rat) /// general transcription factor II H, polypeptide 4 /// procollagen, type XI, alpha 2 /// RT1 class I, locus Ke4 /// RAB2, member RAS oncogene family-like /// PHD finger protein 1 /// zinc finger and BTB domain containing 9 /// POU domain, class 5, transcription factor 1 /// valyl-tRNA synthetase 2-like /// RT1 class I, CE12 /// RT1 class I, CE1 /// RT1 class I, CE5 /// RT1 class I, A3 /// WD repeat domain 46 /// MHC class II region expressed gene KE2 /// zinc finger protein 297 /// lymphotoxin B /// ATPase, H+ transporting, V1 subunit G isoform 2 /// RT1 class I, CE7 /// transcription factor 19 /// HCR (a-helix coiled-coil rod homolog) /// psoriasis susceptibility 1 candidate 2 (human) /// corneodesmosin /// RT1 class I, CE14 /// RT1 class I, CE2 /// RT1 class I, CE4 /// RT1 class I, CE15 /// RT1 class I, CE13 /// RT1 class I, CE11 /// RT1 class I, CE10 /// RT1 class I, CE3 /// RT1 class I, CE16 /// similar to corneodesmosin, Atp6v1g2 /// B3galt4 /// Cdsn /// Col11a2 /// Daxx /// Ddr1 /// Gtf2h4 /// Hcr /// Ke2 /// LOC682408 /// Lst1 /// Ltb /// Phf1 /// Pou5f1 /// Psors1c2 /// Rab2l /// RT1-A1 /// RT1-A2 /// RT1-A3 /// RT1-Aw2 /// RT1-CE1 /// RT1-CE10 /// RT1-CE11 /// RT1-CE12 /// RT1-CE13 /// RT1-CE14 /// RT1-CE15 /// RT1-CE16 /// RT1-CE2 /// RT1-CE3 /// RT1-CE4 /// RT1-CE5 /// RT1-CE7 /// RT1-C1 /// RT1-DOa /// RT1-Ha /// RT1-Ke4 /// Syngap1 /// Tapbp /// Tcf19 /// Vars2l /// Wdr46 /// Zbtb9 /// Zfp297 |
| 1393217_at | ATP-binding cassette, sub-family G (WHITE), member 3-like 1, Abcg3l1 |
| 1371049_at | dihydropyrimidinase-like 4, Dpysl4 |
| 1377387_a_at | Transcribed locus, strongly similar to NP_079738.2 endothelin converting enzyme 2 isoform c [*Mus musculus*], — |
| 1385658_at | zinc finger protein 313, Zfp313 |
| 1395297_at | similar to hypothetical protein FLJ10652, RGD1309621 |
| 1374387_at | ADP-ribosylation factor-like 6 interacting protein 5, Arl6ip5 |
| 1369633_at | chemokine (C—X—C motif) ligand 12, Cxcl12 |
| 1389014_at | pre-B-cell colony enhancing factor 1, Pbef1 |
| 1387257_at | secretin, Sct |
| 1387646_a_at | Max protein, Max |
| 1370463_x_at | RT1 class I, CE16, RT1-CE16 |
| 1381567_at | zinc finger with UFM1-specific peptidase domain, Zufsp |
| 1368181_at | methylenetetrahydrofolate dehydrogenase (NADP+ dependent), methenyltetrahydrofolate cyclohydrolase, formyltetrahydrofolate synthase, Mthfd1 |
| 1374678_at | sema domain, immunoglobulin domain (Ig), transmembrane domain (TM) and short cytoplasmic domain, (semaphorin) 4B, Sema4b |
| 1382158_at | zinc finger protein 202, Zfp202 |
| 1379450_at | CTTNBP2 N-terminal like (predicted), Cttnbp2nl_predicted |
| 1373831_at | hypothetical protein LOC619574, LOC619574 |
| 1377439_at | similar to hypothetical protein FLJ13231 (predicted) /// hypothetical protein LOC679830, LOC679830 /// RGD1310081_predicted |
| 1388583_at | chemokine (C-X-C motif) ligand 12, Cxcl12 |
| 1372473_at | tight junction protein 1 (predicted), Tjp1_predicted |
| 1376440_at | ring finger protein 139 (predicted), Rnf139_predicted |
| 1382873_at | CTTNBP2 N-terminal like (predicted), Cttnbp2nl_predicted |
| 1373830_at | hypothetical protein LOC619574, LOC619574 |
| 1396262_at | pre-B-cell colony enhancing factor 1, Pbef1 |
| 1372106_at | EH-domain containing 4, Ehd4 |
| 1376082_at | ecotropic viral integration site 1 (predicted), Evil_predicted |
| 1390036_at | solute carrier family 16 (monocarboxylic acid transporters), member 6, Slc16a6 |
| 1372270_at | dolichyl-phosphate (UDP-N-acetylglucosamine) N-acetylglucosaminephosphotransferase 1 (GlcNAc-1-P transferase), Dpagt1 |
| 1393234_at | Transcribed locus, strongly similar to NP_001106215.1 Rho guanine nucleotide exchange factor (GEF) 16 [*Mus musculus*], — |
| 1379287_at | cylindromatosis (turban tumor syndrome), Cyld |
| 1372695_at | Transcribed locus, strongly similar to NP_081678.1 fibronectin type III domain containing 5 [*Mus musculus*], — |
| 1382277_at | lymphocyte antigen 96, Ly96 |
| 1387265_at | diacylglycerol kinase, gamma, Dgkg |
| 1373669_at | glucosamine-6-phosphate deaminase 2 (predicted), Gnpda2_predicted |
| 1375216_at | poliovirus receptor-related 2, Pvrl2 |
| 1372846_at | cytochrome b, ascorbate dependent 3, Cybasc3 |
| 1379561_at | ATPase family, AAA domain containing 1, Atad1 |
| 1375177_at | Kruppel-like factor 13, Klf13 |
| 1395248_at | ER degradation enhancer, mannosidase alpha-like 1, Edem1 |
| 1383829_at | bobby sox homolog (*Drosophila*) (predicted), Bbx_predicted |
| 1372895_at | similar to RIKEN cDNA 5730469M10, RGD1309676 |
| 1380650_at | TRIO and F-actin binding protein, Triobp |
| 1393641_at | B-cell linker, Blnk |
| 1367758_at | alpha-fetoprotein, Afp |
| 1399167_a_at | growth factor receptor bound protein 2-associated protein 1 (predicted), Gab1_predicted |
| 1368274_at | drebrin-like, Dbnl |
| 1389059_at | Transcribed locus, weakly similar to XP_001250613.1 PREDICTED: hypothetical protein [*Bos taurus*], — |
| 1385411_at | ubiquitin specific protease 43, rCG_32844 |
| 1384186_at | ER degradation enhancer, mannosidase alpha-like 1, Edem1 |

TABLE 1-continued

| Accession No. | Description |
|---|---|
| 1371624_at | zinc finger CCCH-type containing 7B (predicted), Zc3h7b_predicted |
| 1375934_at | ring finger protein 128 /// hypothetical protein LOC680663, LOC680663 /// Rnf128 |
| 1389681_at | Transcribed locus, moderately similar to NP_002847.1 poliovirus receptor related 2 isoform alpha precursor [*Homo sapiens*], — |
| 1389164_at | hect domain and RLD 3 (predicted), Herc3_predicted |
| 1375582_at | zinc finger homeodomain 4 (predicted), Zfhx4_predicted |
| 1376766_at | formin-like 1 (predicted), Fmnl1_predicted |
| 1386346_at | transmembrane protein 19, Tmem19 |
| 1388195_at | CUG triplet repeat, RNA binding protein 2, Cugbp2 |
| 1383554_at | ring finger protein 128 /// hypothetical protein LOC680663, LOC680663 /// Rnf128 |
| 1391211_at | Atpase, class VI, type 11C (predicted), Atp11c_predicted |
| 1388071_x_at | RT1 class Ib, locus Aw2, RT1-Aw2 |
| 1383662_at | hypothetical protein LOC500956, LOC500956 |
| 1388791_at | similar to 2810022L02Rik protein, RGD1309930 |
| 1387180_at | interleukin 1 receptor, type II, Il1r2 |
| 1373136_at | zinc finger with UFM1-specific peptidase domain, Zufsp |
| 1373913_at | polyribonucleotide nucleotidyltransferase 1, Pnpt1 |
| 1369562_at | hippocalcin-like 1, Hpcal1 |
| 1371662_at | lysyl-tRNA synthetase, Kars |
| 1392658_at | Similar to transcription elongation factor A 1 isoform 2, LOC498453 |
| 1370972_x_at | RT1 class I, CE5, RT1-CE5 |
| 1388409_at | zinc finger CCCH-type containing 7B (predicted), Zc3h7b_predicted |
| 1372090_at | Max protein, Max |
| 1392958_at | cylindromatosis (turban tumor syndrome), Cyld |
| 1369557_at | caspase 7, Casp7 |
| 1376117_at | solute carrier family 44, member 4, Slc44a4 |
| 1372533_at | ER degradation enhancer, mannosidase alpha-like 1, Edem1 |
| 1394842_at | transmembrane protein 19, Tmem19 |
| 1399153_at | RABSB, member RAS oncogene family (predicted), Rab5b_predicted |
| 1369197_at | apoptotic peptidase activating factor 1, Apaf1 |
| 1391679_at | hypothetical protein LOC691083, LOC691083 |
| 1375955_at | zinc finger protein 313, Zfp313 |
| 1383551_at | 2,3-bisphosphoglycerate mutase, Bpgm |
| 1373501_at | NIMA (never in mitosis gene a)-related expressed kinase 7, Nek7 |
| 1398983_at | mitochondrial ribosomal protein L30 (predicted), Mrpl30_predicted |
| 1389387_at | similar to Proteasome inhibitor PI31 subunit, LOC682071 /// LOC689852 |
| 1373065_at | protein tyrosine phosphatase, non-receptor type 18, Ptpn18 |
| 1377000_at | WAS protein homology region 2 domain containing 1, Whdc1 |
| 1379256_at | similar to RIKEN cDNA 1810030O07 (predicted), RGD1565685_predicted |
| 1374400_at | EFR3 homolog A (*S. cerevisiae*), Efr3a |
| 1373520_at | CDNA clone IMAGE: 7367270, — |
| 1372865_at | zinc finger protein 364 (predicted), Zfp364_predicted |
| 1392978_at | solute carrier family 25, member 28, Slc25a28 |
| 1372211_at | v-maf musculoaponeurotic fibrosarcoma oncogene family, protein K (avian), Mafk |
| 1379957_at | schlafen 8, Slfn8 |
| 1371774_at | spermidine/spermine N1-acetyl transferase 1, Sat1 |
| 1369067_at | nuclear receptor subfamily 4, group A, member 3, Nr4a3 |
| 1387131_at | serine (or cysteine) peptidase inhibitor, clade I, member 1, Serpini1 |
| 1375853_at | Similar to CG13957-PA (predicted), RGD1309995_predicted |
| 1377970_at | poly (ADP-ribose) polymerase family, member 8, Parp8 |
| 1388823_at | RAB5B, member RAS oncogene family (predicted), Rab5b_predicted |
| 1389053_at | Similar to hypothetical protein FLJ20627 (predicted), RGD1309546_predicted |
| 1371525_at | solute carrier family 12, member 7, Slc12a7 |
| 1367710_at | proteasome (prosome, macropain) 28 subunit, beta, Psme2 |
| 1391442_at | EH-domain containing 3, Ehd3 |
| 1392838_at | similar to CG13957-PA (predicted), RGD1309995_predicted |
| 1387897_at | 2',3'-cyclic nucleotide 3' phosphodiesterase, Cnp |
| 1376835_at | Solute carrier family 35, member B2, Slc35b2 |

TABLE 1-continued

| Accession No. | Description |
|---|---|
| 1380121_at | NIMA (never in mitosis gene a)-related expressed kinase 7, Nek7 |
| 1388768_at | small G protein signaling modulator 2, Sgsm2 |
| 1368476_at | nuclear receptor subfamily 3, group C, member 2, Nr3c2 |
| 1367746_a_at | flotillin 2, Flot2 |
| 1370946_at | nuclear factor I/X, Nfix |
| 1393389_at | nuclear receptor subfamily 4, group A, member 3, Nr4a3 |
| 1368273_at | mitogen-activated protein kinase 6, Mapk6 |
| 1388544_at | 2,3-bisphosphoglycerate mutase, Bpgm |
| 1375447_at | GTP binding protein 1 (predicted), Gtpbp1_predicted |
| 1399063_at | ZUBR1, Rbaf600 |
| 1388233_at | cytokine inducible SH2-containing protein, Cish |
| 1367663_at | proteasome (prosome, macropain) 28 subunit, alpha, Psme1 |
| 1380001_at | pinin, Pnn |
| 1390859_at | Nedd4 binding protein 1, N4bp1 |
| 1374939_at | cytoplasmic FMR1 interacting protein 2 (predicted), Cyfip2_predicted |
| 1395336_at | Similar to 2810022L02Rik protein, RGD1309930 |
| 1383768_at | ELAV (embryonic lethal, abnormal vision, *Drosophila*)-like 2 (Hu antigen B), Elavl2 |
| 1368813_at | CCAAT/enhancer binding protein (C/EBP), delta, Cebpd |
| 1376810_at | M-phase phosphoprotein 8 /// poly (ADP-ribose) polymerase family, member 4, Mphosph8 /// Parp4 |
| 1369559_a_at | CD47 antigen (Rh-related antigen, integrin-associated signal transducer), Cd47 |
| 1386922_at | carbonic anhydrase 2, Ca2 |
| 1383616_at | interleukin 10 receptor, beta, Il10rb |
| 1368248_at | CDP-diacylglycerol synthase 1, Cds1 |
| 1368158_at | sec1 family domain containing 1, Scfd1 |
| 1369654_at | protein kinase, AMP-activated, alpha 2 catalytic subunit, Prkaa2 |
| 1392077_at | putative C11orf8 homolog (human), C11orf8h |
| 1376692_at | homeodomain interacting protein kinase 2 (predicted), Hipk2_predicted |
| 1372179_at | hippocalcin-like 1, Hpcal1 |
| 1369590_a_at | DNA-damage inducible transcript 3, Ddit3 |
| 1372101_at | phosphatidic acid phosphatase type 2B, Ppap2b |
| 1380867_a_at | pleckstrin homology domain containing, family M (with RUN domain) member 1, Plekhm1 |
| 1371509_at | transforming growth factor beta regulated gene 1, Tbrg1 |
| 1375677_at | transducer of ERBB2, 2, Tob2 |
| 1391222_at | Nedd4 binding protein 1, N4bp1 |
| 1383369_at | tripartite motif-containing 26, Trim26 |
| 1367986_at | prostaglandin F2 receptor negative regulator, Ptgfrn |
| 1393359_at | adaptor-related protein complex 3, beta 2 subunit (predicted), Ap3b2_predicted |
| 1371925_at | ATPase type 13A1 (predicted), Atp13a1_predicted |
| 1373091_at | pleiomorphic adenoma gene-like 2 (predicted), Plagl2_predicted |
| 1368503_at | GTP cyclohydrolase 1, Gch1 |
| 1367733_at | carbonic anhydrase 2, Ca2 |
| 1384244_at | hydroxysteroid dehydrogenase like 2, Hsdl2 |
| 1389282_at | Integrin alpha 3 (predicted), Itga3_predicted |
| 1380964_at | dystrobrevin alpha (predicted), Dtna_predicted |
| 1393253_at | zinc finger protein 365, Zfp365 |
| 1388798_at | ubiquitin-conjugating enzyme E2E 2 (UBC4/5 homolog, yeast), Ube2e2 |
| 1392107_at | strawberry notch homolog 2 (*Drosophila*), Sbno2 |
| 1386976_at | CD82 antigen, Cd82 |
| 1376737_at | hypothetical protein LOC690243, LOC690243 |
| 1372009_at | tyrosyl-tRNA synthetase, Yars |
| 1399161_a_at | type 1 tumor necrosis factor receptor shedding aminopeptidase regulator, Arts1 |
| 1380582_at | colony stimulating factor 1 (macrophage), Csf1 |
| 1378293_at | tripartite motif-containing 26, Trim26 |
| 1395426_at | ubiquitin-conjugating enzyme E2 variant 1 (predicted), Ube2v1_predicted |
| 1377759_at | BH3 interacting domain death agonist, Bid |
| 1383679_at | ring finger protein 31 (predicted), Rnf31_predicted |
| 1368716_at | protein phosphatase 1, regulatory (inhibitor) subunit 14c, Ppp1r14c |
| 1392518_at | Similar to Protein C22orf5, RGD1306591 |
| 1386926_at | acyl-CoA synthetase long-chain family member 5, Acsl5 |
| 1375006_at | CDNA clone IMAGE: 7318427, — |
| 1389913_at | leucine rich repeat (in FLII) interacting protein 1, Lrrfip1 |
| 1373588_at | FERM domain containing 8, Frmd8 |
| 1382710_at | Ectodermal-neural cortex 1, Enc1 |

TABLE 1-continued

| Accession No. | Description |
|---|---|
| 1371550_at | TSC22 domain family, member 4, Tsc22d4 |
| 1368679_a_at | Yamaguchi sarcoma viral (v-yes-1) oncogene homolog, Lyn |
| 1389331_at | CDNA clone IMAGE: 7313169, — |
| 1381570_at | T-cell activation NFKB-like protein, Ta-nfkbh |
| 1367696_at | interferon induced transmembrane protein 2, Ifitm2 |
| 1396278_at | sorting nexin 11, Snx11 |
| 1393703_at | human immunodeficiency virus type I enhancer binding protein 3 (predicted), Hivep3_predicted |
| 1379460_at | SH3-domain GRB2-like (endophilin) interacting protein 1, Sgip1 |
| 1371005_at | ATP-binding cassette, sub-family C (CFTR/MRP), member 1, Abcc1 |
| 1368928_at | tripartite motif-containing 3, Trim3 |
| 1371531_at | similar to mammalian retrotransposon derived 8b, LOC678880 |
| 1368674_at | liver glycogen phosphorylase, Pygl |
| 1368896_at | MAD homolog 7 (*Drosophila*), Smad7 |
| 1387221_at | GTP cyclohydrolase 1, Gch1 |
| 1385361_at | ATPase, class V, type 10A, Atp10a |
| 1376174_at | serine (or cysteine) peptidase inhibitor, clade A (alpha-1 antiproteinase, antitrypsin), member 11, Serpina11 |
| 1390423_at | MYC binding protein 2, Mycbp2 |
| 1372869_at | similar to isopentenyl diphosphate delta-isomerase type 2 (predicted) /// similar to Nucleolar GTP-binding protein 1 (Chronic renal failure gene protein) (GTP-binding protein NGB), LOC689842 /// RGD1560805_predicted |
| 1391897_at | RAB GTPase activating protein 1-like, Rabgap1l |
| 1371825_at | small nuclear RNA activating complex, polypeptide 2, Snapc2 |
| 1382775_at | ryanodine receptor 2, cardiac, Ryr2 |
| 1385758_at | SAPS domain family, member 1 (predicted), Saps1_predicted |
| 1382029_at | similar to CDNA sequence BC017647 (predicted), RGD1566149_predicted |
| 1371528_at | FK506 binding protein 8, Fkbp8 |
| 1367938_at | UDP-glucose dehydrogenase, Ugdh |
| 1371659_at | ras homolog gene family, member C (predicted), Rhoc_predicted |
| 1371731_at | Similar to Coatomer gamma-2 subunit (Gamma-2 coat protein) (Gamma-2 COP) (predicted), RGD1566215_predicted |
| 1373748_at | PDZ domain containing RING finger 3 (predicted), Pdzrn3_predicted |
| 1374035_at | rad and gem related GTP binding protein 2, Rem2 |
| 1368983_at | heparin-binding EGF-like growth factor, Hbegf |
| 1375861_at | nucleosome assembly protein 1-like 5, Nap1l5 |
| 1394022_at | inhibitor of DNA binding 4, Id4 |
| 1370606_at | purinergic receptor P2Y, G-protein coupled 1, P2ry1 |
| 1368641_at | wingless-related MMTV integration site 4, Wnt4 |
| 1382351_at | GTP binding protein (gene overexpressed in skeletal muscle) (predicted), Gem_predicted |
| 1368998_at | NK6 transcription factor related, locus 1 (*Drosophila*), Nkx6-1 |
| 1375120_at | inhibitor of DNA binding 4, Id4 |
| 1384262_at | protein phosphatase 1, regulatory (inhibitor) subunit 3B, Ppp1r3b |
| 1384448_at | similar to RIKEN cDNA 1700045I19 (predicted), RGD1565844_predicted |
| 1371091_at | insulin receptor substrate 2, Irs2 |
| 1378899_at | solute carrier family 35, member D3 (predicted), Slc35d3_predicted |
| 1392590_at | Rho GTPase activating protein 24, Arhgap24 |
| 1376901_a_at | Similar to Hypothetical protein 6330514E13 (predicted), RGD1559693_predicted |
| 1367948_a_at | kinase insert domain protein receptor, Kdr |
| 1378925_at | cAMP responsive element modulator, Crem |
| 1379419_at | transmembrane protein 34, Tmem34 |
| 1372308_at | CDNA clone IMAGE: 7366335, — |
| 1379724_at | pleckstrin homology-like domain, family B, member 2, Phldb2 |
| 1390403_at | family with sequence similarity 43, member A, Fam43a |
| 1393550_at | cAMP responsive element modulator, Crem |
| 1382312_at | AT rich interactive domain 5B (Mrf1 like) (predicted), Arid5b_predicted |
| 1367977_at | synuclein, alpha, Snca |
| 1388108_at | ELOVL family member 6, elongation of long chain fatty acids (yeast), Elovl6 |
| 1390148_a_at | zinc finger protein 395 (predicted), Zfp395_predicted |
| 1369737_at | cAMP responsive element modulator, Crem |
| 1370478_at | myosin XVI, Myo16 |
| 1390127_at | DIX domain containing 1, Dixdc1 |
| 1392183_at | homeobox C9, Hoxc9 |
| 1373786_at | zinc finger protein 703, Zfp703 |
| 1369770_at | somatostatin receptor 1, Sstr1 |
| 1370942_at | RAS p21 protein activator 3, Rasa3 |
| 1397587_at | Histone deacetylase 5, Hdac5 |
| 1387455_a_at | very low density lipoprotein receptor, Vldlr |
| 1376265_at | six transmembrane epithelial antigen of the prostate 2, Steap2 |
| 1387947_at | v-maf musculoaponeurotic fibrosarcoma oncogene family, protein B (avian), Mafb |
| 1385374_at | Transcribed locus, strongly similar to NP_062067.2 thyrotroph embryonic factor [*Rattus norvegicus*], — |
| 1397729_x_at | similar to RIKEN cDNA 1600029D21, LOC363060 |
| 1381605_at | ubiquitin specific protease 13 (isopeptidase T-3) (predicted), Usp13_predicted |
| 1369564_at | rad and gem related GTP binding protein 2, Rem2 |
| 1387477_at | potassium channel, subfamily K, member 12, Kcnk12 |
| 1395223_at | kelch domain containing 8B, Klhdc8b |
| 1372548_at | Transcribed locus, strongly similar to NP_066940.1 cryptochrome 2 (photolyase-like) [*Homo sapiens*], — |
| 1385387_at | NK2 transcription factor related, locus 2 (*Drosophila*) (predicted), Nkx2-2_predicted |
| 1385491_at | PNMA-like 2, Pnmal2 |
| 1367805_at | glutaminase, Gls |
| 1374594_at | similar to RIKEN cDNA 1600029D21, LOC363060 |
| 1373179_at | similar to H43E16.1, LOC689994 |
| 1370474_at | thyroid hormone receptor beta, Thrb |
| 1367627_at | glycine amidinotransferase (L-arginine:glycine amidinotransferase), Gatm |
| 1383721_at | frizzled homolog 8 (*Drosophila*), Fzd8 |
| 1375043_at | FBJ osteosarcoma oncogene, Fos |
| 1389611_at | very low density lipoprotein receptor, Vldlr |
| 1393691_at | hypothetical protein LOC688273, LOC688273 |
| 1377404_at | stanniocalcin 1, Stc1 |
| 1379863_at | potassium voltage gated channel, Shal-related family, member 2, Kcnd2 |
| 1368782_at | somatostatin receptor 2, Sstr2 |
| 1391117_at | PNMA-like 2, Pnmal2 |
| 1387968_at | solute carrier family 6 (neurotransmitter transporter), member 15, Slc6a15 |
| 1392663_at | similar to hypothetical protein FLJ13188 (predicted), RGD1305500_predicted |
| 1370058_at | neurofilament, light polypeptide, Nefl |
| 1388395_at | G0/G1 switch gene 2, G0s2 |
| 1377940_at | family with sequence similarity 101, member B, Fam101b |
| 1369098_at | very low density lipoprotein receptor, Vldlr |
| 1387370_at | tropomodulin 1, Tmod1 |
| 1385663_at | ubiquitin specific protease 13 (isopeptidase T-3) (predicted), Usp13_predicted |
| 1370111_at | potassium intermediate/small conductance calcium-activated channel, subfamily N, member 2, Kcnn2 |
| 1382924_at | pantothenate kinase 1 (predicted), Pank1_predicted |
| 1367857_at | fatty acid desaturase 1, Fads1 |
| 1381190_at | LIM domain only protein 7, LMO7 |
| 1373336_at | G protein-coupled receptor, family C, group 5, member B (predicted), Gprc5b_predicted |
| 1369752_a_at | calcium/calmodulin-dependent protein kinase IV, Camk4 |
| 1390339_at | Ubiquitin specific protease 13 (isopeptidase T-3) (predicted), Usp13_predicted |
| 1383390_at | family with sequence similarity 123A, Fam123a |
| 1383826_at | Rab40b, member RAS oncogene family (predicted), Rab40b_predicted |
| 1379374_at | plasticity related gene 1, Lppr4 |
| 1385555_at | family with sequence similarity 101, member A, Fam101a |
| 1398431_at | carbonic anhydrase 8, Car8 |
| 1387212_at | basic helix-loop-helix domain containing, class B, 8, Bhlhb8 |
| 1389911_at | meteorin, glial cell differentiation regulator-like, Metrnl |
| 1393615_at | similar to DEP domain containing 6 (predicted), RGD1561030_predicted |
| 1398732_at | hypothetical protein LOC688273, LOC688273 |
| 1387599_a_at | NAD(P)H dehydrogenase, quinone 1, Nqo1 |
| 1374906_at | ring finger protein 113A1, Rnf113a1 |

TABLE 1-continued

| Accession No. | Description |
| --- | --- |
| 1374354_at | PHD finger protein 19 (predicted), Phf19_predicted |
| 1372754_at | adaptor protein, phosphotyrosine interaction, PH domain and leucine zipper containing 2, Appl2 |
| 1384415_at | SRY-box containing gene 7 (predicted), Sox7_predicted |
| 1379626_at | Special AT-rich sequence binding protein 1, Satb1 |
| 1373985_at | Similar to KIAA1183 protein (predicted), RGD1560435_predicted |
| 1373108_at | protein phosphatase 1, regulatory (inhibitor) subunit 3C, Ppp1r3c |
| 1375726_at | LIM domain only 7, Lmo7 |
| 1384869_at | abhydrolase domain containing 7 (predicted), Abhd7_predicted |
| 1390097_at | TSPY-like 4, Tspyl4 |
| 1369792_at | G protein-coupled receptor 6, Gpr6 |
| 1369753_at | calcium/calmodulin-dependent protein kinase IV, Camk4 |
| 1390443_at | similar to DNA segment, Chr 16, ERATO Doi 472, expressed (predicted), RGD1563888_predicted |
| 1369095_at | protein phosphatase 1, regulatory (inhibitor) subunit 9A, Ppp1r9a |
| 1376649_at | SNF1-like kinase 2 (predicted), Snf1lk2_predicted |
| 1376687_at | ubiquitin specific peptdiase 1, Usp1 |
| 1369738_s_at | cAMP responsive element modulator, Crem |
| 1389514_at | leucine rich repeat and Ig domain containing 1, Lingo1 |
| 1380305_at | NOD3-like protein, nod3l |
| 1387349_at | short stature homeobox 2, Shox2 |
| 1370317_at | asparagine-linked glycosylation 10 homolog B (yeast, alpha-1,2-glucosyltransferase), Alg10b |
| 1388078_a_at | amiloride-sensitive cation channel 2, neuronal, Accn2 |
| 1393952_at | coiled-coil domain containing 68, Ccdc68 |
| 1391601_at | leucine rich repeat protein 2, neuronal (predicted), Lrrn2_predicted |
| 1385036_at | synuclein, alpha interacting protein (synphilin) (predicted), Sncaip_predicted |
| 1383573_at | teashirt zinc finger family member 1, Tshz1 |
| 1376958_at | Similar to serine (or cysteine) proteinase inhibitor, clade B, member 9 (predicted), RGD1562844_predicted |
| 1372447_at | Fibroblast growth factor receptor 1, Fgfr1 |
| 1385636_at | frizzled homolog 3 (*Drosophila*), Fzd3 |
| 1370122_at | RAB27B, member RAS oncogene family, Rab27b |
| 1371045_at | amiloride-sensitive cation channel 2, neuronal, Accn2 |
| 1377506_at | LAG1 homolog, ceramide synthase 1 /// growth differentiation factor 1 (predicted), Gdf1_predicted /// Lass1 |
| 1379292_at | Similar to 5730420B22Rik protein (predicted), RGD1306755_predicted |
| 1372457_at | mitochondrial tumor suppressor 1, Mtus1 |
| 1374706_at | Growth differentiation factor 11, Gdf11 |
| 1379703_at | DENN/MADD domain containing 3, Dennd3 |
| 1383483_at | RAB9B, member RAS oncogene family (predicted), Rab9b_predicted |
| 1382868_at | sema domain, transmembrane domain (TM), and cytoplasmic domain, (semaphorin) 6A (predicted), Sema6a_predicted |
| 1368825_at | short stature homeobox 2, Shox2 |
| 1369954_at | isocitrate dehydrogenase 1 (NADP+), soluble, Idh1 |
| 1388718_at | tropomodulin 1, Tmod1 |
| 1370218_at | lactate dehydrogenase B, Ldhb |
| 1393307_at | Phosphatase and actin regulator 3, Phactr3 |
| 1372365_at | Ras and Rab interactor 2 (predicted), Rin2_predicted |
| 1386960_at | solute carrier family 37 (glucose-6-phosphate transporter), member 4, Slc37a4 |
| 1372117_at | myotubularin related protein 10, Mtmr10 |
| 1383443_at | similar to UPF0308 protein C9orf21, LOC498685 |
| 1374236_at | leucine-rich repeat LGI family, member 2 (predicted), Lgi2_predicted |
| 1391194_at | Sal-like 1 (*Drosophila*) (predicted), Sall1_predicted |
| 1398606_at | golgi integral membrane protein 4, Golim4 |
| 1390289_at | FIG4 homolog (*S. cerevisiae*), Fig4 |
| 1371421_at | similar to 3-oxoacid CoA transferase 1, LOC678860 |
| 1379257_at | erythrocyte protein band 4.1-like 4a (predicted), Epb4.1l4a_predicted |
| 1370941_at | platelet derived growth factor receptor, alpha polypeptide, Pdgfra |
| 1392739_a_at | endonuclease/exonuclease/phosphatase family domain containing 1, Eepd1 |
| 1376187_at | Solute carrier family 35 (UDP-glucuronic acid/UDP-N-acetylgalactosamine dual transporter), member D1 (predicted), Slc35d1_predicted |

TABLE 1-continued

| Accession No. | Description |
| --- | --- |
| 1397267_at | RIM binding protein 2, Rimbp2 |
| 1384009_at | nuclear prelamin A recognition factor, Narf |
| 1384238_at | tweety homolog 2 (*Drosophila*), Ttyh2 |
| 1385175_at | homeo box B13 (predicted), Hoxb13_predicted |
| 1389054_at | similar to RIKEN cDNA 0610040J01, LOC498368 |
| 1396492_at | Nfat activating molecule with ITAM motif 1, Nfam1 |
| 1375909_at | similar to glutathione transferase GSTM7-7, MGC108896 |
| 1392040_at | spindle assembly 6 homolog (*C. elegans*) (predicted), Sass6_predicted |
| 1375353_at | Cdk5 and Abl enzyme substrate 1 (predicted), Cables1_predicted |
| 1390993_at | phenazine biosynthesis-like protein domain containing, Pbld |
| 1372069_at | ankyrin repeat domain 15, Ankrd15 |
| 1389787_at | PTK7 protein tyrosine kinase 7 (predicted), Ptk7_predicted |
| 1390168_a_at | DPH4 homolog (JJJ3, *S. cerevisiae*), Dph4 |
| 1397861_at | V-set and transmembrane domain containing 2B, Vstm2b |
| 1368160_at | insulin-like growth factor binding protein 1, Igfbp1 |
| 1382478_at | BTB (POZ) domain containing 3 (predicted), Btbd3_predicted |
| 1389003_at | Rho-related BTB domain containing 3 (predicted), Rhobtb3_predicted |
| 1370407_at | prenylcysteine oxidase 1, Pcyox1 |
| 1384331_at | sulfiredoxin 1 homolog (*S. cerevisiae*), Srxn1 |
| 1392789_at | solute carrier family 25, member 36, Slc25a36 |
| 1390481_a_at | ubiquitin-conjugating enzyme E2T (putative) (predicted), Ube2t_predicted |
| 1377599_at | lipin 1, Lpin1 |
| 1369686_at | doublecortin-like kinase 1, Dclk1 |
| 1370106_at | fibroblast growth factor 18, Fgf18 |
| 1390050_at | similar to Golgi phosphoprotein 2 (Golgi membrane protein GP73), LOC680692 /// LOC682869 |
| 1390647_at | putative homeodomain transcription factor 2 (predicted), Phtf2_predicted |
| 1371131_a_at | thioredoxin interacting protein, Txnip |
| 1388703_at | endothelial cell adhesion molecule, Esam |
| 1381969_at | similar to Recombining binding protein suppressor of hairless (J kappa-recombination signal binding protein) (RBP-J kappa), LOC679028 |
| 1379541_at | transmembrane and tetratricopeptide repeat containing 4, Tmtc4 |
| 1373398_at | Tripartite motif protein 37 (predicted), Trim37_predicted |
| 1367806_at | glutaminase, Gls |
| 1388973_at | procollagen, type IX, alpha 1, Col9a1 |
| 1385321_at | similar to Protein arginine N-methyltransferase 4 (Heterogeneous nuclear ribonucleoprotein methyltransferase-like protein 4), LOC688502 |
| 1370416_at | Max dimerization protein 3, Mxd3 |
| 1376873_at | cerebellin 1, Cbln1 |
| 1375423_at | hypothetical protein LOC689959, LOC689959 |
| 1373291_at | deleted in liver cancer 1, Dlc1 |
| 1377729_at | elongation of very long chain fatty acids (FEN1/Elo2, SUR4/Elo3, yeast)-like 4 (predicted), Elovl4_predicted |
| 1392943_at | membrane bound O-acyltransferase domain containing 2, Mboat2 |
| 1367899_at | coagulation factor II (thrombin) receptor, F2r |
| 1389067_at | solute carrier organic anion transporter family, member 4a1, Slco4a1 |
| 1370158_at | myosin, heavy polypeptide 10, non-muscle, Myh10 |
| 1396112_at | myotubularin related protein 10, Mtmr10 |
| 1387503_at | carboxypeptidase N, polypeptide 1, Cpn1 |
| 1389632_at | Rho-related BTB domain containing 1 (predicted), Rhobtb1_predicted |
| 1386129_at | inhibitor of growth family, member 2, Ing2 |
| 1377669_at | RAB27A, member RAS oncogene family, Rab27a |
| 1379817_at | purine-rich element binding protein G (predicted), Purg_predicted |
| 1379302_at | recombining binding protein suppressor of hairless (*Drosophila*) (predicted) /// similar to Recombining binding protein suppressor of hairless (J kappa-recombination signal binding protein) (RBP-J kappa), LOC679028 /// Rbpsuh_predicted |
| 1374333_at | similar to RIKEN cDNA 1110007C09 (predicted), RGD1306058_predicted |
| 1383433_at | kelch-like 23 (*Drosophila*) (predicted), Klhl23_predicted |
| 1370059_at | neurofilament, light polypeptide, Nefl |
| 1368174_at | EGL nine homolog 3 (*C. elegans*), Egln3 |

TABLE 1-continued

| Accession No. | Description |
|---|---|
| 1391871_at | StAR-related lipid transfer (START) domain containing 13, Stard13 |
| 1395160_at | proline-rich transmembrane protein 3, Prrt3 |
| 1367869_at | oxidation resistance 1, Oxr1 |
| 1381974_at | BTB (POZ) domain containing 3 (predicted), Btbd3_predicted |
| 1393101_at | F-box and leucine-rich repeat protein 10, Fbxl10 |
| 1374846_at | hexamethylene bis-acetamide inducible 1, Hexim1 |
| 1374748_at | serine hydroxymethyltransferase 1 (soluble), Shmt1 |
| 1375877_at | synaptotagmin IV, Syt4 |
| 1398296_at | glycerophosphodiester phosphodiesterase 1, Gde1 |
| 1371963_at | propionyl-coenzyme A carboxylase, alpha polypeptide, Pcca |
| 1398484_at | similar to TBC1 domain family, member 8 (with GRAM domain); vascular Rab-GAP/TBC-containing (predicted), RGD1308221_predicted |
| 1391077_at | claspin homolog (Xenopus laevis) (predicted), Clspn_predicted |
| 1369735_at | growth arrest specific 6, Gas6 |
| 1390406_at | Rho GTPase activating protein 18 (predicted), Arhgap18_predicted |
| 1384516_at | Metal response element binding transcription factor 2, Mtf2 |
| 1370247_a_at | peripheral myelin protein 22, Pmp22 |
| 1387623_at | stanniocalcin 1, Stc1 |
| 1386577_at | kelch-like 23 (*Drosophila*) (predicted), Klhl23_predicted |
| 1370237_at | hydroxyacyl-Coenzyme A dehydrogenase, Hadh |
| 1385302_at | glycerophosphodiester phosphodiesterase domain containing 1 (predicted), Gdpd1_predicted |
| 1373959_at | protein phosphatase 2 (formerly 2A), regulatory subunit A (PR 65), beta isoform, Ppp2r1b |
| 1398398_at | homeo box A10, Hoxa10 |
| 1383601_at | CDNA clone MGC: 188768 IMAGE: 9101044, — |
| 1370268_at | potassium voltage-gated channel, shaker-related subfamily, member 5, Kcna5 |
| 1389549_at | proline synthetase co-transcribed (predicted), Prosc_predicted |
| 1374160_at | transmembrane and coiled-coil domains 2, Tmcc2 |
| 1374890_at | Transcribed locus, strongly similar to NP_005656.4 ecotropic viral integration site 5 [*Homo sapiens*], — |
| 1390228_at | amine oxidase, flavin containing 1 (predicted), Aof1_predicted |
| 1378235_at | glycerophosphodiester phosphodiesterase domain containing 1 (predicted), Gdpd1_predicted |
| 1392406_at | IAP promoted placental gene (predicted), Ipp_predicted |
| 1371983_at | Josephin domain containing 1, Josd1 |
| 1389791_at | ceroid-lipofuscinosis, neuronal 8, Cln8 |
| 1392165_at | inhibitor of growth family, member 2, Ing2 |
| 1387805_at | BCL2/adenovirus E1B 19 kDa-interacting protein 3, Bnip3 |
| 1374491_at | CKLF-like MARVEL transmembrane domain containing 8, Cmtm8 |
| 1387310_at | ATPase, Ca++ transporting, type 2C, member 2, Atp2c2 |
| 1384852_at | RAB27A, member RAS oncogene family, Rab27a |
| 1368924_at | growth hormone receptor, Ghr |
| 1368964_at | leucine rich repeat protein 3, neuronal, Lrrn3 |
| 1376213_at | similar to Rap2-binding protein 9, MGC124740 |
| 1369696_at | Ras-related GTP binding B, RragB |
| 1373043_at | stromal cell-derived factor 2-like 1 (predicted), Sdf2l1_predicted |
| 1372782_a_at | adenosine monophosphate deaminase 2 (isoform L), Ampd2 |
| 1383382_at | similar to jumonji protein, LOC681740 |
| 1390028_at | dual-specificity tyrosine-(Y)-phosphorylation regulated kinase 2 (predicted), Dyrk2_predicted |
| 1383326_a_at | programmed cell death 4, Pdcd4 |
| 1399005_at | protein phosphatase 2, regulatory subunit B (B56), alpha isoform (predicted), Ppp2r5a_predicted |
| 1389301_at | similar to muscleblind-like 2 isoform 1, LOC680445 |
| 1368440_at | solute carrier family 3, member 1, Slc3a1 |
| 1377869_at | CCR4 carbon catabolite repression 4-like B (*S. cerevisiae*), Ccrn4lb |
| 1372093_at | Max interacting protein 1, Mxi1 |
| 1370548_at | solute carrier family 16 (monocarboxylic acid transporters), member 10, Slc16a10 |
| 1390249_at | septin 14, Sept14 |
| 1388919_at | zinc finger protein 541, Zfp541 |
| 1397173_at | similar to Serine/threonine-protein kinase WNK3 (Protein kinase, lysine-deficient 3) (predicted), RGD1563131_predicted |
| 1382814_at | odd Oz/ten-m homolog 3 (*Drosophila*) (predicted), Odz3_predicted |
| 1373659_at | hypothetical protein LOC688257, LOC688257 |
| 1391906_at | cortistatin /// kinesin family member 1B, Cort /// Kif1b |
| 1378430_at | monooxygenase, DBH-like 1, Moxd1 |
| 1373656_at | protein phosphatase 1, regulatory subunit 3D, Ppp1r3d |
| 1376758_at | inhibitor of growth family, member 1, Ing1 |
| 1375059_at | zinc finger protein 652, Zfp652 |
| 1374957_at | similar to ribosomal protein L27a (predicted), RGD1560633_predicted |
| 1384877_at | aquaporin 11, Aqp11 |
| 1370054_at | cyclin-dependent kinase inhibitor 2C (p18, inhibits CDK4), Cdkn2c |
| 1367755_at | cysteine dioxygenase 1, cytosolic, Cdo1 |
| 1383328_x_at | programmed cell death 4, Pdcd4 |
| 1379440_at | follistatin-like 3, Fstl3 |
| 1395623_at | glutaminyl-peptide cyclotransferase-like (predicted), Qpctl_predicted |
| 1370036_at | sulfite oxidase, Suox |
| 1369670_at | Cd200 antigen, Cd200 |
| 1392953_at | protein tyrosine phosphatase-like (proline instead of catalytic arginine), member a, Ptpla |
| 1383534_at | Transcribed locus, moderately similar to XP_001479249.1 PREDICTED: similar to zinc finger protein 605 [*Mus musculus*], — |
| 1384885_at | tektin 2, Tekt2 |
| 1368122_at | ring finger protein 103, Rnf103 |
| 1373625_at | serine hydroxymethyltransferase 1 (soluble), Shmt1 |
| 1388856_at | kit ligand, Kitl |
| 1367702_at | acyl-Coenzyme A dehydrogenase, medium chain, Acadm |
| 1374625_at | hairy and enhancer of split 6 (*Drosophila*), Hes6 |
| 1369785_at | phosphoribosyl pyrophosphate amidotransferase, Ppat |
| 1385829_at | obscurin-like 1, Obsl1 |
| 1383962_at | SIVA1, apoptosis-inducing factor, Siva1 |
| 1383666_at | peptidyl-tRNA hydrolase 1 homolog (*S. cerevisiae*) (predicted), Ptrh1_predicted |
| 1373345_at | adhesion molecule with Ig like domain 2, Amigo2 |
| 1391919_at | transcription elongation regulator 1-like, Tcerg1l |
| 1384392_at | cytochrome P450, family 26, subfamily b, polypeptide 1, Cyp26b1 |
| 1374540_at | cell division cycle associated 7, Cdca7 |
| 1385503_at | similar to O-acetyltransferase, LOC678772 |
| 1393439_a_at | progressive ankylosis, Ank |
| 1374030_at | similar to KIAA0999 protein, LOC684112 |
| 1377995_at | integrin alpha FG-GAP repeat containing 3, Itfg3 |
| 1393218_at | similar to 2410024A21Rik protein, RGD1304878 |
| 1383722_at | proline synthetase co-transcribed (predicted), Prosc_predicted |
| 1374235_at | regulator of calcineurin 2, Rcan2 |
| 1372248_at | sestrin 1 (predicted), Sesn1_predicted |
| 1387670_at | glycerol-3-phosphate dehydrogenase 2, mitochondrial, Gpd2 |
| 1387032_at | cholecystokinin, Cck |
| 1395269_s_at | gamma-aminobutyric acid (GABA-A) receptor, subunit delta, Gabrd |
| 1387662_at | synaptotagmin IV, Syt4 |
| 1369010_at | CHK2 checkpoint homolog (*S. pombe*), Chek2 |
| 1393347_at | integrin alpha L, Itgal |
| 1376963_at | dual-specificity tyrosine-(Y)-phosphorylation regulated kinase 2 (predicted), Dyrk2_predicted |
| 1371763_at | similar to RIKEN cDNA 4931406C07, RGD1309534 |
| 1386978_at | BCL2/adenovirus E1B interacting protein 3-like, Bnip3l |
| 1370814_at | dehydrogenase/reductase (SDR family) member 4, Dhrs4 |
| 1369457_a_at | synaptotagmin-like 4, Sytl4 |
| 1367853_at | solute carrier family 12 (sodium/potassium/chloride transporters), member 2, Slc12a2 |
| 1392079_at | A kinase (PRKA) anchor protein 7, Akap7 |
| 1395968_at | similar to Myosin-15 (Myosin XV) (Unconventional myosin-15), LOC688264 |
| 1369412_a_at | solute carrier family 19 (sodium/hydrogen exchanger), member 1, Slc19a1 |
| 1381515_at | CDNA clone IMAGE: 7123062, — |
| 1370120_at | follistatin-like 3, Fstl3 |
| 1379258_at | kelch-like 5 (*Drosophila*), Klhl5 |

TABLE 1-continued

| Accession No. | Description |
|---|---|
| 1373734_at | Solute carrier organic anion transporter family, member 3a1, Slco3a1 |
| 1389084_at | Transcribed locus, weakly similar to XP_001480799.1 PREDICTED: hypothetical protein [*Mus musculus*], — |
| 1393109_at | CDNA clone IMAGE: 7302574, — |
| 1373480_at | heat shock 70 kDa protein 12A (predicted), Hspa12a_predicted |
| 1367791_at | receptor (calcitonin) activity modifying protein 1, Ramp1 |
| 1396317_at | cell cycle progression 1 (predicted), Ccpg1_predicted |
| 1387521_at | programmed cell death 4, Pdcd4 |
| 1374976_a_at | Sterol O-acyltransferase 1, Soat1 |
| 1384210_at | MICAL C-terminal like, Micalcl |
| 1369000_at | neurotrophic tyrosine kinase, receptor, type 1, Ntrk1 |
| 1389876_at | Calcium/calmodulin-dependent protein kinase II inhibitor 1, Camk2n1 |
| 1371679_at | synaptopodin 2, Synpo2 |
| 1383444_at | solute carrier family 24 (sodium/potassium/calcium exchanger), member 2, Slc24a2 |
| 1379108_at | Similar to ADP-ribosylation factor guanine nucleotide factor 6 isoform a (predicted), RGD1559968_predicted |
| 1387271_at | phytanoyl-CoA hydroxylase, Phyh |
| 1390207_at | large tumor suppressor 2 (predicted), Lats2_predicted |
| 1368514_at | monoamine oxidase B, Maob |
| 1393196_at | kelch-like 23 (*Drosophila*) (predicted), Klhl23_predicted |
| 1379608_at | RGD1560010 (predicted), RGD1560010_predicted |
| 1388958_a_at | solute carrier family 2 (facilitated glucose transporter), member 4, Slc2a4 |
| 1383300_at | kelch-like 24 (*Drosophila*), Klhl24 |
| 1374557_at | G protein-coupled receptor 177, Gpr177 |
| 1371113_a_at | transferrin receptor, Tfrc |
| 1393848_at | ribonucleotide reductase M2, Rrm2 |

comprising the step of administering a compound according to claim 1 to a patient in need thereof.

33. The method according to claim 32, wherein said disease or disorder is a cell proliferative disorder.

34. A compound of Formula II:

Formula II

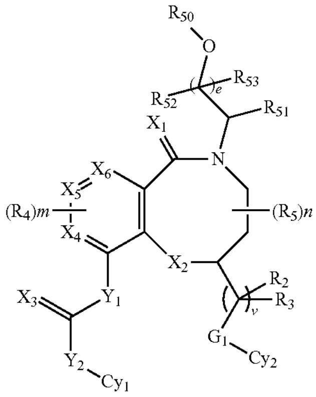

wherein e is 0, 1, 2, 3 or 4;

$R_{50}$ is —C(O)$R_{54}$, —C(O)N(H)$R_{54}$, —C(S)$R_{54}$, —C(S)N(H)$R_{54}$;

wherein $R_{54}$ is alkyl or substituted alkyl, $-(CH_2)_2O(CH_2CH_2O)_fCH_2CH_2NH_2$, $-(CH_2)_2-O-(CH_2CH_2)_gNH_2$, $-(CH_2CH_2)_gNH_2$, $-(CH_2)_2-O-(CH_2CH_2O)_fCH_2CH_2SH$, $-(CH_2)_2-O-(CH_2CH_2)_gSH$, $-(CH_2CH_2)_gOH$, $-(CH_2)_2-O-(CH_2CH_2O)_fCH_2CH_2OH$, $-(CH_2)_2-O-(CH_2CH_2)_gOH$, $-(CH_2CH_2)_gOH$;

wherein each f and g is independently, an integer between 0 and 500, preferably, 0, 1, 2, 3, 4, 5, 6, 7, 8, 9, 10, 11, 12, 13, 14, 15 or 17;

each $R_{51}$, $R_{52}$ and $R_{53}$ is independently hydrogen, halogen, —$OR_{10}$, —$SR_{10}$, —$NR_{10}R_{11}$, —C(O)$R_{10}$, —C(O)$OR_{10}$, —C(O)$NR_{10}R_{11}$, —N($R_{10}$)C(O)$R_{11}$, —$CF_3$, —CN, —$NO_2$, —$N_3$, acyl, alkoxy, substituted alkoxy, alkylamino, substituted alkylamino, dialkylamino, substituted dialkylamino, substituted or unsubstituted alkylthio, substituted or unsubstituted alkylsulfonyl, optionally substituted aliphatic, optionally substituted aryl or optionally substituted heterocyclyl.

* * * * *

UNITED STATES PATENT AND TRADEMARK OFFICE

CERTIFICATE OF CORRECTION

PATENT NO. : 8,741,905 B2
APPLICATION NO. : 13/887466
DATED : June 3, 2014
INVENTOR(S) : Bridget Wagner, Jeremy Duvall and Danny Hung-Chieh Chou It is certified that error appears in the above-identified patent and that said Letters Patent is hereby corrected as shown below:

In the Claims:

Column 77, Claim 2, line 62: please replace "$-SR_{11}$," with -- $-SR_{10}$,--.

Column 108, Claim 24, lines 58-59: after "from" please delete "the cell proliferative disorder is selected from".

Column 109, Claim 31, lines 33-34: after "from" please delete "the cell proliferative disorder is selected from".

Column 113, Claim 32, line 34: under Accession No. 1399153_at, please delete "RABSB" and replace with --RAB5B--.

Signed and Sealed this
Ninth Day of September, 2014

Michelle K. Lee

Michelle K. Lee
*Deputy Director of the United States Patent and Trademark Office*